(12) United States Patent
Xu et al.

(10) Patent No.: US 11,912,768 B2
(45) Date of Patent: Feb. 27, 2024

(54) SINGLE DOMAIN ANTIBODY AND DERIVATIVE PROTEINS THEREOF AGAINST CTLA4

(71) Applicants: SUZHOU ALPHAMAB CO., LTD., Shanghai (CN); Xitian Zhang, Shanghai (CN); Xin Zhang, Shanghai (CN)

(72) Inventors: Ting Xu, Suzhou (CN); Xiaoxiao Wang, Suzhou (CN); Jie Li, Suzhou (CN); Haiyan Wu, Suzhou (CN); Li Gao, Suzhou (CN); Qian Chu, Suzhou (CN); Yu Bai, Suzhou (CN)

(73) Assignees: SUZHOU ALPHAMAB CO., LTD., Suzhou (CN); XITIAN ZHANG, Shanghai (CN); XIN ZHANG, Shanghai (CN)

( * ) Notice: Subject to any disclaimer, the term of this patent is extended or adjusted under 35 U.S.C. 154(b) by 309 days.

(21) Appl. No.: 17/369,169

(22) Filed: Jul. 7, 2021

(65) Prior Publication Data
US 2022/0177588 A1    Jun. 9, 2022

Related U.S. Application Data

(62) Division of application No. 16/302,583, filed as application No. PCT/CN2017/085038 on May 19, 2017, now Pat. No. 11,091,549.

(30) Foreign Application Priority Data

May 19, 2016 (CN) .......................... 201610332590.7

(51) Int. Cl.
| | |
|---|---|
| C07K 16/00 | (2006.01) |
| C07K 16/28 | (2006.01) |
| A61P 35/00 | (2006.01) |
| A61K 39/395 | (2006.01) |
| C07K 16/22 | (2006.01) |
| C07K 16/32 | (2006.01) |
| C12N 15/70 | (2006.01) |
| A61K 39/00 | (2006.01) |

(52) U.S. Cl.
CPC ...... *C07K 16/2818* (2013.01); *A61K 39/3955* (2013.01); *A61K 39/39558* (2013.01); *A61P 35/00* (2018.01); *C07K 16/22* (2013.01); *C07K 16/2863* (2013.01); *C07K 16/32* (2013.01); *C12N 15/70* (2013.01); *A61K 2039/505* (2013.01); *C07K 2317/24* (2013.01); *C07K 2317/52* (2013.01); *C07K 2317/565* (2013.01); *C07K 2317/569* (2013.01)

(58) Field of Classification Search
CPC ................ C07K 16/2818; C07K 16/22; C07K 2317/565; C07K 2317/569; A61K 39/3955; A61K 39/39558; A61P 35/00
See application file for complete search history.

(56) References Cited

FOREIGN PATENT DOCUMENTS

| | | |
|---|---|---|
| CN | 101074264 A | 11/2007 |
| CN | 101268101 A | 9/2008 |
| CN | 103833851 A | 6/2014 |
| CN | 103842383 A | 6/2014 |
| CN | 106046164 A | 10/2016 |
| CN | 106046165 A | 10/2016 |
| CN | 106188297 A | 12/2016 |
| CN | 106220732 A | 12/2016 |
| WO | WO-200114424 A2 | 3/2001 |
| WO | WO-200114424 A3 | 9/2001 |
| WO | WO-2007008463 A2 | 1/2007 |
| WO | WO-2010014784 A2 | 2/2010 |
| WO | WO-2012/158818 A2 | 11/2012 |
| WO | WO-2016015675 A1 | 2/2016 |

OTHER PUBLICATIONS

International Search Report for Application No. PCT/CN2017/085038, dated Aug. 10, 2017.
European Search Report for European Application No. 17798775.7, dated Dec. 16, 2019.
Martin Rossotti et al., "Streamlined method for parallel identification of single domain antibodies to membrane receptors on whole cells," *Biochimica et Biophysica Acta*, vol. 1850, No. 7, pp. 1397-1404 (2015).
Jessica R. Ingram et al., "Anti-CTLA-4 therapy requires an Fc domain for efficacy," *Proc. Natl. Acad. Sci.*, vol. 115, No. 15, pp. 3912-3917 (2018).

*Primary Examiner* — Lei Yao
(74) *Attorney, Agent, or Firm* — MARSHALL, GERSTEIN & BORUN LLP

(57) ABSTRACT

The present invention relates to the field of medical biology, and discloses a single domain antibody and derivative proteins thereof against CTLA4. In particular, the present invention discloses a CTLA4 binding protein and the use thereof, especially the use for treating and/or preventing CTLA4 relevant diseases such as tumor.

9 Claims, 18 Drawing Sheets
Specification includes a Sequence Listing.

FIG. 4A

| SEQ ID NO: | Name | | |
|---|---|---|---|
| SEQ ID NO: 101 | huC27V1 | 1 | QVQLVESGGGLVQPGGSLRLSCAASGYIYSAYCMGWFRQAPGKERVGVAAISIGGGSTYY 60 |
| SEQ ID NO: 102 | huC27V2 | 1 | QVQLVESGGGLVQPGGSLRLSCAASGYIYSAYCMGWFRQAPGKERVGVAAISIGGGSTYY 60 |
| SEQ ID NO: 103 | huC27V3 | 1 | QVQLVESGGGLVQPGGSLRLSCAASGYIYSAYCMGWFRQAPGKGLVGVAAISIGGGSTYY 60 |
| SEQ ID NO: 104 | huC27V4 | 1 | QVQLVESGGGLVQPGGSLRLSCAASGYIYSAYCMGWFRQAPGKGLEGVAAISIGGGSTYY 60 |
| SEQ ID NO: 105 | huC27V5 | 1 | QVQLVESGGGLVQPGGSLRLSCAASGYIYSAYCMGWFRQAPGKEREGVAAISIGGGSTYY 60 |
| | | | **********************************************::*** |

| SEQ ID NO: 101 | huC27V1 | 61 | ADSVKGRFTISQDNSKNTLYLQMNSLRAEDTAVYYCAADVIPTETCLGGSWSGPFGYWG 119 |
|---|---|---|---|
| SEQ ID NO: 102 | huC27V2 | 61 | ADSVKGRFTISRDNSKNTLYLQMNSLRAEDTAVYYCAADVIPTETCLGGSWSGPFGYWG 119 |
| SEQ ID NO: 103 | huC27V3 | 61 | ADSVKGRFTISRDNSKNTLYLQMNSLRAEDTAVYYCAADVIPTETCLGGSWSGPFGYWG 119 |
| SEQ ID NO: 104 | huC27V4 | 61 | ADSVKGRFTISRDNSKNTLYLQMNSLRAEDTAVYYCAADVIPTETCLGGSWSGPFGYWG 119 |
| SEQ ID NO: 105 | huC27V5 | 61 | ADSVKGRFTISRDNSKNTLYLQMNSLRAEDTAVYYCAADVIPTETCLGGSWSGPFGYWG 119 |
| | | | *********:********************************************* |

FIG. 4B

| SEQ ID NO: 106 | huC1V1 | 1 | QVQLVESGGGLVQPGGSLRLSCAASGYIYSAYCMGWFRQAPGKEREGVAAIYIGGGSTYY 60 |
|---|---|---|---|
| SEQ ID NO: 107 | huC1V2 | 1 | QVQLVESGGGLVQPGGSLRLSCAASGYIYSAYCMGWFRQAPGKEREGVAAIYIGGGSTYY 60 |
| SEQ ID NO: 108 | huC1V3 | 1 | QVQLVESGGGLVQPGGSLRLSCAASGYIYSAYCMGWFRQAPGKGLVGVAAIYIGGGSTYY 60 |
| SEQ ID NO: 109 | huC1V4 | 1 | QVQLVESGGGLVQPGGSLRLSCAASGYIYSAYCMGWFRQAPGKGLEGVAAIYIGGGSTYY 60 |
| | | | *******************************************  *:************ |

| SEQ ID NO: 106 | huC1V1 | 61 | ADSVKGRFTISQDNSKNTLYLQMNSLRAEDTAVYYCAADVIPTETCLGGSWSGPFGYWGQ 120 |
|---|---|---|---|
| SEQ ID NO: 107 | huC1V2 | 61 | ADSVKGRFTISRDNSKNTLYLQMNSLRAEDTAVYYCAADVIPTETCLGGSWSGPFGYWGQ 120 |
| SEQ ID NO: 108 | huC1V3 | 61 | ADSVKGRFTISRDNSKNTLYLQMNSLRAEDTAVYYCAADVIPTETCLGGSWSGPFGYWGQ 120 |
| SEQ ID NO: 109 | huC1V4 | 61 | ADSVKGRFTISRDNSKNTLYLQMNSLRAEDTAVYYCAADVIPTETCLGGSWSGPFGYWGQ 120 |
| | | | *********:********************************************* |

| LD-Fc | | | | | | | | |
|---|---|---|---|---|---|---|---|---|
| Animal | Sex | t1/2 | Cmax | AUClast | AUCINF_obs | Vz_obs | Cl_obs | MRTlast |
| | | h | ug/mL | h*ug/mL | h*ug/mL | mL/kg | mL/h/kg | h |
| | mean | 140.79 | 312.02 | 13717.18 | 14948.82 | 136.22 | 0.68 | 128.27 |
| | SD | 9.79 | 46.36 | 2204.47 | 2487.75 | 17.96 | 0.11 | 8.07 |

| Tet-Fc | | | | | | | | |
|---|---|---|---|---|---|---|---|---|
| Animal | Sex | t1/2 | Cmax | AUClast | AUCINF_obs | Vz_obs | Cl_obs | MRTlast |
| | | h | ug/mL | h*ug/mL | h*ug/mL | mL/kg | mL/h/kg | h |
| | mean | 280.97 | 315.95 | 26617.98 | 37451.86 | 110.83 | 0.28 | 162.45 |
| | SD | 37.63 | 34.88 | 4459.10 | 7183.06 | 19.37 | 0.06 | 6.40 |

FIG. 17

SINGLE DOMAIN ANTIBODY AND DERIVATIVE PROTEINS THEREOF AGAINST CTLA4

INCORPORATION BY REFERENCE OF MATERIAL SUBMITTED ELECTRONICALLY

This application contains, as a separate part of disclosure, a sequence listing in computer-readable form (filename: 53659A_SubSeqListing.txt; Size: 123,096 bytes: Created: Sep. 22, 2021) which is incorporated by reference herein in its entirety.

TECHNICAL FIELD

The present invention relates to the field of medical biology, and discloses a single domain antibody and derivative proteins thereof against CTLA4. In particular, the present invention discloses a CTLA4 binding protein and the use thereof, especially the use for treating and/or preventing CTLA4 relating diseases such as tumor.

BACKGROUND

Animals of Camelidae, such as camels or alpacas, are capable of producing a heavy chain antibody that naturally deficient with light chain. The molecule of heavy chain antibody contains only one heavy chain variable region (VHH) and two conventional CH2 and CH3 regions, but has the complete antigen binding function and is not as easy to aggregate as artificially engineered single-chain antibody fragments (scFv). More importantly, the recombinantly expressed VHH domain has structural stability and antigen binding activity comparable to that of the original heavy chain antibody, and is the smallest unit currently known that can bind to target antigen, called Nanobody or heavy chain single domain antibody. Due to its special structural properties, heavy chain single domain antibody has the advantages of both traditional antibodies and small molecule drugs, and overcomes the shortcomings of traditional antibody, such as long development cycle, low stability, and harsh storage conditions, representing the direction of developing a new generation of antibody therapy.

Tumor-associated antigens expressed by tumor cells are the basis for producing an effective immune response. However, when antigens are bound to major histocompatibility complex (MHC) molecules on the surface of antigen-presenting cells (APCs) and presented, co-stimulatory signals are required to promote activation of effector T cells. Studies have shown that many tumors can escape the patient's own immune system, in part because of the lack of costimulatory signals to fully activate the T cells, and most likely due to immunosuppression induced by regulatory T cells (Treg). Binding of CD80 or CD86 on the antigen-presenting cells to CD28 on the T cells is a key costimulatory signal. Human cytotoxic T lymphocyte-associated antigen 4 (CTLA4) is a negative regulator of T cell expression and has a higher affinity for CD80 and CD86. It blocks the co-stimulatory signal of CD28 and meanwhile activates the T cell negative regulatory pathway. The immunosuppressive effect of CTLA4 plays an important role in limiting the autoimmune response. However, in the tumor immune response, CTLA4-mediated inhibition mechanism is often one of the reasons why tumor cells can escape from the immune system. Thus, T cell mediated anti-tumor responses can be enhanced by blocking the interaction of CTLA4 with CD80 or CD86.

There is still a need in the art for anti-CTLA4 antibody, especially a heavy chain single domain antibody against CTLA4, which can bind to CTLA4 with high affinity and block the binding of CTLA4 to CD80.

BRIEF DESCRIPTION OF THE INVENTION

The present inventors have obtained anti-CTLA4 heavy chain single domain antibody (VHH) with high specificity, high affinity and high stability by screening with phage display technology.

In a first aspect, the invention provides a CTLA4-binding protein comprising an immunoglobulin single variable domain that specifically binds to CTLA4.

In another aspect, the present invention relates to a nucleic acid molecule encoding the CTLA4-binding protein, and an expression vector and host cell containing said nucleic acid molecule.

The present invention further relates to a pharmaceutical composition comprising the CTLA4-binding protein of the invention.

The present invention further relates to a method for producing the CTLA4-binding protein of the invention.

The present invention further relates to use of the CTLA4-binding protein and pharmaceutical composition of the invention, especially the use and method for preventing and/or treating CTLA4 relating diseases.

DESCRIPTION OF DRAWINGS

FIG. 4. shows the sequence alignment of five humanized variants (A) of antibody No. C27 and four humanized variants (B) of antibody No. C1.

FIG. 17. shows the pharmacokinetic parameters of CTLA4 single domain antibody-Fc fusion proteins in rats.

DETAILED DESCRIPTION OF THE INVENTION

Definitions

Figure 1A:
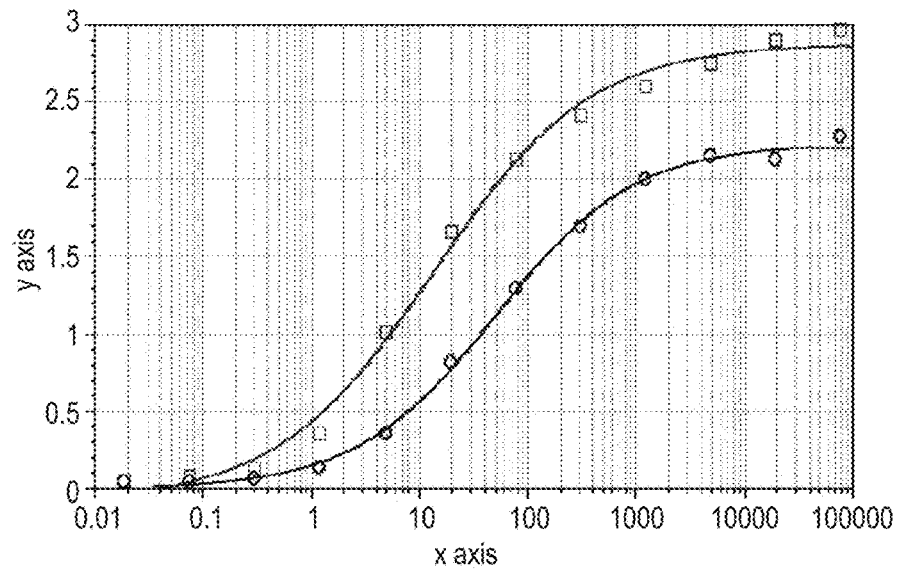
FIGS. 1A and 1B. shows the binding curves of CTLA4 heavy chain single domain antibodies to CTLA4-Fc antigen protein.

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd Ed.), Vols. 1-3, Cold Spring Harbor Laboratory Press (1989); Lewin, "Genes IV", Oxford University Press, New York, (1990), and Roitt et al., "Immunology" (2nd Ed.), Gower Medical Publishing, London, New York (1989), as well as to the general background art cited herein. Furthermore, unless indicated otherwise, all methods, steps, techniques and manipulations that are not specifically described in detail can be performed and have been performed in a manner known per se, as will be clear to the skilled person. Reference is for example again made to the standard handbooks, to the general background art referred to above and to the further references cited therein.

Unless indicated otherwise, the interchangeable terms "antibody" and "immunoglobulin"—whether used herein to refer to a heavy chain antibody or to a conventional 4-chain antibody—are used as general terms to include both the full-size antibody, the individual chains thereof, as well as all parts, domains or fragments thereof (including but not limited to antigen-binding domains or fragments such as VHH domains or VH/VL domains, respectively). In addition, the term "sequence" as used herein (for example in terms like "immunoglobulin sequence", "antibody sequence", "single variable domain sequence", "VHH sequence" or "protein sequence"), should generally be understood to include both the relevant amino acid sequence as well as nucleic acid sequences or nucleotide sequences encoding the same, unless the context requires a more limited interpretation.

The term "domain" (of a polypeptide or protein) as used herein refers to a folded protein structure which has the ability to retain its tertiary structure independently of the rest of the protein. Generally, domains are responsible for discrete functional properties of proteins, and in many cases may be added, removed or transferred to other proteins without loss of function of the remainder of the protein and/or of the domain.

The term "immunoglobulin domain" as used herein refers to a globular region of an antibody chain (such as e.g. a chain of a conventional 4-chain antibody or of a heavy chain antibody), or to a polypeptide that essentially consists of such a globular region. Immunoglobulin domains are characterized in that they retain the immunoglobulin fold characteristic of antibody molecules, which consists of a 2-layer sandwich of about 7 antiparallel beta-strands arranged in two beta-sheets, optionally stabilized by a conserved disulfide bond.

The term "immunoglobulin variable domain" as used herein means an immunoglobulin domain essentially consisting of four "framework regions" which are referred to in the art and hereinbelow as "framework region 1" or "FR1"; as "framework region 2" or "FR2"; as "framework region 3" or "FR3"; and as "framework region 4" or "FR4", respectively; which framework regions are interrupted by three "complementarity determining regions" or "CDRs", which are referred to in the art and hereinbelow as "complementarity determining region" or "CDR1"; as "complementarity determining region 2" or "CDR2"; and as "complementarity determining region 3" or "CDR3", respectively. Thus, the general structure or sequence of an immunoglobulin variable domain can be indicated as follows: FR1-CDR1-FR2-CDR2-FR3-CDR3-FR4. It is the immunoglobulin variable domain(s) that confer specificity to an antibody for the antigen by carrying the antigen-binding site.

The term "immunoglobulin single variable domain" as used herein means an immunoglobulin variable domain which is capable of specifically binding to an epitope of the antigen without pairing with an additional variable immunoglobulin domain. One example of immunoglobulin single variable domains in the meaning of the present invention is "domain antibody", such as the immunoglobulin single variable domains VH and VL (VH domains and VL domains). Another example of immunoglobulin single variable domains is "VHH domain" (or simply "VHH") from camelids, as defined hereinafter.

"VHH domains", also known as heavy chain single domain antibodies, VHHs, $V_H H$ domains, VHH antibody fragments, and VHH antibodies, are the antigen binding immunoglobulin variable domain of "heavy chain antibodies" (i.e., "antibodies devoid of light chains") (Hamers-Casterman C, Atarhouch T, Muyldermans S, Robinson G, Hamers C, Songa E B, Bendahman N, Hamers R.: "Naturally occurring antibodies devoid of light chains"; Nature 363, 446-448 (1993)). The term "VHH domain" has been used in order to distinguish these variable domains from the heavy chain variable domains that are present in conventional 4-chain antibodies (which are referred to herein as "VH domains") and from the light chain variable domains that are present in conventional 4-chain antibodies (which are referred to herein as "VL domains"). VHH domains can specifically bind to an epitope without an additional antigen binding domain (as opposed to VH or VL domains in a conventional 4-chain antibody, in which case the epitope is recognized by a VL domain together with a VH domain). VHH domains are small, robust and efficient antigen recognition units formed by a single immunoglobulin domain.

In the context of the present invention, the terms heavy chain single domain antibody, VHH domain, VHH, $V_H H$ domain, VHH antibody fragment, VHH antibody, as well as "Nanobody®" and "Nanobody® domain" ("Nanobody" being a trademark of the company Ablynx N.V.; Ghent; Belgium) are used interchangeably.

The amino acid residues of VHH domains from Camelids are numbered according to the general numbering for VH domains given by Kabat et al. ("Sequence of proteins of immunological interest", US Public Health Services, NIH Bethesda, Md., Publication No. 91), as shown e.g. in FIG. 2 of Riechmann and Muyldermans, J. Immunol. Methods 231, 25-38 (1999). According to this numbering, FR1 comprises the amino acid residues at positions 1-30,
CDR1 comprises the amino acid residues at positions 31-35,
FR2 comprises the amino acids at positions 36-49,
CDR2 comprises the amino acid residues at positions 50-65,
FR3 comprises the amino acid residues at positions 66-94,
CDR3 comprises the amino acid residues at positions 95-102, and
FR4 comprises the amino acid residues at positions 103-113.

However, it should be noted that—as is well known in the art for VH domains and for VHH domains—the total number of amino acid residues in each of the CDRs may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence.

Alternative methods for numbering the amino acid residues of VH domains, which methods can also be applied in an analogous manner to VHH domains, are known in the art. However, in the present description, claims and figures, the numbering according to Kabat and applied to VHH domains as described above will be followed, unless indicated otherwise.

The total number of amino acid residues in a VHH domain will usually be in the range of from 110 to 120, often between 112 and 115. It should however be noted that smaller and longer sequences may also be suitable for the purposes described herein.

Further structural characteristics and functional properties of VHH domains and polypeptides containing the same can be summarized as follows:

VHH domains (which have been "designed" by nature to functionally bind to an antigen without the presence of, and without any interaction with, a light chain variable domain) can function as a single, relatively small, functional antigen-binding structural unit, domain or polypeptide. This distinguishes the VHH domains from the VH and VL domains of conventional 4-chain antibodies, which by themselves are generally not suitable for practical application as single antigen-binding proteins or immunoglobulin single variable domains, but need to be combined in some form or another to provide a functional antigen-binding unit (as in for example conventional antibody fragments such as Fab fragments; in scFvs, which consist of a VH domain covalently linked to a VL domain).

Because of these unique properties, the use of VHH domains—either alone or as part of a larger polypeptide—offers a number of significant advantages over the use of conventional VH and VL domains, scFvs or conventional antibody fragments (such as Fab- or F(ab')2-fragments):

only a single domain is required to bind an antigen with high affinity and with high selectivity, so that there is no need to have two separate domains present, nor to assure that these two domains are present in the right spatial conformation and configuration (i.e. through the use of especially designed linkers, as with scFvs);

VHH domains can be expressed from a single gene and require no post-translational folding or modifications;

VHH domains can easily be engineered into multivalent and multispecific formats (formatted);

VHH domains are highly soluble and do not have a tendency to aggregate;

VHH domains are highly stable to heat, pH, proteases and other denaturing agents or conditions and, thus, may be prepared, stored or transported without the use of refrigeration equipments, conveying a cost, time and environmental savings;

VHH domains are easy and relatively cheap to prepare, even on a scale required for production;

VHH domains are relatively small (approximately 15 kDa, or 10 times smaller than a conventional IgG) compared to conventional 4-chain antibodies and antigen-binding fragments thereof, and therefore show high(er) penetration into tissues and can be administered in higher doses than such conventional 4-chain antibodies and antigen-binding fragments thereof;

VHH domains can show so-called cavity-binding properties (especially due to their extended CDR3 loop, compared to conventional VH domains) and can therefore also access targets and epitopes not accessible to conventional 4-chain antibodies and antigen-binding fragments thereof.

Methods of obtaining VHH domains binding to a specific antigen or epitope have been described earlier, e.g. in WO2006/040153 and WO2006/122786; R. van der Linden et al., Journal of Immunological Methods, 240 (2000) 185-195; Li et al., J Biol Chem., 287 (2012) 13713-13721; Deffar et al., African Journal of Biotechnology Vol. 8 (12), pp. 2645-2652, 17 June, 2009 and WO94/04678.

VHH domains derived from camelids can be "humanized" by replacing one or more amino acid residues in the amino acid sequence of the original VHH sequence by one or more of the amino acid residues that occur at the corresponding position(s) in a VH domain from a conventional 4-chain antibody from a human being (also referred to as "sequence optimization", and in addition to humanization, sequence optimization also encompasses other modification to the sequence by one or more mutations for providing improved VHH features, such as removing potential sites for post-translation modification). A humanized VHH domain can contain one or more fully human framework region sequences, and in a specific embodiment, containing IGHV3 human framework region sequence.

As used herein, "domain antibodies" especially refer to the VH or VL domains of non-camelid mammalians, in particular human 4-chain antibodies. In order to bind an epitope as a single antigen binding domain, i.e. without being paired with a VL or VH domain, respectively, specific selection for such antigen binding properties is required, e.g. by using libraries of human single VH or VL domain sequences.

Domain antibodies have, like VHHs, a molecular weight of approximately 13 to approximately 16 kDa and, if derived from fully human sequences, do not require humanization for e.g. therapeutical use in humans. As in the case of VHH domains, they are well expressed also in prokaryotic expression systems, providing a significant reduction in overall manufacturing cost.

"Domain antibodies" have been described in e.g. Ward, E. S., et al.: "Binding activities of a repertoire of single immunoglobulin variable domains secreted from *Escherichia coli*"; Nature 341:544-546(1989); Holt, L. J. et al.: "Domain antibodies: proteins for therapy"; TRENDS in Biotechnology 21(11):484-490 (2003).

Furthermore, it will also be clear to the skilled person that it is possible to "graft" one or more of the CDRs mentioned above onto other "scaffolds", including but not limited to human scaffolds or non-immunoglobulin scaffolds. Suitable scaffolds and techniques for such CDR grafting are known in the art.

As used herein, the term "epitope" refers to any antigenic determinant on an antigen to which the paratope of an antibody binds. Antigenic determinants typically contain chemically active surface groupings of molecules such as amino acids or sugar side chains and typically have specific three dimensional structural characteristics, as well as specific charge characteristics. For example, an epitope typically includes at least 3, 4, 5, 6, 7, 8, 9, 10, 11, 12, 13, 14 or 15 consecutive or non-consecutive amino acids in a unique spatial conformation, which can be "linear" or "conformational". See, e.g., Epitope Mapping Protocols in Methods in Molecular Biology, Vol. 66, G. E. Morris, Ed. (1996). In a linear epitope, all of the points of interaction between the protein and the interacting molecule (such as an antibody) occur linearly along the primary amino acid sequence of the protein. In a conformational epitope, the points of interaction occur across amino acid residues on the protein that are separated from one another.

Epitopes of a given antigen can be identified using a number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715. Similarly, conformational epitopes may be identified by determining spatial conformation of amino acids such as by, e.g., x-ray crystallography and 2-dimensional nuclear magnetic resonance. See, e.g., Epitope Mapping Protocols, supra.

Antibodies can be screened for competitive binding to a same epitope by conventional techniques known in the art. For example, antibodies compete or cross-compete for binding to antigen can be obtained by competitive or cross-competitive assays. A high throughput process for obtaining antibodies binding to a same epitope based upon their cross-competition is described in International Patent Publication No. WO 03/48731. Correspondingly, antibodies and antigen binding fragments thereof that compete with the antibody molecules of the invention for binding to same epitope on CTLA4 can be obtained by conventional techniques known in the art.

Generally, the term "specificity" refers to the number of different types of antigens or epitopes to which a particular antigen-binding molecule or antigen-binding protein (such as an immunoglobulin single variable domain of the invention) can bind. The specificity of an antigen-binding protein can be determined based on its affinity and/or avidity. The affinity, represented by the equilibrium constant for the dissociation of an antigen with an antigen-binding protein (KD), is a measure for the binding strength between an epitope and an antigen-binding site on the antigen-binding protein: the lesser the value of the KD, the stronger the binding strength between an epitope and the antigen-binding protein (alternatively, the affinity can also be expressed as the affinity constant (KA), which is 1/KD). As will be clear to the skilled person, affinity can be determined in a manner known per se, depending on the specific antigen of interest. Avidity is the measure of the strength of binding between an antigen-binding protein (such as an immunoglobulin, an antibody, an immunoglobulin single variable domain or a polypeptide containing it) and the pertinent antigen. Avidity is related to both the affinity between an epitope and its antigen binding site on the antigen-binding protein and the number of pertinent binding sites present on the antigen-binding protein.

Unless indicated otherwise, the term "CTLA4-binding protein" refers to any protein that can specifically bind to CTLA4. CTLA4-binding protein can encompass the antibodies or immunoconjugates against CTLA4 as defined herein. The term "CTLA4-binding protein" encompasses immunoglobulin super family antibodies (IgSF), or CDR-grafted molecules.

CTLA4-binding molecule of the invention may contain at least one CTLA4-binding immunoglobulin single variable domain, such as VHH. In some embodiments, CTLA4-binding molecule of the invention may contain two, three, four or more CTLA4-binding immunoglobulin single variable domains such as VHHs. CTLA4-binding protein of the invention may, in addition to the CTLA4-binding immunoglobulin single variable domains, comprise linkers and/or moieties with effector functions, e.g. half-life-extending moieties like albumin-binding immunoglobulin single variable domains, and/or a fusion partner like serum albumin and/or an attached polymer like PEG and/or an Fc region. In some embodiments, CTLA4-binding protein of the invention also encompasses bi-specific antibody, which contains immunoglobulin single variable domains that bind to different antigens.

Typically, the CTLA4-binding protein of the invention will bind to the antigen (i.e., CTLA4) with a dissociation constant (KD) of preferably $10^{-7}$ to $10^{-10}$ moles/liter (M), more preferably 10-8 to $10^{-10}$ moles/liter, even more preferably $10^{-9}$ to $10^{-10}$ moles/liter, or less (as measured in a Biacore or in a KinExA or in a Fortibio assay), and/or with an association constant (KA) of at least $10^7$ $M^{-1}$, preferably at least $10^8$ $M^{-1}$, more preferably at least $10^9$ $M^{-1}$, more preferably at least $10^{10}$ $M^{-1}$. Any KD value greater than $10^{-4}$ M is generally considered to indicate non-specific binding. Specific binding of an antigen-binding protein to an antigen or epitope can be determined in any suitable manner known per se, including, for example, the assays described herein, Scatchard analysis and/or competitive binding assays, such as radioimmunoassays (RIA), enzyme immunoassays (EIA) and sandwich competition assays.

Amino acid residues will be indicated according to the standard three-letter or one-letter amino acid code, as generally known and agreed upon in the art. When comparing two amino acid sequences, the term "amino acid difference" refers to insertions, deletions or substitutions of the indicated number of amino acid residues at a position of the reference sequence, compared to a second sequence. In case of substitution(s), such substitution(s) will preferably be conservative amino acid substitution(s), which means that an amino acid residue is replaced with another amino acid residue of similar chemical structure and which has little or essentially no influence on the function, activity or other biological properties of the polypeptide. Such conservative amino acid substitutions are well known in the art, wherein conservative amino acid substitutions preferably are substitutions in which one amino acid within the following groups (i)-(v) is substituted by another amino acid residue within the same group: (i) small aliphatic, nonpolar or slightly polar residues: Ala, Ser, Thr, Pro and Gly; (ii) polar, negatively charged residues and their (uncharged) amides: Asp, Asn, Glu and Gln; (iii) polar, positively charged residues: His, Arg and Lys; (iv) large aliphatic, nonpolar residues: Met, Leu, Ile, Val and Cys; and (v) aromatic residues: Phe, Tyr and Trp. Particularly preferred conservative amino acid substitutions are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp or into Phe; Val into Ile or into Leu.

"Sequence identity" between two polypeptide sequences indicates the percentage of amino acids that are identical between the sequences. "Sequence similarity" indicates the percentage of amino acids that either are identical or that represent conservative amino acid substitutions. Methods for evaluating the level of sequence identity between amino acid or nucleotide sequences are known in the art. For example, sequence analysis softwares are often used to determine the identity of amino acid sequences. For example, identity can be determined by using the BLAST program at NCBI database. For determination of sequence identity, see e.g., *Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987 and *Sequence Analysis Primer*, Gribskov, M. and Devereux, J., eds., M Stockton Press, New York, 1991.

A polypeptide or nucleic acid molecule is considered to be "essentially isolated"—for example, when compared to its native biological source and/or the reaction medium or cultivation medium from which it has been obtained—when it has been separated from at least one other component with which it is usually associated in said source or medium, such as another protein/polypeptide, another nucleic acid, another biological component or macromolecule or at least one contaminant, impurity or minor component. In particular, a polypeptide or nucleic acid molecule is considered "essentially isolated" when it has been purified at least 2-fold, in particular at least 10-fold, more in particular at least 100-fold, and up to 1000-fold or more. A polypeptide or nucleic acid molecule that is "in essentially isolated form" is preferably essentially homogeneous, as determined using a suitable technique, such as a suitable chromatographical technique, such as polyacrylamide gel electrophoresis.

An "affinity-matured" anti-CTLA4 antibody, in particular a VHH or a domain antibody, has one or more alterations in one or more CDRs which result in an improved affinity for CTLA4, as compared to the respective parent CTLA4-binding molecule. Affinity-matured CTLA4-binding molecules of the invention may be prepared by methods known in the art, for example, as described by Marks et al., 1992, Biotechnology 10:779-783, or Barbas, et al., 1994, Proc. Nat. Acad. Sci, USA 91: 3809-3813; Shier et al., 1995, Gene 169:147-155; Yelton et al., 1995, Immunol. 155: 1994-2004; Jackson et al., 1995, J. Immunol. 154(7):3310-9; and Hawkins et al., 1992, J. Mol. Biol. 226(3): 889 896; KS Johnson and RE Hawkins, "Affinity maturation of antibodies using phage display", Oxford University Press 1996.

As used herein, the term "subject" refers to mammalian, especially primate, in particular human.

CTLA4 Binding Protein of the Invention

In a first aspect, the invention provides a CTLA4-binding protein, which comprises at least one immunoglobulin single variable domain that can specifically bind to CTLA4. In some embodiments, said CTLA4-binding molecule comprises one immunoglobulin single variable domain that specifically binds to CTLA4. In some embodiments, said CTLA4-binding molecule comprises two, three, four or more immunoglobulin single variable domains that specifically bind to CTLA4. In some embodiments, said CTLA4-binding protein comprises two or more identical immunoglobulin single variable domains that specifically bind to CTLA4. In other embodiments, said CTLA4 binding protein comprises two or more different immunoglobulin single variable domains that specifically bind to CTLA4. In some embodiments, said two or more immunoglobulin single variable domains that specifically bind to CTLA4 are directly linked to each other. In some embodiments, said two or more immunoglobulin single variable domains that specifically bind to CTLA4 are linked to each other by a linker. Said linker may be a non-functional amino acid sequence having a length of 1-20 or more amino acids and no secondary or higher structure. For example, said linker is a flexible linker such as GGGGS, GS, GAP, (GGGGS)×3, and the like.

In some embodiments, said at least one immunoglobulin single variable domain comprises the CDR1, CDR2 and CDR3 selected from:

(1) CDR1 set forth in SEQ ID NO:1, CDR2 set forth in SEQ ID NO:2, CDR3 set forth in SEQ ID NO:3 (corresponding to CDRs of antibody No. 116);

(2) CDR1 set forth in SEQ ID NO:4, CDR2 set forth in SEQ ID NO:5, CDR3 set forth in SEQ ID NO:6 (corresponding to CDRs of antibody No. 119);

(3) CDR1 set forth in SEQ ID NO:7, CDR2 set forth in SEQ ID NO:8, CDR3 set forth in SEQ ID NO:9 (corresponding to CDRs of antibody No. 128);

(4) CDR1 set forth in SEQ ID NO:10, CDR2 set forth in SEQ ID NO:11, CDR3 set forth in SEQ ID NO:12 (corresponding to CDRs of antibody No. 138);

(5) CDR1 set forth in SEQ ID NO:13, CDR2 set forth in SEQ ID NO:14, CDR3 set forth in SEQ ID NO:15 (corresponding to CDRs of antibody No. 145);

(6) CDR1 set forth in SEQ ID NO:16, CDR2 set forth in SEQ ID NO:17, CDR3 set forth in SEQ ID NO:18 (corresponding to CDRs of antibody No. 155);

(7) CDR1 set forth in SEQ ID NO:19, CDR2 set forth in SEQ ID NO:20, CDR3 set forth in SEQ ID NO:21 (corresponding to CDRs of antibody No. 165);

(8) CDR1 set forth in SEQ ID NO:22, CDR2 set forth in SEQ ID NO:23, CDR3 set forth in SEQ ID NO:24 (corresponding to CDRs of antibody No. 188);

(9) CDR1 set forth in SEQ ID NO:25, CDR2 set forth in SEQ ID NO:26, CDR3 set forth in SEQ ID NO:27 (corresponding to CDRs of antibody No. C1);

(10) CDR1 set forth in SEQ ID NO:28, CDR2 set forth in SEQ ID NO:29, CDR3 set forth in SEQ ID NO:30 (corresponding to CDRs of antibody No. C2);

(11) CDR1 set forth in SEQ ID NO:31, CDR2 set forth in SEQ ID NO:32, CDR3 set forth in SEQ ID NO:33 (corresponding to CDRs of antibody No. C16);

(12) CDR1 set forth in SEQ ID NO:34, CDR2 set forth in SEQ ID NO:35, CDR3 set forth in SEQ ID NO:36 (corresponding to CDRs of antibody No. C22);

(13) CDR1 set forth in SEQ ID NO:37, CDR2 set forth in SEQ ID NO:38, CDR3 set forth in SEQ ID NO:39 (corresponding to CDRs of antibody No. C27);

(14) CDR1 set forth in SEQ ID NO:40, CDR2 set forth in SEQ ID NO:41, CDR3 set forth in SEQ ID NO:42 (corresponding to CDRs of antibody No. C29);

(15) CDR1 set forth in SEQ ID NO:43, CDR2 set forth in SEQ ID NO:44, CDR3 set forth in SEQ ID NO:45 (corresponding to CDRs of antibody No. C38);

(16) CDR1 set forth in SEQ ID NO:46, CDR2 set forth in SEQ ID NO:47, CDR3 set forth in SEQ ID NO:48 (corresponding to CDRs of antibody No. J5);

(17) CDR1 set forth in SEQ ID NO:49, CDR2 set forth in SEQ ID NO:50, CDR3 set forth in SEQ ID NO:51 (corresponding to CDRs of antibody No. J17);

(18) CDR1 set forth in SEQ ID NO:52, CDR2 set forth in SEQ ID NO:53, CDR3 set forth in SEQ ID NO:54 (corresponding to CDRs of antibody No. J29);

(19) CDR1 set forth in SEQ ID NO:55, CDR2 set forth in SEQ ID NO:56, CDR3 set forth in SEQ ID NO:57 (corresponding to CDRs of antibody No. J35);

(20) CDR1 set forth in SEQ ID NO:58, CDR2 set forth in SEQ ID NO:59, CDR3 set forth in SEQ ID NO:60 (corresponding to CDRs of antibody No. J37);

(21) CDR1 set forth in SEQ ID NO:61, CDR2 set forth in SEQ ID NO:62, CDR3 set forth in SEQ ID NO:63 (corresponding to CDRs of antibody No. J38);

(22) CDR1 set forth in SEQ ID NO:64, CDR2 set forth in SEQ ID NO:65, CDR3 set forth in SEQ ID NO:66 (corresponding to CDRs of antibody No. J39);

(23) CDR1 set forth in SEQ ID NO:67, CDR2 set forth in SEQ ID NO:68, CDR3 set forth in SEQ ID NO:69 (corresponding to CDRs of antibody No. J42);

(24) CDR1 set forth in SEQ ID NO:70, CDR2 set forth in SEQ ID NO:71, CDR3 set forth in SEQ ID NO:72 (corresponding to CDRs of antibody No. J69); and

(25) CDR1 set forth in SEQ ID NO:73, CDR2 set forth in SEQ ID NO:74, CDR3 set forth in SEQ ID NO:75 (corresponding to CDRs of antibody No. J78).

In some embodiments, said at least one immunoglobulin single variable domain of the CTLA4-binding protein of the invention is VHH. In some specific embodiments, said VHH comprises an amino acid sequence of any one of SEQ ID NOs:76-100. In some other embodiments, said VHH is a humanized VHH. Said humanized VHH comprises an amino acid sequence having at least 80%, preferably at least 90%, more preferably at least 95%, even more preferably at least 99% sequence identity to any one of SEQ ID NOs: 76-100. Alternatively, the amino acid sequence of said VHH contains one or more amino acid substitutions, preferably conservative amino acid substitutions, compared with any one of SEQ ID NOs: 76-100. For example, said VHH contains 1, 2, 3, 4, 5, 6, 7, 8, 9 or 10 conservative amino acid substitutions. In some specific embodiments, said humanized VHH comprises an amino acid sequence of any one of SEQ ID NOs:101-109.

In some embodiments, the CTLA4-binding protein of the invention is obtained by affinity maturation. The CTLA4-binding protein obtained by affinity maturation may have one or more alterations in one or more CDRs, such alterations result in an increased affinity to CTLA4 when compared with parent CTLA4-binding protein.

In some embodiments, the CTLA4-binding protein of the invention, in addition to the at least one immunoglobulin single variable domain that can specifically bind to CTLA4, further comprises an immunoglobulin Fc region. Inclusion of an immunoglobulin Fc region in the CTLA4-binding protein of the invention allows the binding protein to form dimmers, and also allows extension of the in vivo half-life of said binding protein. Fc region that can be used in the invention may be derived from immunoglobulins of different subtypes, such as IgG (e.g, IgG1, IgG2, IgG3 or IgG4 subtype), IgA1, IgA2, IgD, IgE or IgM. The immunoglobulin Fc region generally includes a hinge region or a portion of the hinge region, the CH2 region, and the CH3 region of the immunoglobulin constant region.

In some embodiments, mutations can be introduced into wildtype Fc sequence for altering relevant activities mediated by Fc. Said mutations include, but not limited to, a) mutations altering CDC activity mediated by Fc; b) mutations altering ADCC activity mediated by Fc; or c) mutations altering in vivo half-life mediated by FcRn. Such mutation are described in Leonard G Presta, Current Opinion in Immunology 2008, 20:460-470; Esohe E. Idusogie et al., J Immunol 2000, 164: 4178-4184; RAPHAEL A. CLYNES et al., Nature Medicine, 2000, Volume 6, Number 4: 443-446; Paul R. Hinton et al., J Immunol, 2006, 176:346-356. For example, Fc-mediated ADCC or CDC activity can be increased or removed, or FcRn Affinity can be enhanced or attenuated by mutating 1, 2, 3, 4, 5, 6, 7, 8, 9, or 10 amino acids on the CH2 region. In addition, protein stability can be increased by mutating 1, 2, 3, 4, 5, 6, 7, 8, 9 or 10 amino acids of the hinge region.

In some embodiments, mutations may be introduced into the Fc sequence such that the mutated Fc tends to form homo-dimmers or hetero-dimmers more readily. For example, Ridgway, Presta et al. 1996 and Carter 2001 mentioned using the knob-hole model of the spatial interaction of amino acid side chain groups on Fc contacting interface to allow different Fc mutants to form hetero-dimmers more readily; in addition, CN 102558355A or CN 103388013A discloses to allow different Fc mutants to form hetero-dimmers more readily (CN 102558355A), or Fes with same mutations to form homo-dimmers more readily (CN 103388013A), by changing the charges of the amino acids on Fc contacting interface which in turn changes the ionic interaction at the Fc contacting interface.

Preferably, said immunoglobulin Fc region is an Fc region of human immunoglobulin, more preferably an Fc region of human IgG1. In some specific embodiments, the amino acid sequence of the immunoglobulin Fc region is set forth in SEQ ID NO:132. In some embodiments, the N-terminal EPKSC in SEQ ID NO: 132 can be deleted or mutated to EPKSS or MDPKSS.

In some embodiments, in the CTLA4-binding protein of the invention, the immunoglobulin single variable domain capable of specifically binding to CTLA4 is linked to the immunoglobulin Fc region via a linker. Said linker may be a non-functional amino acid sequence of 1-20 or more amino acids in length, without secondary or higher structure. For example, the linker is a flexible joint such as GGGGS, GS, GAP, and the like.

In some embodiments, the CTLA4-binding protein of the invention comprises one immunoglobulin single variable domain that specifically binds to CTLA4, which is linked directly or via a linker to an immunoglobulin Fc region, said immunoglobulin Fc region allows said CTLA4-binding protein to form a dimeric molecule comprising two CTLA4-binding domains. Such a CTLA4-binding protein is also referred to as a bivalent CTLA4-binding protein. In some embodiments, the dimmer is a homo-dimmer.

In some embodiments, a CTLA4-binding protein of the invention comprises two immunoglobulin single variable domains that specifically bind to CTLA4 and an immunoglobulin Fc region, which are linked directly or via a linker, said immunoglobulin Fc region allows the CTLA4-binding protein to form a dimeric molecule comprising four CTLA4-binding domains. Such a CTLA4-binding protein is also referred to as a tetravalent CTLA4-binding protein. In some embodiments, the dimmer is a homo-dimmer.

In some preferred embodiments, the CTLA4-binding protein of the invention comprising an immunoglobulin Fc region comprises an amino acid sequence selected from SEQ ID NO:114-128.

In another aspect, the CTLA4-binding protein of the invention also encompasses an anti-CTLA4 antibody molecule that binds to the same epitope as a VHH consisting of the amino acid sequence of any one of SEQ ID NOs:76-100.

The CTLA4-binding protein of the invention has at least one of the following features:
(a) binding to human CTLA4 with a KD of less than $1 \times 10^{-7}$ M;
(b) blocking the interaction of CTLA4 with CD80 and/or CD86;
(c) enhancing activation of PBMCs and/or T cells;
(d) inhibiting tumor growth.

The CTLA4-binding protein of the invention may bind to CTLA4 with a KD of less than $1 \times 10^{-7}$ M, preferably less than $1 \times 10^{-8}$ M, more preferably less than $1 \times 10^{-9}$ M, more preferably less than $1 \times 10^{-10}$ M.

In some embodiments, the CTLA4-binding protein of the invention can specifically bind to human CTLA4 and block the interaction of CTLA4 with CD80, and/or interaction of CTLA4 with CD80 and/or CD86.

The CTLA4-binding protein of the invention can inhibit tumor growth by at least about 10%, preferably at least about 20%, more preferably at least about 30%, more preferably at least about 40%, more preferably at least about 50%, more preferably at least about 60%, more preferably at least about 70%, and more preferably at least about 80%.

Furthermore, the CTLA4-binding protein of the invention is resistant to heat treatment. For example, no significant aggregation or degradation can be observed after treatment at 40° C. for up to 30 days.

Finally, the CTLA4-binding protein of the invention shows better tolerance in cynomolgus monkeys. For example, up to 30 mg/kg of the administered dose, no drug-related adverse reactions can be observed.

Nucleic Acid, Vector and Host Cell

In another aspect, the invention relates to a nucleic acid molecule that encodes the CTLA4-binding proteins of the invention. The nucleic acid of the invention may be RNA, DNA or cDNA. According to one embodiment of the invention, the nucleic acid of the invention is in essentially isolated form.

The nucleic acid of the invention may also be in the form of, may be present in and/or may be part of a vector, such as for example a plasmid, cosmid or YAC. The vector may especially be an expression vector, i.e. a vector that can provide for expression of the CTLA4-binding protein in vitro and/or in vivo (i.e. in a suitable host cell, host organism and/or expression system). Such expression vector generally comprises at least one nucleic acid of the invention that is operably linked to one or more suitable regulatory elements, such as promoter(s), enhancer(s), terminator(s), and the like. Such elements and their selection in view of expression of a specific sequence in a specific host are common knowledge of the skilled person. Specific examples of regulatory elements and other elements useful or necessary for expressing CTLA4-binding protein of the invention include such as promoters, enhancers, terminators, integration factors, selection markers, leader sequences, reporter genes, and the like.

The nucleic acids of the invention may be prepared or obtained in a manner known per se (e.g. by automated DNA synthesis and/or recombinant DNA technology), based on the information on the amino acid sequences for the polypeptides of the invention given herein, and/or can be isolated from a suitable natural source.

In another aspect, the invention relates to recombination host cells that express or are capable of expressing one or more CTLA4-binding protein of the invention; and/or that contain a nucleic acid of the invention. According to a particularly preferred embodiment, said host cells are bacterial cells; other useful cells are yeast cells, fungal cells or mammalian cells.

Suitable bacterial cells include cells from gram-negative bacterial strains such as strains of *Escherichia coli, Proteus*, and *Pseudomonas*, and gram-positive bacterial strains such as strains of *Bacillus, Streptomyces, Staphylococcus*, and *Lactococcus*. Suitable fungal cell include cells from species of *Trichoderma, Neurospora*, and *Aspergillus*.

Suitable fungal cell include cells from species of *Trichoderma, Neurospora*, and *Aspergillus*. Suitable yeast cells include cells from species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), and *Hansenula*.

Suitable mammalian cells include for example HEK293 cells, CHO cells, BHK cells, HeLa cells, COS cells, and the like.

However, amphibian cells, insect cells, plant cells, and any other cells used in the art for the expression of heterologous proteins can be used as well.

The invention further provides methods of manufacturing a CTLA4-binding protein of the invention, such methods generally comprise the steps of:
culturing host cells of the invention under conditions that allow expression of the CTLA4-binding protein of the invention; and
recovering the CTLA4-binding protein expressed by the host cells from the culture; and
optionally further purifying and/or modifying the CTLA4-binding protein of the invention.

CTLA4-binding proteins of the invention may be produced in a cell as set out above either intracellularly (e.g. in the cytosol, in the periplasma or in inclusion bodies) and then isolated from the host cells and optionally further purified; or they can be produced extracellularly (e.g. in the medium in which the host cells are cultured) and then isolated from the culture medium and optionally further purified.

Methods and reagents used for the recombinant production of polypeptides, such as specific suitable expression vectors, transformation or transfection methods, selection markers, methods of induction of protein expression, culture conditions, and the like, are known in the art. Similarly, protein isolation and purification techniques useful in a method of manufacture of a CTLA4-binding protein of the invention are well known to the skilled person.

However, the CTLA4-binding proteins of the invention can also be obtained by other methods for production of proteins known in the art, such as, chemical synthesis, including solid phase or liquid phase synthesis.

Pharmaceutical Compositions

In another aspect, the present invention provides a composition, e.g., a pharmaceutical composition, containing one or a combination of CTLA4-binding protein of the present invention, formulated together with a pharmaceutically acceptable carrier. Such compositions may include one or a combination of (e.g., two or more different) CTLA4-binding proteins of the invention. For example, a pharmaceutical composition of the invention can comprise a combination of antibody molecules that bind to different epitopes on the target antigen.

Pharmaceutical compositions of the invention also can be administered in combination therapy, i.e., combined with other agents. For example, the combination therapy can include a CTLA4-binding protein of the present invention combined with at least one other anti-tumor agent. For example, CTLA4-binding protein of the invention may be administered in combination with antibodies targeting other tumor-specific antigens. Said antibodies targeting other tumor-specific antigens include, but are not limited to anti-EGFR antibody, anti-EGFR variant antibody, anti-VEGFa antibody, anti-HER2 antibody, or anti-CMET antibody. Preferably, said antibodies are monoclonal. CTLA4-binding protein of the present invention can also be used in combination with other tumor immunotherapy means or tumor-targeting small molecule drugs. The other tumor immunotherapy means include, but are not limited to, therapeutic antibodies against tumor immunomodulatory molecules such as OX40, PDL1/PD1, CD137, etc., or CAR-T treatment means and the like.

Pharmaceutical composition of the present invention can also be used in combination with other tumor treatment means such as radiotherapy, chemotherapy, surgery, or the like, or be used before or after radiotherapy, chemotherapy, or surgery.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, or immunoconjugate, may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects (see e.g., Berge, S. M., et al. (1977) J. Pharm. Sci. 66:1-19). Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

These compositions may also contain adjuvants such as preservatives, wetting agents, emulsifying agents and dispersing agents.

Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Sterile injectable solutions can be prepared by incorporating the active compound in the required amount in an appropriate solvent with one or a combination of ingredients enumerated above, as required, followed by sterilization microfiltration. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of the antibody molecule, the dosage ranges from about 0.0001 to 100 mg/kg, and more usually 0.01 to 20 mg/kg, of the subject body weight. For example dosages can be 0.3 mg/kg body weight, 1 mg/kg body weight, 3 mg/kg body weight, 5 mg/kg body weight, 10 mg/kg body weight, 20 mg/kg body weight or 30 mg/kg body weight or within the range of 1-30 mg/kg. An exemplary treatment regime entails administration once per week, once every two weeks, once every three weeks, once every four weeks, once a month, once every 3 months or once every three to 6 months, or with a short administration interval at the beginning (such as once per week to once every three weeks), and then an extended interval later (such as once a month to once every three to 6 months).

Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A "therapeutically effective amount" of a CTLA4-binding protein of the invention preferably results in a decrease in severity of disease symptoms, an increase in frequency and duration of disease symptom-free periods, or a prevention of impairment or disability due to the disease affliction. For example, for the treatment of CTLA4 relating tumors, a "therapeutically effective amount" preferably inhibits cell growth or tumor growth by at least about 10%, at least about 20%, more preferably by at least about 40%, even more preferably by at least about 60%, and still more preferably by at least about 80% relative to untreated subjects. The ability to inhibit tumor growth can be evaluated in an animal model system predictive of efficacy in human tumors. Alternatively, this property of a composition can be evaluated by examining the ability of the compound to inhibit cell growth; such inhibition can be determined in vitro by assays known to the skilled practitioner. A therapeutically effective amount of a therapeutic compound can decrease tumor size, or otherwise ameliorate symptoms in a subject, for example, to achieve or prolong the progression-free survival of cancer patients, prolong the overall survival of cancer patients. One of ordinary skill in the art would be able to determine such amounts based on such factors as the subject's size, the severity of the subject's symptoms, and the particular composition or route of administration selected. Furthermore, one skilled in the art can also determine the effective amount of a CTLA4-binding protein of the invention by examining the ability to activate T cells in vitro.

A composition of the present invention can be administered via one or more routes of administration using one or more of a variety of methods known in the art. As will be appreciated by the skilled artisan, the route and/or mode of administration will vary depending upon the desired results. Preferred routes of administration for CTLA4-binding proteins of the invention include intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, a CTLA4-binding protein of the invention can be administered via a non-parenteral route, such as a topical, epidermal or mucosal route of administration, for example, intranasally, orally, vaginally, rectally, sublingually or topically.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compositions can be administered with medical devices known in the art. For example, in a preferred embodiment, a therapeutic composition of the invention can be administered with a needleless hypodermic injection device, such as the devices disclosed in U.S. Pat. Nos. 5,399,163; 5,383,851; 5,312,335; 5,064,413; 4,941,880; 4,790,824; or 4,596,556. Examples of well-known implants and modules useful in the present invention include: U.S.

Pat. No. 4,487,603, which discloses an implantable microinfusion pump for dispensing medication at a controlled rate; U.S. Pat. No. 4,486,194, which discloses a therapeutic device for administering medicaments through the skin; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments; and U.S. Pat. No. 4,475,196, which discloses an osmotic drug delivery system. These patents are incorporated herein by reference. Many other such implants, delivery systems, and modules are known to those skilled in the art.

In certain embodiments, the CTLA4-binding proteins of the invention can be formulated to ensure proper distribution in vivo. For example, the blood-brain barrier (BBB) excludes many highly hydrophilic compounds. To ensure that the therapeutic compounds of the invention cross the BBB (if desired), they can be formulated, for example, in liposomes. For methods of manufacturing liposomes, see, e.g., U.S. Pat. Nos. 4,522,811; 5,374,548; and 5,399,331. The liposomes may comprise one or more moieties which are selectively transported into specific cells or organs, thus enhance targeted drug delivery (see, e.g., V. V. Ranade (1989) J. Clin. Pharmacol. 29:685). Exemplary targeting moieties include folate or biotin (see, e.g., U.S. Pat. No. 5,416,016 to Low et al); mannosides (Umezawa et al., (1988) Biochem. Biophys. Res. Commun. 153:1038): antibodies (P. G. Bloeman et al. (1995) FEBS Lett. 357:140; M. Owais et al. (1995) Antimicrob. Agents Chemother. 39:180); surfactant protein A receptor (Briscoe et al. (1995) Am. J. Physiol. 1233: 134); p120 (Schreier et al. (1994) J Biol. Chem. 269:9090): see also K. Keinanen; M. L. Laukkanen (1994) FEBS Lett. 346:123; J J. Killion; L J. Fidler (1994) Immunomethods 4:273.

Preventing and Treating of Diseases

In another aspect, the present invention provides the use of the CTLA4 binding protein, nucleic acid, host cell and pharmaceutical composition of the invention for preventing and/or treating CTLA4 relating diseases, as well as the corresponding methods. CTLA4 relating diseases that can be prevented and/or treated with the CTLA4-binding protein of the invention are described in detailed as follows.

Cancer

Blocking CTLA4 by CTLA4-binding protein of the invention can enhance the immune response to cancerous cells in the patient. A CTLA4-binding protein of the invention may be used alone to inhibit the growth of cancerous tumors. Or as described below, a CTLA4-binding protein of the invention may be used in conjunction with other antitumor therapies, for example, in conjunction with other immunogenic agents, standard cancer treatments, or other antibodies molecule.

Accordingly, in one embodiment, the invention provides a method of preventing and/or treating cancer in a subject, comprising administering to the subject a therapeutically effective amount of CTLA4-binding protein of the invention so as to inhibit growth of tumor cells in the subject.

Preferred cancers which may be prevented and/or treated using the CTLA4-binding protein of the invention include cancers typically responsive to immunotherapy. Non-limiting examples of preferred cancers for treatment include lung cancer, ovarian cancer, colon cancer, rectal cancer, melanoma (e.g., metastatic malignant melanoma), renal cancer, bladder cancer, breast cancer, liver cancer, lymphoma, hematological malignancy, head and neck cancer, glioma, gastric cancer, nasopharyngeal cancer, laryngeal cancer, cervical cancer, corpus carcinoma, osteosarcoma. Examples of other cancers that may be treated using the methods of the invention include bone cancer, pancreatic cancer, prostatic cancer, skin cancer, cancer of the head or neck, cutaneous or intraocular malignant melanoma, uterine cancer, cancer of the anal region, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

Optionally, CTLA4-binding protein of the invention can be combined with an immunogenic agent, such as cancerous cells, purified tumor antigens (including recombinant proteins, peptides, and carbohydrate molecules), cells, and cells transfected with genes encoding immune stimulating cytokines (He et al. (2004) J. Immunol. 173:4919-28). Non-limiting examples of tumor vaccines that can be used include peptides of melanoma antigens, such as peptides of gp100, MAGE antigens, Trp-2, MART1 and/or tyrosinase, or tumor cells transfected to express the cytokine GM-CSF.

In humans, some tumors have been shown to be immunogenic such as melanomas. It is anticipated that by raising the threshold of T cell activation by CTLA4 blockade with CTLA4-binding protein of the invention, it is possible to activate tumor responses in the host. CTLA4 blockade (such as CTLA4 antibody, e.g., the CTLA4-binding protein of the invention) is likely to be most effective when combined with a vaccination protocol. Many experimental strategies for vaccination against tumors have been devised (see Rosenberg, S., 2000, Development of Cancer Vaccines, ASCO Educational Book Spring: 60-62; Logothetis, C, 2000, ASCO Educational Book Spring: 300-302; Khayat, D. 2000, ASCO Educational Book Spring: 414-428; Foon, K. 2000, ASCO Educational Book Spring: 730-738; see also Restifo, N. and Sznol, M., Cancer Vaccines, Ch. 61, pp. 3023-3043 in DeVita, V. et al. (eds.), 1997, Cancer: Principles and Practice of Oncology. Fifth Edition). In one of these strategies, a vaccine is prepared using autologous or allogeneic tumor cells. These cellular vaccines have been shown to be most effective when the tumor cells are transduced to express GM-CSF. GM-CSF has been shown to be a potent activator of antigen presentation for tumor vaccination (Dranoff et al. (1993) Proc. Natl. Acad. Sd U.S.A. 90: 3539-43).

The study of gene expression and large scale gene expression patterns in various tumors has led to the definition of so-called tumor specific antigens (Rosenberg, SA (1999) Immunity 10: 281-7). In many cases, these tumor specific antigens are differentiation antigens expressed in the tumors and in the cell from which the tumor arose, for example melanocyte antigens gp100, MAGE antigens, and Trp-2. More importantly, many of these antigens can be shown to be the targets of tumor specific T cells found in the host.

CTLA4-binding protein of the invention may be used in conjunction with a collection of recombinant proteins and/or peptides expressed in a tumor in order to generate an immune response to these proteins. These proteins are normally viewed by the immune system as self-antigens and are therefore tolerant to them. The tumor antigen may also include the protein telomerase, which is required for the synthesis of telomeres of chromosomes and which is expressed in more than 85% of human cancers and in only a limited number of somatic tissues (Kim, N et al. (1994) Science 266: 2011-2013). Tumor antigen may also be "neoantigens" expressed in cancer cells because of somatic mutations that alter protein sequence or create fusion proteins between two unrelated sequences (i.e. bcr-abl in the Philadelphia chromosome).

Other tumor vaccines may include the proteins from viruses implicated in human cancers such a Human Papilloma Viruses (HPV), Hepatitis Viruses (HBV and HCV) and Kaposi's Herpes Sarcoma Virus (KHSV). Another form of tumor specific antigen which may be used in conjunction with CTLA4 blockade (such as CTLA4 antibody, e.g., CTLA4-binding protein of the invention) is purified heat shock proteins (HSP) isolated from the tumor tissue itself. These heat shock proteins contain fragments of proteins from the tumor cells and these HSPs are highly efficient at delivery to antigen presenting cells for eliciting tumor immunity (Suot, R & Srivastava, P (1995) Science 269: 1585-1588; Tamura, Y. et al. (1997) Science 278:117-120).

Dendritic cells (DCs) are potent antigen presenting cells that can be used to prime antigen-specific responses. DCs can be produced ex vivo and loaded with various protein and peptide antigens as well as tumor cell extracts (Nestle, F. et al. (1998) Nature Medicine 4: 328-332). DCs may also be transduced by genetic means to express these tumor antigens as well. DCs have also been fused directly to tumor cells for the purposes of immunization (Kugler, A. et al. (2000) Nature Medicine 6:332-336). As a method of vaccination, DC immunization may be effectively combined with CTLA4 blockade (such as CTLA4 antibody, e.g., CTLA4-binding protein of the invention) to activate more potent anti-tumor responses.

CAR-T (Chimeric Antigen Receptor T-Cell Immunotherapy) is another cell therapy for treating tumors. Chimeric Antigen Receptor T-Cell (CAR-T cells) are T cells from a patient that have been genetically infected with a chimeric protein of an antigen-binding moiety of an antibody against certain tumor antigen coupled with CD3-(chain or intracellular portion of FccRIγ for expressing a chimeric antigen receptor (CAR). Also, co-stimulate signaling sequence may be introduced for increasing cytotoxic activity, proliferation and survival of T cells, and promoting the release of cytokines. After reprogramming, T cells from the patient expanded in vitro to produce a large number tumor-specific CAR-T cells which are then transfused back into the patient for treating tumor. CTLA4 blocking agents (such as CTLA4 antibodies, e.g., the CTLA4 binding protein of the invention) may be used in combination with CAR-T cell therapy for activate stronger anti-tumor response.

CTLA4-binding protein of the invention may also be combined with standard cancer treatments. CTLA4-binding protein of the invention may be effectively combined with chemotherapeutic regimes. The scientific rationale behind the combined use of CTLA4-binding protein of the invention and chemotherapy is that cell death, that is a consequence of the cytotoxic action of most chemotherapeutic compounds, should result in increased levels of tumor antigen in the antigen presentation pathway. Other combination therapies that may result in synergy with CTLA4 blockade through cell death are radiation, surgery, and hormone deprivation. Each of these protocols creates a source of tumor antigen in the host. Angiogenesis inhibitors may also be combined with CTLA4-binding protein of the invention. Inhibition of angiogenesis leads to tumor cell death which may feed tumor antigen into host antigen presentation pathways.

CTLA4 binding protein of the invention can also be used in combination with antibodies against other tumor-specific antigens. Said antibodies against other tumor-specific antigens include but are not limited to anti-EGFR antibody, anti-EGFR variant antibody, anti-VEGFa antibody, anti-HER2 antibody, or anti-CMET antibody. Preferably, said antibodies are monoclonal.

CTLA4-binding protein of the invention can also be used in combination with bispecific antibodies that target Fc alpha or Fc gamma receptor-expressing effectors cells to tumor cells (see, e.g., U.S. Pat. Nos. 5,922,845 and 5,837, 243). Bispecific antibodies can be used to target two separate antigens. For example anti-Fc receptor/anti tumor antigen (e.g., Her-2/neu) bispecific antibodies have been used to target macrophages to sites of tumor. This targeting may more effectively activate tumor specific responses. The T cell arm of these responses would be augmented by the use of CTLA4 blockade. Alternatively, antigen may be delivered directly to DCs by the use of bispecific antibodies which bind to tumor antigen and a dendritic cell specific cell surface marker.

Tumors evade host immune surveillance by a large variety of mechanisms. Many of these mechanisms may be overcome by the inactivation of proteins which are expressed by the tumors and which are immunosuppressive. These include among others TGF-beta (Kehrl, J. et al. (1986) J. Exp. Med. 163: 1037-1050), IL-10 (Howard, M. & O'Garra, A. (1992) Immunology Today 13: 198-200), and Fas ligand (Hahne, M. et al. (1996) Science 274: 1363-1365). Antibodies to each of these entities may be used in combination with CTLA4-binding protein of the invention to counteract the effects of the immunosuppressive agent and favor tumor immune responses by the host.

Other antibodies which may be used to activate host immune responsiveness can be used in combination with anti-CTLA4. Anti-CD40 antibodies are able to substitute effectively for T cell helper activity (Ridge, J. et al. (1998) Nature 393: 474-478) and can be used in conjunction with CTLA4-binding protein of the invention. Activating antibodies to T cell costimulatory molecules such as OX-40 (Weinberg, A. et al. (2000) Immunol 164: 2160-2169), 4-1BB (Melero, I. et al. (1997) Nature Medicine 3: 682-685 (1997), and ICOS (Hutloff, A. et al. (1999) Nature 397: 262-266) as well as antibodies which block the activity of negative costimulatory molecules such as CTLA-4 (e.g., U.S. Pat. No. 5,811,097) or BTLA (Watanabe, N. et al. (2003) Nat Immunol 4:670-9), B7-H4 (Sica, G L et al. (2003) Immunity 18:849-61) may also provide for increased levels of T cell activation.

Bone marrow transplantation is currently being used to treat a variety of tumors of hematopoietic origin. While graft versus host disease is a consequence of this treatment, therapeutic benefit may be obtained from graft vs. tumor responses. CTLA4 blockade can be used to increase the effectiveness of the donor engrafted tumor specific T cells. There are also several experimental treatment protocols that involve ex vivo activation and expansion of antigen specific T cells and adoptive transfer of these cells into recipients in order to antigen-specific T cells against tumor (Greenberg, R. & Riddell, S. (1999) Science 285: 546-51). These methods may also be used to activate T cell responses to infectious agents such as CMV. Ex vivo activation in the presence of CTLA4-binding protein of the invention may be expected to increase the frequency and activity of the adoptively transferred T cells.

Infectious Diseases

Other methods of the invention are used to treat patients that have been exposed to particular toxins or pathogens. Accordingly, another aspect of the invention provides a method of preventing or treating an infectious disease in a subject comprising administering to the subject a CTLA4-binding protein of the invention, such that the subject is treated for the infectious disease.

Similar to its application to tumors as discussed above, CTLA4 blockade can be used alone, or as an adjuvant, in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to HTV, Hepatitis (A, B, & C), *Influenza, Herpes, Giardia,* Malaria, *Leishmania, Staphylococcus aureus, Pseudomonas Aeruginosa*. CTLA4 blockade is particularly useful against established infections by agents such as HIV that present altered antigens over the course of the infections. These novel epitopes are recognized as foreign at the time of anti-human CTLA4 administration, thus provoking a strong T cell response that is not dampened by negative signals through CTLA4.

Some examples of pathogenic viruses causing infections treatable by methods of the invention include HIV, hepatitis (A, B, or C), herpes virus (e.g., VZV, HSV-1, HAV-6, HSV-II, and CMV, Epstein Barr virus), adenovirus, influenza virus, flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Some examples of pathogenic bacteria causing infections treatable by methods of the invention include chlamydia, rickettsial bacteria, mycobacteria, staphylococci, streptococci, pneumonococci, meningococci and conococci, klebsiella, proteus, serratia, pseudomonas, legionella, diphtheria, salmonella, bacilli, cholera, tetanus, botulism, anthrax, plague, leptospirosis, and Lyme's disease bacteria.

Some examples of pathogenic fungi causing infections treatable by methods of the invention include *Candida* (*albicans, krusei, glabrata, tropicalis,* etc.), *Cryptococcus neoformans, Aspergillus* (*fumigatus, niger,* etc.), Genus *Mucorales* (*mucor, absidia, rhizopus*), *Sporothrix schenkii, Blastomyces dermatitidis, Paracoccidioides brasiliensis, Coccidioides immitis* and *Histoplasma capsulatum*.

Some examples of pathogenic parasites causing infections treatable by methods of the invention include *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis.*

In all of the above methods, CTLA4 blockade can be combined with other forms of immunotherapy such as cytokine treatment (e.g., interferons, GM-CSF, G-CSF, IL-2), or bispecific antibody therapy, which provides for enhanced presentation of tumor antigens (see, e.g., Holliger (1993) Proc. Natl. Acad. Sci USA 90:6444-6448; Poljak (1994) Structure 2:1121-1123).

EXAMPLES

The present invention is further illustrated by the following examples, but the scope of the invention should not be limited to the specific examples in any way.

Example 1: Screen of Heavy Chain Single Domain Antibody Against CTLA4

1.1 Library Construction and Screening

CTLA4-Fc fusion protein (SEQ ID NO:129) for immunization was expressed by HEK293 cells (pCDNA4, Invitrogen, Cat V86220), purified by Protein A affinity chromatography. One *Camelus bactrianus* was chosen for immunization. After 4 immunizations, lymphocytes were isolated from 100 ml camel peripheral blood, and total RNA was extracted by RNA Extraction kit (QIAGEN). Extracted RNA was reverse transcribed into cDNA using Super-Script III FIRST STRANDSUPERMIX kit according to instructions. Nucleic acid fragments encoding heavy chain antibodies were amplified by nested PCR:

```
First round PCR:
Upstream primer:
                                    (SEQ ID NO: 110)
GTCCTGGCTGCTCTTCTACAAGGC;

Downstream primer:
                                    (SEQ ID NO: 111)
GGTACGTGCTGTTGAACTGTTCC.

Second round PCR:
PCR products from first round PCR as template,
Upstream primer:
                                    (SEQ ID NO: 112)
GATGTGCAGCTGCAGGAGTCTGGRGGAGG;

Downstream primer:
                                    (SEQ ID NO: 113)
GGACTAGTGCGGCCGCTGGAGACGGTGACCTGGGT.
```

Target heavy chain single domain antibody nucleic acid fragments were recovered and cloned into phage display vector pCDisplay-3 (Creative Biolabs, Cat: VPT4023) using endonuclease PstI and NotI (from NEB). The products were then electroporated into *E. coli* competent cell TG1, and phage display library for heavy chain single domain antibodies against CTLA4 was constructed and verified. By plating serial dilutions, library capacity was determined as about $10^8$. To determine the insertion ratio of the library, 50 clones were randomly selected for colony PCR. The results revealed an insertion ratio of more than 99%.

1.2 Panning for Heavy Chain Single Domain Antibody Against CTLA4

Multi-well plates were coated with CTLA4-Fc fusion protein and Fc protein at 5 μg/well, 4° C. overnight. On next day, after blocking with 1% skim milk at room temperature for 2 hours, 1001 phages ($8 \times 10^{11}$ tfu, from the phage display library for camel heavy chain single domain antibodies constructed in 1.1) were added, room temperature for 1 hour. Thereafter, the Fc-unbound phage was again transferred into the wells coated with CTLA4-Fc fusion protein by washing with PBST (0.05% tween 20 in PBS), room temperature for 1 hour. Phages that specifically bind to CTLA4 were dissociated with triethylammonium (100 mM), and used to infect *E. coli* TG1 in log phase, producing phages which were then purified for next round screen. The same screen was repeated for 3-4 rounds. Thereby, positive clones were enriched, achieving the purpose of selecting CTLA4 specific antibodies from the antibody library by phage display technology.

1.3 Specific Selection of Individual Positive Clones by Phage Enzyme-Linked Immunoassay (ELISA)

CTLA4 binding positive phages obtained after 3 rounds of panning were used to infect blank E. coli and plated. 96 single colonies were randomly selected for culturing, and phages were produced and purified respectively. Plates were coated with CTLA4-Fc fusion protein at 4° C. overnight; sample phages as obtained were added (blank phages as control) and incubated at room temperature for 1 hour. Primary antibody, mouse anti-HA tag antibody (Beijing Kangwei Shiji Biotech. Ltd.), was added after washes and incubated at room temperature, 1 hour for reaction. Secondary antibody, goat anti-mouse alkaline phosphatase labeled antibody (Amyject Scientific Ltd.) was added after washes and incubated at room temperature, 1 hour for reaction. Alkaline phosphatase chromogenic solution was added after washes, and absorption value was read at 405 nm wave length. When the OD of the sample well is 3 times higher than the OD of control well, the sample is determined as positive. Bacteria in the positive wells were transferred to and cultured in LB liquid medium supplemented with 100 μg/ml Ampicillin for plasmid extraction and subsequent sequencing.

The protein sequences of each clone were analyzed according to the sequence alignment software Vector NTI. Clones with the same CDR1, CDR2, and CDR3 sequences are considered as the same antibody, while clones with different CDR sequences are considered as different antibody, and those early terminated sequences were excluded. A total of 34 different antibodies were finally obtained.

Example 2 Preliminary Evaluation of Heavy Chain Single Domain Antibodies Against CTLA4

2.1 Expression of Heavy Chain Single Domain Antibodies in E. coli and Purification Thereof The coding sequences of the 34 heavy chain single domain antibodies obtained by sequencing analysis were subcloned into the expression vector PET32b (Novagen, product number: 69016-3) and the correct recombinant plasmid was transformed into expression host strain BL1 (DE3) (Tiangen Biotech, CB105-02), plated on LB solid medium containing 100 micrograms per milliliter ampicillin overnight at 37° C. Single colonies were inoculated and cultured overnight, transferred in the next day for expansion at 37° C. by shaking. When the culture reached OD value of 0.6-1, 0.5 mM IPTG was added for induction, 28° C. overnight with shaking. The next day, the bacteria were harvested by centrifugation, and lysed to obtain antibody crude extracts. Nickel ion affinity chromatography was then used to purify the antibody proteins, resulting in antibody proteins of more than 90% purity.

2.2 Specific Binding of the Candidate CTLA4 Heavy Chain Single Domain Antibody to Human CTLA4 Protein Plates were coated with CTLA4-Fc fusion protein overnight at 4° C. and 10 ng of the heavy chain single-domain antibody obtained in Example 2.1 (the control was a single domain antibody not binding to the CTLA4-Fc protein) was added to each well and allowed to react for 1 hour at room temperature. After washing, primary antibody anti-His tag antibody (purchased from Beijing Kangwei Century Biotechnology Co., Ltd.) was added and reacted for 1 hour at room temperature. After washing, a secondary goat anti-mouse horseradish peroxidase-labeled antibody (Yiqiao Shenzhou, Cat: SSA007200) was added and reacted for 1 hour at room temperature. After washing, chromogenic agent was added and the absorbance was read at 405 nm.

Plates were coated with Fc protein overnight at 4° C. and 10 ng of the heavy chain single domain antibody obtained in Example 2.1 was added to each well (control was a single domain antibody against other unrelated targets) and allowed to react for 1 hour at room temperature. After washing, an rabbit anti-human Fc antibody (purchased from Shanghai Pu Xin Biotechnology Co., Ltd.) was added and reacted for 1 hour at room temperature. After washing, goat anti-rabbit horseradish peroxidase labeled antibody (purchased from Shanghai Pu Xin Biotechnology Co., Ltd.) was added and reacted at room temperature for 1 hour. After washing, chromogenic agent was added and the absorbance was read at 405 nm.

The candidate antibody is considered as binding to the CTLA4-Fc protein when the ratio of the GD value for the CTLA4-Fc protein divided by the GD value for the blank control is greater than or equal to 4; and simultaneously, the above antibody capable of binding to CTLA4-Fc antigen protein, when the ratio of the GD value for binding to CTLA4-Fc divided by the GD value for binding Fc protein is >=5, is considered as specifically binding to the CTLA4 moiety rather than the Fc moiety.

The results showed that out of the 34 antibodies, 25 (bold in bold) could specifically bind to CTLA4 without binding to Fc. The results are shown in the following Table 1:

TABLE 1

| Antibody No. | OD (against CTLA4) | OD (against Fc) | ODa/ODb | ODa/OD blank | SEQ ID NO |
|---|---|---|---|---|---|
| C1 | 1.201 | 0.053 | 42.9 | 22.7 | 84 |
| C2 | 1.231 | 0.035 | 44.0 | 35.2 | 85 |
| C16 | 1.786 | 0.053 | 63.8 | 33.7 | 86 |
| C22 | 0.848 | 0.06 | 30.3 | 14.1 | 87 |
| C23 | 0.951 | 1.057 | 34.0 | 0.9 | |
| C24 | 0.231 | 0.114 | 8.3 | 2.0 | |
| C25 | 0.091 | 0.03 | 3.3 | 3.0 | |
| C27 | 1.31 | 0.049 | 46.8 | 26.7 | 88 |
| C29 | 1.513 | 0.085 | 54.0 | 17.8 | 89 |
| C34 | 1.022 | 0.945 | 36.5 | 1.1 | |
| C38 | 1.022 | 0.045 | 36.5 | 22.7 | 90 |
| C46 | 0.621 | 0.241 | 22.2 | 2.6 | |
| J5 | 1.21 | 0.036 | 43.2 | 33.6 | 91 |
| J17 | 1.4 | 0.046 | 50.0 | 30.4 | 92 |
| J24 | 0.032 | 0.041 | 1.1 | 0.8 | |
| J29 | 1.439 | 0.036 | 51.4 | 40.0 | 93 |
| J34 | 0.932 | 1.023 | 33.3 | 0.9 | |
| J35 | 0.823 | 0.036 | 29.4 | 22.9 | 94 |
| J37 | 1.201 | 0.034 | 42.9 | 35.3 | 95 |
| J38 | 1.031 | 0.752 | 36.8 | 1.4 | 96 |
| J39 | 1.747 | 0.042 | 62.4 | 41.6 | 97 |
| J41 | 0.055 | 0.064 | 2.0 | 0.9 | |
| J42 | 1.086 | 0.045 | 38.8 | 24.1 | 98 |
| J47 | 0.062 | 0.041 | 2.2 | 1.5 | |
| J69 | 0.635 | 0.037 | 22.7 | 17.2 | 99 |
| J78 | 0.632 | 0.121 | 22.6 | 5.2 | 100 |
| 116 | 0.234 | 0.046 | 8.4 | 5.1 | 76 |
| 119 | 0.537 | 0.037 | 19.2 | 14.5 | 77 |
| 128 | 1.268 | 0.036 | 45.3 | 35.2 | 78 |
| 138 | 1.843 | 0.041 | 65.8 | 45.0 | 79 |
| 145 | 1.487 | 0.065 | 53.1 | 22.9 | 80 |
| 155 | 1.724 | 0.051 | 61.6 | 33.8 | 81 |
| 165 | 1.214 | 0.051 | 43.4 | 23.8 | 82 |
| 188 | 0.945 | 1.021 | 33.8 | 0.9 | 83 |
| Blank | 0.028 | 0.035 | 0.8 | 0.8 | |

2.3 Examination of the Blocking Effect of CTLA4 Heavy Chain Single-Domain Antibody to the Interaction Between CD80 and CTLA4 by Competitive ELISA CTLA4-Fc protein and CD80-Fc protein (SEQ ID NO: 130) were obtained by expression in HEK293 cells (pCDNA4, Invitrogen, Cat V86220). Biotinylated protein CD80-Fc-Biotin was obtained using the Thermo Biotinlytion kit.

The plates were coated overnight at 4° C. with CTLA4-Fc fusion protein at 0.5 µg/well followed by addition for each well of 500 ng of the heavy chain single domain antibody that specifically binds to CTLA4 confirmed in Example 2.2 (controls are single domain antibodies against other unrelated targets or simply buffer) and 25 ng of CD80-Fc-Biotin (no antibody or protein was added to the blank group, only an equal volume of buffer was added), and allowed to react for 1 hour at room temperature. SA-HRP (purchased from Sigma) was added and allowed to react for 1 hour at room temperature. After adding chromogenic solution, absorbance was read at 405 nm wavelength. When the sample OD value relative to the control OD value is <0.8, the antibody is considered as possessing blocking effect.

As shown in Table 2, the antibody No. C1, C16, C27, J37, J42, 128, 145, 155, 165 showed a blocking effect on the CD80/CTLA4 interaction.

TABLE 2

| Sample | OD |
| --- | --- |
| Control 1 | 2.453 |
| Control 2 | 2.391 |
| blank | 0.016 |
| C1 | 0.054 |
| C16 | 1.893 |
| C2 | 2.517 |
| C22 | 2.474 |
| C27 | 0.04 |
| C29 | 2.431 |
| C38 | 2.284 |
| J17 | 2.528 |
| J29 | 2.502 |
| J35 | 2.57 |
| J37 | 1.061 |
| J38 | 2.357 |
| J39 | 2.133 |
| J42 | 0.94 |
| J5 | 2.504 |
| J69 | 2.343 |
| J78 | 2.413 |
| 116 | 2.579 |
| 119 | 2.534 |
| 128 | 0.893 |
| 138 | 1.918 |
| 145 | 0.597 |
| 155 | 0.746 |
| 165 | 1.838 |
| 188 | 2.633 |

2.4 Binding of CTLA4 Heavy Chain Single Domain Antibody to Mouse CTLA4 Protein

Mouse CTLA4-Fc protein (SEQ ID NO: 131) was obtained by expression in HEK293 cells (pCDNA4, Invitrogen, Cat V86220). Biotinylated protein mCTLA4-Fc-Biotin was obtained using the Thermo Biotinlytion kit.

The plates were coated with the heavy chain single domain antibody obtained in Example 2.1 (control group is a single domain antibody against other unrelated target), that is, four antibodies 145, 155, C1 and C27 with better blocking effect selected according to the results of Example 2.3, at 0.5 µg/well overnight at 4° C., and 100 µg of mouse CTLA4-Fc fusion protein was added to each well and reacted for 1.5 hours at room temperature. Thereafter, SA-HRP (purchased from Sigma) was added, and the mixture was reacted at room temperature for 1.5 hours. After washing, chromogenic agent was added and the absorbance was read at 405 nm. The results are shown in Table 3.

TABLE 3

| Antibody No. | OD (against mouse CTLA4) |
| --- | --- |
| 145 | 0.026 |
| 155 | 0.032 |
| C1 | 0.042 |
| C27 | 0.021 |
| Control | 0.026 |
| blank | 0.027 |

It can be seen that the heavy chain single domain antibody of human CTLA4 of the present invention does not bind to the mouse CTLA4-Fc protein.

Figure 1B:
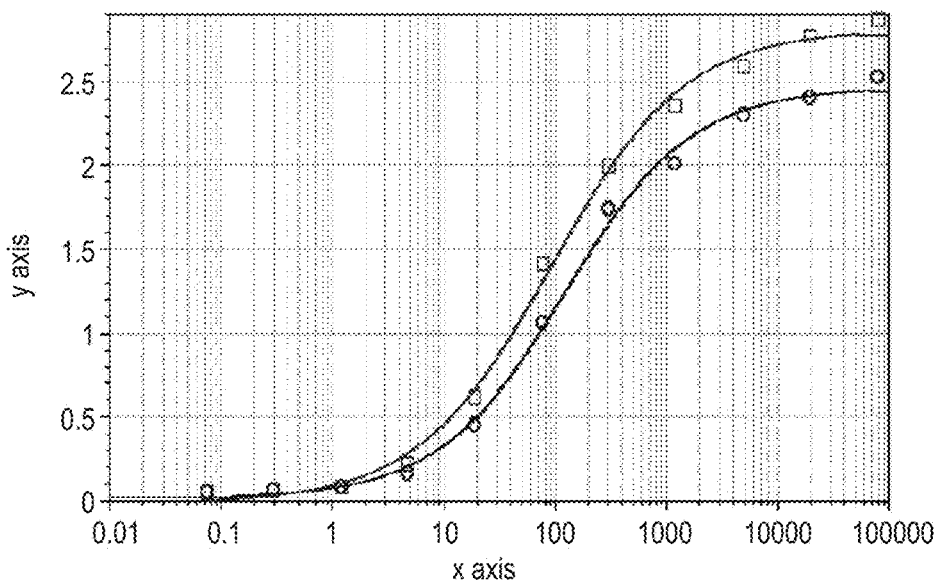

2.5 Binding Curves of CTLA4 Heavy Chain Single Domain Antibodies to CTLA4-Fc Antigen Protein The plates were coated with the obtained CTLA4 heavy chain single-domain antibody at 0.5 µg/well overnight at 4° C. followed by addition of a gradient dilution series of CTLA4-Fc fusion protein and allowed to react for 1 hour at room temperature. After washing, goat anti-human IgG-Fc horseradish peroxidase labeled antibody (lakepharma) was added and allowed to react for 1 hour at room temperature. After washing, horseradish peroxidase c chromogenic solution was added and the absorbance was read at a wavelength of 405 nm. SotfMax Pro v5.4 was used for data processing and mapping analysis to get binding curve of the antibody to CTLA4 and EC50 value (for antibody No. 14, about 50 ng/ml; for antibody No. 155, about 13 ng/ml; for antibody No. C1, about 123 ng/ml; for antibody No. C27, about 93 ng/ml) through four-parameter fitting. The results of 145 and 155 are shown in FIG. 1A, the results of C1 and C27 are shown in FIG. 1B.

2.6 Blocking Curves of CTLA4 Heavy Chain Single-Domain Antibodies on the Interaction Between CD80 and CTLA4

Plates were coated with 0.5 µg/well CTLA4-Fc fusion protein overnight at 4° C. followed by the addition of 100 uL of a gradient dilution series (containing 250 ng/mL CD80-Fc-Biotin) of 100 µL CTLA4 blocking single domain antibody obtained in Example 2.1 per well, allowed to react for 1 hour at room temperature. SA-HRP (purchased from Sigma) was added and allowed to react for 1 hour at room temperature. After adding chromogenic solution, absorbance was read at 405 nm wavelength.

Figure 2A:
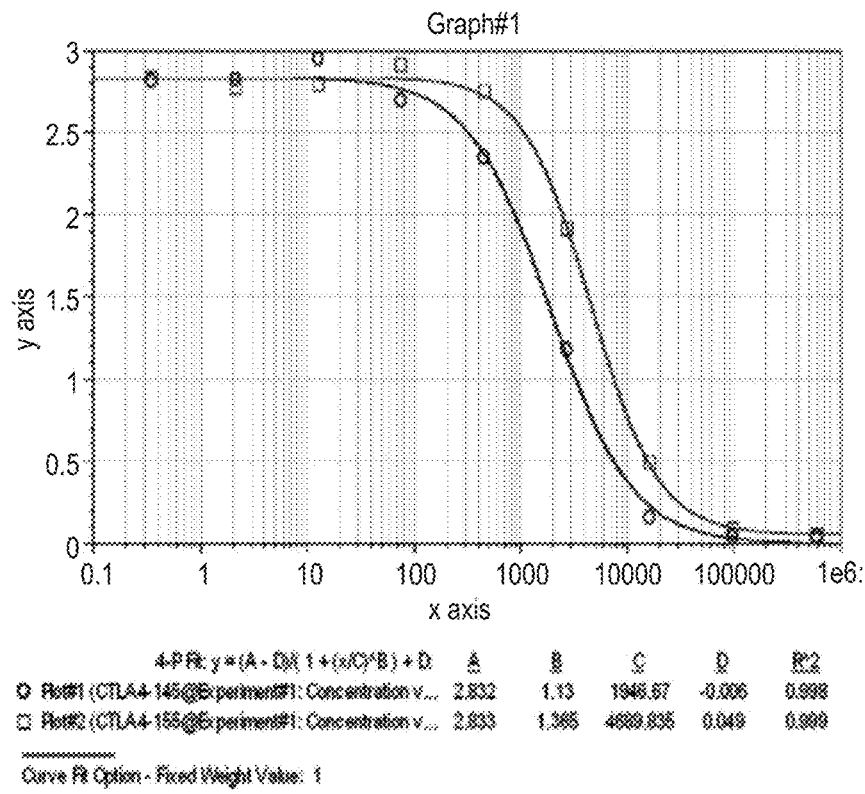
FIGS. 2A and 2B. shows the blocking curves of CTLA4 heavy chain single domain antibodies to CD80/CTLA4 interaction.
Figure 2B:
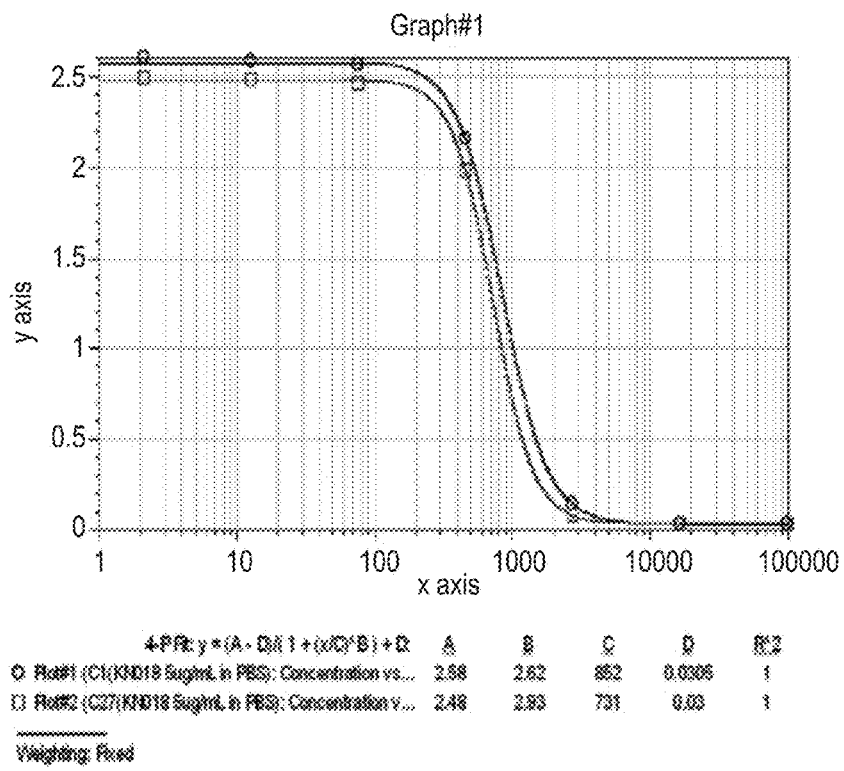

SotfMax Pro v5.4 was used for data processing and graphical analysis to obtain blocking curve and IC50 value of antibody No. C1, C27, 145, 155 to CD80/CTLA4 through four-parameter fitting (IC50 for antibody No. C1 is 852 ng/mL, for antibody No. C27 is approximately 731 ng/ml, for antibody No. 145 is approximately 1.947 µg/ml, for antibody No. 155 is approximately 4.690 µg/ml). The results of 145 and 155 are shown in FIG. 2A, the results of C1 and C27 are shown in FIG. 2B.

2.7 Preparation of Fc Fusion Protein of CTLA4 Single Domain Antibody

The amino acid sequence of human IgG1-Fc region (SEQ ID NO: 132) was obtained based on the constant region amino acid sequence of human immunoglobulin gamma 1 (IgG1) from the protein database Uniprot (P01857). The nucleic acid fragment encoding human IgG1-Fc was obtained from human PBMC total RNA by reverse transcription PCR, and the nucleic acid fragment encoding the fusion protein of CTLA4 single domain antibody obtained in the above Example and Fc was obtained by overlapping PCR, then subcloned into vector pCDNA4 (Invitrogen, Cat V86220).

Recombinant single domain antibody-Fc fusion protein plasmid was transfected into HEK293 cells for antibody expression. The recombinant expression plasmids were diluted with Freestyle 293 medium and added into PEI (polyethylenimine) solution for transformation. Each plasmid/PEI mixture was added to HEK293 cell suspension and incubated at 37° C. and 10% $CO_2$ at 90 rpm. At the same time, 50 μg/L IGF-1 was added. Four hours later EX293 medium, 2 mM glutamine and 50 μg/L IGF-1 were supplemented, cultured at 135 rpm. After 24 hours, 3.8 mM VPA was added. After cultured for 5 to 6 days, the transient expression supernatant was collected and purified by Protein A affinity chromatography to obtain the target CTLA4 single domain antibody-Fc fusion protein.

The sequences of Fc fusion proteins of antibodies No. C1, C27, 145, 155 are shown in SEQ ID NO: 114-117, respectively.

2.8 Blocking Curves of CTLA4 Heavy Chain Single-Domain Antibody Fc Fusion Proteins on the Interaction of CD80 and CTLA4

Plates were coated with CTLA4-Fc fusion protein 0.5 μg/well overnight at 4° C. followed by the addition of 100 μL of a gradient dilution series (containing 250 ng/mL CD80-Fc-Biotin) of CTLA4 blocking single domain antibody obtained in Example 2.7 per well, allowed to react for 1.5 hour at room temperature. SA-HRP (purchased from Sigma) was added and allowed to react for 1.5 hour at room temperature. After adding chromogenic solution, absorbance was read at 405 nm wavelength.

Figure 3:
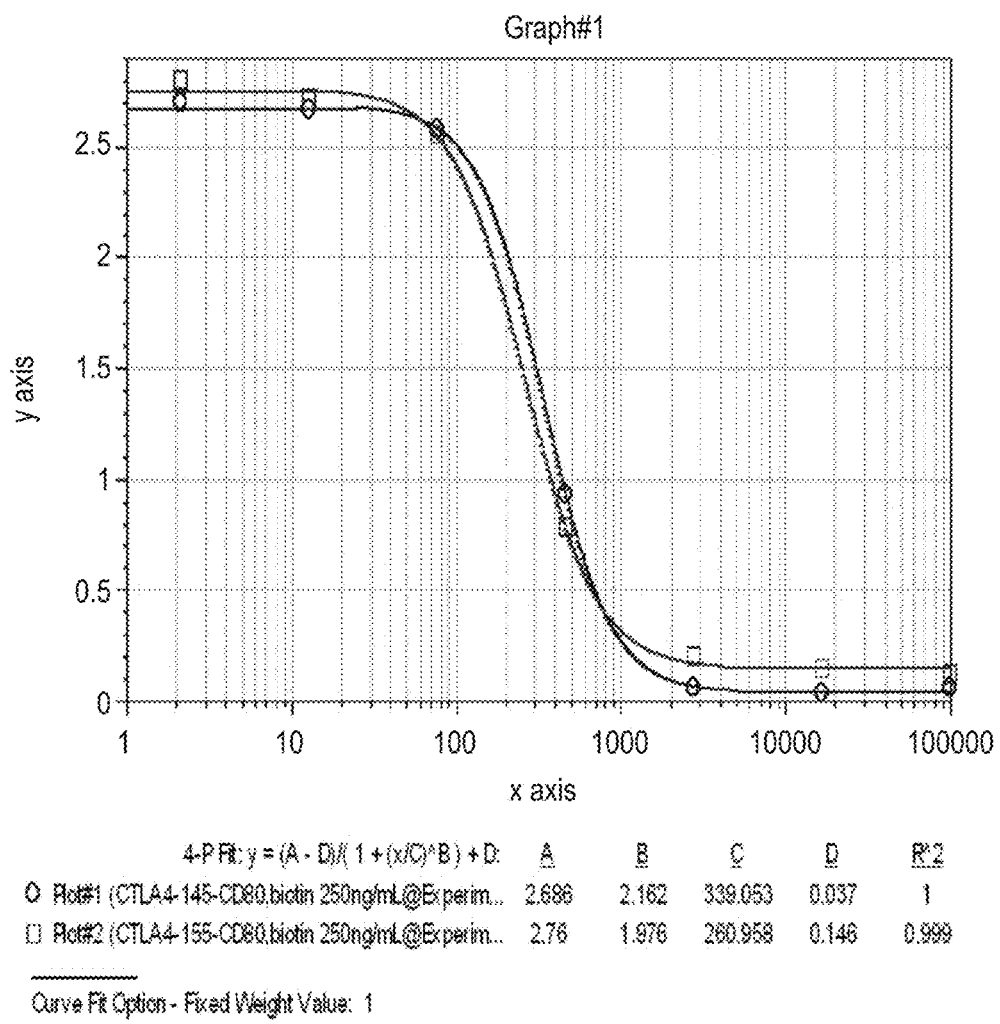
FIG. 3. shows the blocking curves of CTLA4 single domain antibody-Fc fusion proteins to CD80/CTLA4 interaction.

SotfMax Pro v5.4 was used for data processing and graphical analysis to obtain blocking curve and IC50 value of antibody No. 145, 155 to CD80/CTLA4 through four-parameter fitting (IC50 for antibody No. 145 is approximately 339 ng/ml, for antibody No. 155 is approximately 261 ng/ml). The results are shown in FIG. 3.

Example 3 Humanization of CTLA4 Single Domain Antibodies

The humanization is performed by the method of protein surface amino acid humanization (resurfacing) and universal framework grafting method for VHH humanization (CDR grafting to a universal framework).

The steps of humanization are as follows: The homologous modeling of antibody No. C27 and C1 were performed with the modeling software Modeller9. The reference homologous sequence is cAb-Lys3 antibody (PDB code: 1XFP), and the relative solvent accessibility of the amino acids is calculated according to the three-dimensional structure of the protein. If one of the amino acids of antibody No. C27 and C1 are exposed to a solvent, it was replaced with the amino acid at the same position of the reference human antibody DP-47 sequence, until all substitutions were completed.

The antibody No. C27 was humanized, and five humanized variants of the antibody No. C27 were obtained; the antibody No. C1 was humanized, and four humanized variants of the antibody No. C1 were obtained. Table 4 lists the SEQ ID No of these humanized variants as well as the amino acid changes therein, with amino acid residue numbers following Kabat numbering. FIG. 4a shows the alignment of C27 humanized sequences, FIG. 4b shows the alignment of C1 humanized sequences.

TABLE 4

| | SEQ ID NO | Q5V | S11L | A14P | G19R | E44G | R45L | V46E | Q71R | I73N | A74S | K83R | P84A | M89V | S91Y |
|---|---|---|---|---|---|---|---|---|---|---|---|---|---|---|---|
| C27V1 | 101 | ✓ | ✓ | ✓ | | | | | | | ✓ | ✓ | ✓ | ✓ | ✓ |
| C27V2 | 102 | ✓ | ✓ | ✓ | | | | | ✓ | | ✓ | ✓ | ✓ | ✓ | ✓ |
| C27V3 | 103 | ✓ | ✓ | ✓ | | ✓ | ✓ | | ✓ | | ✓ | ✓ | ✓ | ✓ | ✓ |
| C27V4 | 104 | ✓ | ✓ | ✓ | | ✓ | ✓ | ✓ | ✓ | | ✓ | ✓ | ✓ | ✓ | ✓ |
| C27V5 | 105 | ✓ | ✓ | ✓ | | | | ✓ | ✓ | | ✓ | ✓ | ✓ | ✓ | ✓ |
| C1V1 | 106 | ✓ | ✓ | ✓ | ✓ | | | ✓ | | ✓ | ✓ | ✓ | ✓ | ✓ | ✓ |
| C1V2 | 107 | ✓ | ✓ | ✓ | ✓ | | | ✓ | ✓ | ✓ | ✓ | ✓ | ✓ | ✓ | ✓ |
| C1V3 | 108 | ✓ | ✓ | ✓ | ✓ | ✓ | ✓ | ✓ | ✓ | ✓ | ✓ | ✓ | ✓ | ✓ | ✓ |
| C1V4 | 109 | ✓ | ✓ | ✓ | ✓ | ✓ | ✓ | ✓ | ✓ | ✓ | ✓ | ✓ | ✓ | ✓ | ✓ |

Example 4 Preparation of CTLA4 Blocking Antibody Protein Using Mammalian Cells 4.1 Preparation of Fc Fusion Protein of CTLA4 Single Domain Antibody The amino acid sequence of human IgG1-Fc region (SEQ ID NO: 132) was obtained based on the constant region amino acid sequence of human immunoglobulin gamma1 (IgG1) from the protein database Uniprot (P01857). The nucleic acid fragment encoding human IgG1-Fc was obtained from human PBMC total RNA by reverse transcription PCR, and the nucleic acid fragment encoding the fusion protein of CTLA4 single domain antibody obtained in the above Example and Fc was obtained by overlapping PCR, then subcloned into vector pCDNA4 (Invitrogen, Cat V86220).

Recombinant single domain antibody-Fc fusion protein plasmid was transfected into HEK293 cells for antibody expression. The recombinant expression plasmids were diluted with Freestyle 293 medium and added into PEI (polyethylenimine) solution for transformation. Each plasmid/PEI mixture was added to HEK293 cell suspension and incubated at 37° C. and 10% $CO_2$ at 90 rpm. At the same time, 50 μg/L IGF-1 was added. Four hours later EX293 medium, 2 mM glutamine and 50 μg/L IGF-1 were supplemented, cultured at 135 rpm. After 24 hours, 3.8 mM VPA was added. After cultured for 5 to 6 days, the transient expression supernatant was collected and purified by Protein A affinity chromatography to obtain the target CTLA4 single domain antibody-Fc fusion protein.

The sequences of the CTLA4 single domain antibody-Fc fusion proteins as obtained are shown in SEQ ID NO: 114-126, respectively, wherein SEQ ID NO: 118-126 are Fc fusion proteins of humanized CTLA4 single domain antibodies. These fusion proteins comprise one CTLA4 binding domain and form homo-dimmers, each of which comprises two CTLA4 binding domains, such that these fusion proteins are also referred to as bivalent CTLA4 single domain antibody-Fc fusion protein.

4.2 Preparation of CTLA4 Antibodies from BMS

The gene of anti-CTLA4 antibody ipilimumab from BMS, Inc. was cloned by the method for antibody 10D1 in US20020086041 and cloned into the vector pCDNA4.

The recombinant plasmid was transiently transfected into HEK293 cells by the same method as in Example 4.1, and the resulting anti-CTLA4 antibody of BMS was renamed as 10D1.

4.3 Comparison of the Expression of CTLA4 Single-Domain Antibody Fc Fusion Protein and the Known CTLA4 Antibodies Using the same expression system and transient transfection conditions, the expression level of the CTLA4 single-domain antibody Fc fusion protein of the present invention was higher than 400 mg/L, while the expression level of the antibody 10D1 was about 150 mg/L. This result indicates that the CTLA4 single-domain antibody Fc fusion protein of the present invention is more stable in structure and can result in higher expression level than the known CTLA4 antibodies.

4.4 Preparation of Tetravalent CTLA4 Single Domain Antibody Fc Fusion Protein

A nuclei acid fragment encoding a fusion protein of two tandem CTLA4 single domain antibodies and one Fc region was obtained by overlapping PCR, and then subcloned into vector pCDNA4 (Invitrogen, Cat V86220). The constructed recombinant plasmid was used to transfect HEK293 cells for transient expression by the same method as described in 4.1. A fusion protein of two tandem CTLA4 single domain antibodies and one Fc was obtained, which could form a dimeric molecule comprising four CTLA4-binding domains, also called tetravalent CTLA4 single domain antibody Fc fusion protein.

The mean transient expression level of the tetravalent CTLA4 single domain antibody Fc fusion proteins is about 400 mg/L, comparable to that of the bivalent CTLA4 single domain antibody Fc fusion proteins.

Example 5 Characterization of CTLA4 Single-Domain Antibody Fc Fusion Protein 5.1 Binding Ability of CTLA4 Single Domain Antibody Fc Fusion Protein to CTLA4 (by ELISA)

Plates were coated with 0.5 µg/well CTLA4 single-domain Fc fusion protein obtained by Example 2.7 and 4.1 or 10D1 protein obtained by Example 4.2 overnight at 4° C. followed by the addition of a gradient dilution series of CTLA4-Fc-Biotin, allowed to react for 1 hour at room temperature. SA-HRP (purchased from Sigma) was added and allowed to react for 1.5 hour at room temperature. After adding chromogenic solution, absorbance was read at 405 nm wavelength.

SotfMax Pro v5.4 was used for data processing and graphical analysis. Through four-parameter fitting, binding curve and EC50 value of the antibody to CTLA4 (all test antibody EC50 value of about 60-70 ng/mL) were obtained to reflect the affinity to CTLA4.

Figure 5:
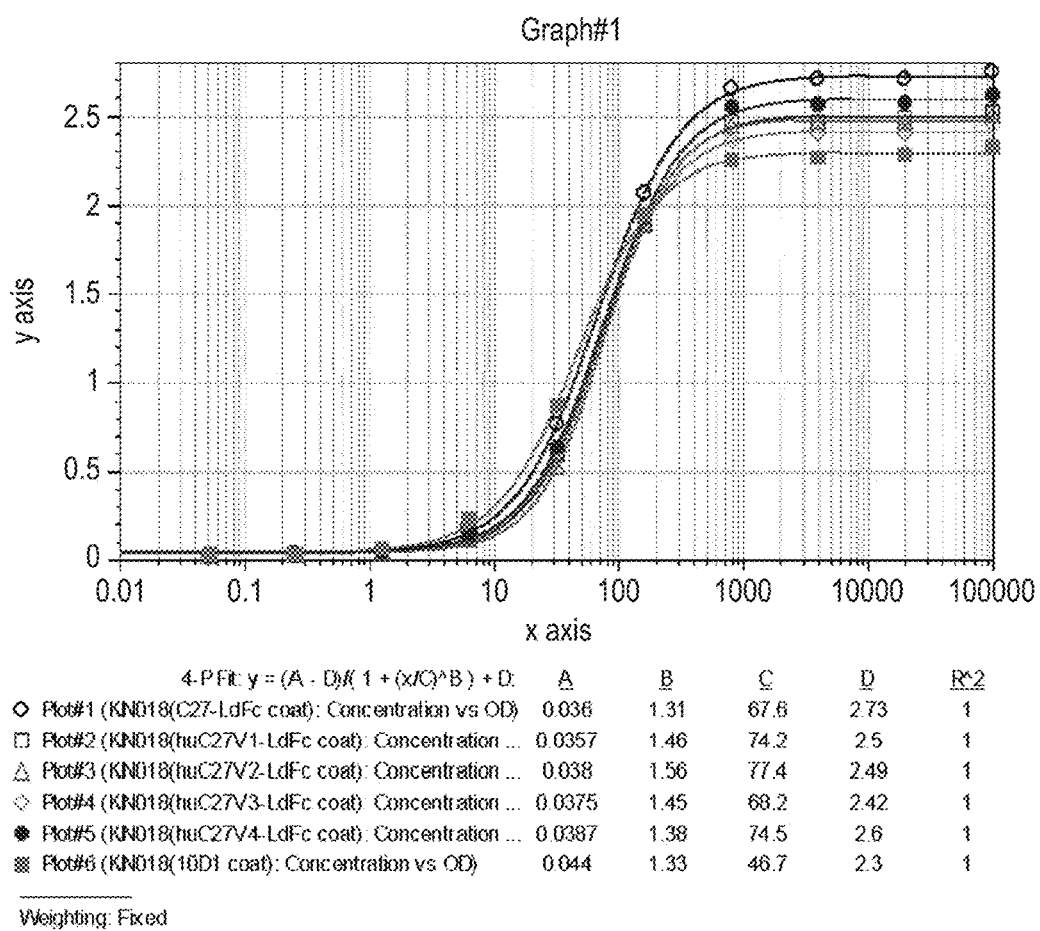
FIG. 5. shows the binding curves of CTLA4 single domain antibody-Fc fusion proteins to CTLA4 (by ELISA).

The results are shown in FIG. 5, where the longitudinal coordinate is OD405 and the horizontal ordinate is the concentration of CTLA4 single domain antibody Fc-fusion protein (or 10D1 protein) (in ng/mL); four different humanized forms of the Fc fusion protein of antibody No. C27 were labeled as: huC27v1-LdFc (SEQ ID NO:118), huC27v2-LdFc (SEQ ID NO:119), huC27v3-LdFc (SEQ ID NO:120), huC27v4-LdFc (SEQ ID NO:121). The four proteins have comparable affinity for CTLA4, and comparable to unhumanized C27-LdFc and known CTLA4 antibody 10D1 of BMS.

5.2 Binding Ability of CTLA4 Single-Domain Antibody Fc Fusion Protein to CTLA4 (by ELISA)

Plates were coated with 0.5 µg/well CTLA4 single-domain Fc fusion protein obtained by Example 2.7 and 4.1 overnight at 4° C., followed by the addition of a gradient dilution series of CTLA4-Fc-Biotin, allowed to react for 1 hour at room temperature. SA-HRP (purchased from Sigma) was added and allowed to react for 1.5 hour at room temperature. After adding chromogenic solution, absorbance was read at 405 nm wavelength.

SotfMax Pro v5.4 was used for data processing and graphical analysis. Through four-parameter fitting, binding curve and EC50 value of the antibody to CTLA4 (all test antibody EC50 value of about 25-35 ng/mL) were obtained to reflect the affinity to CTLA4.

Figure 6:
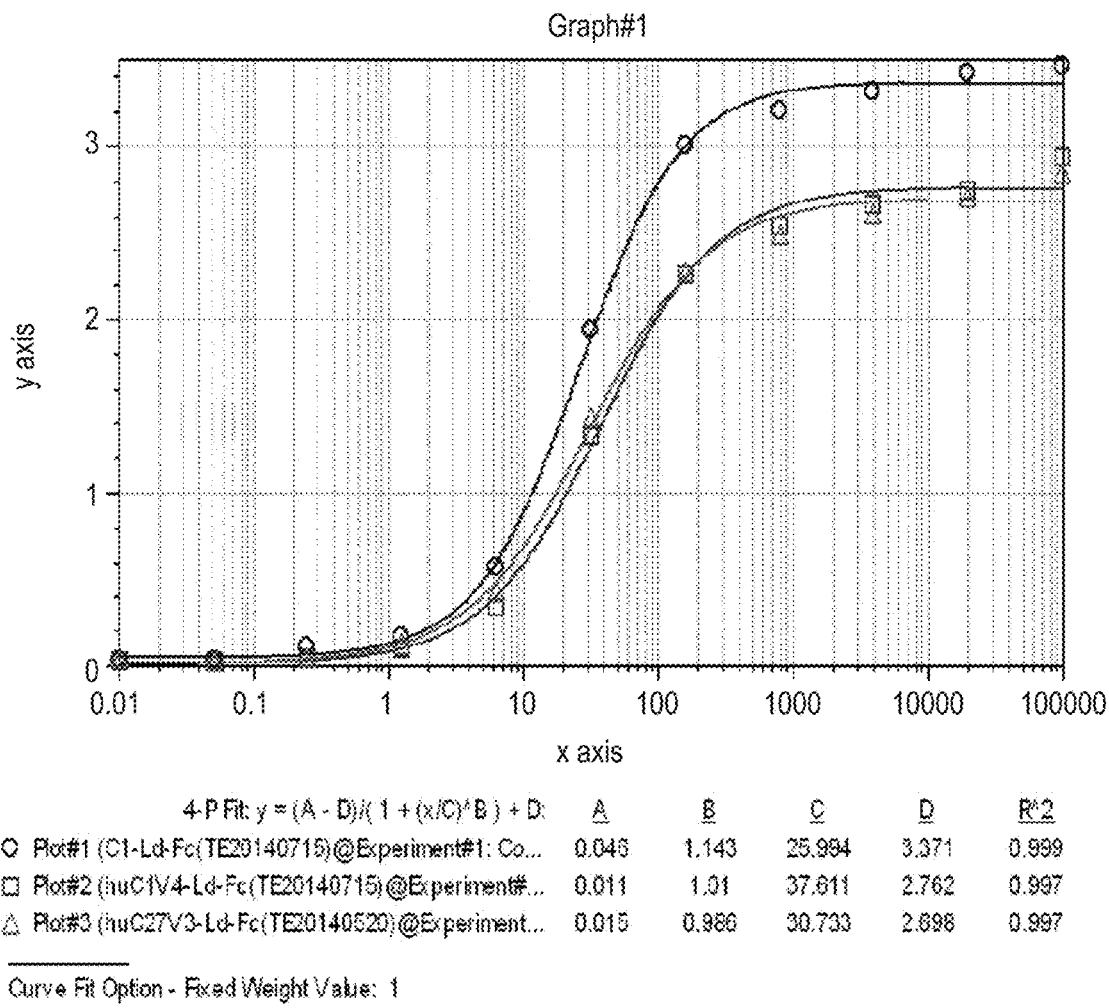
FIG. 6. shows the binding curves of CTLA4 single domain antibody-Fc fusion proteins to CTLA4 (by ELISA).

The results are shown in FIG. 6, where the longitudinal coordinate is OD405 and the horizontal ordinate is the concentration of CTLA4 single domain antibody Fc-fusion protein (in ng/mL); triangle represents the humanized form Fc fusion protein of the antibody No. C27, huC27v3-LdFc (SEQ ID NO: 120), square represents the humanized form Fc fusion protein of the antibody No. C1, huC1v4-Ld-Fc (SEQ ID NO: 126), circle represents the Fc fusion protein of antibody No. C1, C1-1d-Fc. C1-1d-Fc has a much higher coloration than the other two due to the long reaction time, and thus it shows better EC50. However, there is actually no difference in the affinity of the three proteins for CTLA4.

5.2 Blocking Effect of CTLA4 Single-Domain Antibody Fc Fusion Protein to CTLA4-CD80 Interaction (by Competitive ELISA)

Plates were coated with 0.5 µg/well CTLA4-Fc fusion protein overnight at 4° C. followed by the addition of 100 uL of a gradient dilution series (containing 250 ng/mL CD80-Fc-Biotin) of CTLA4 single-domain Fc fusion protein obtained by Example 4.1 or 10D1 protein obtained by Example 4.2 per well, allowed to react for 1 hour at room temperature. SA-HRP (purchased from Sigma) was added and allowed to react for 1 hour at room temperature. After adding chromogenic solution, absorbance was read at 405 nm wavelength.

Figure 7A:
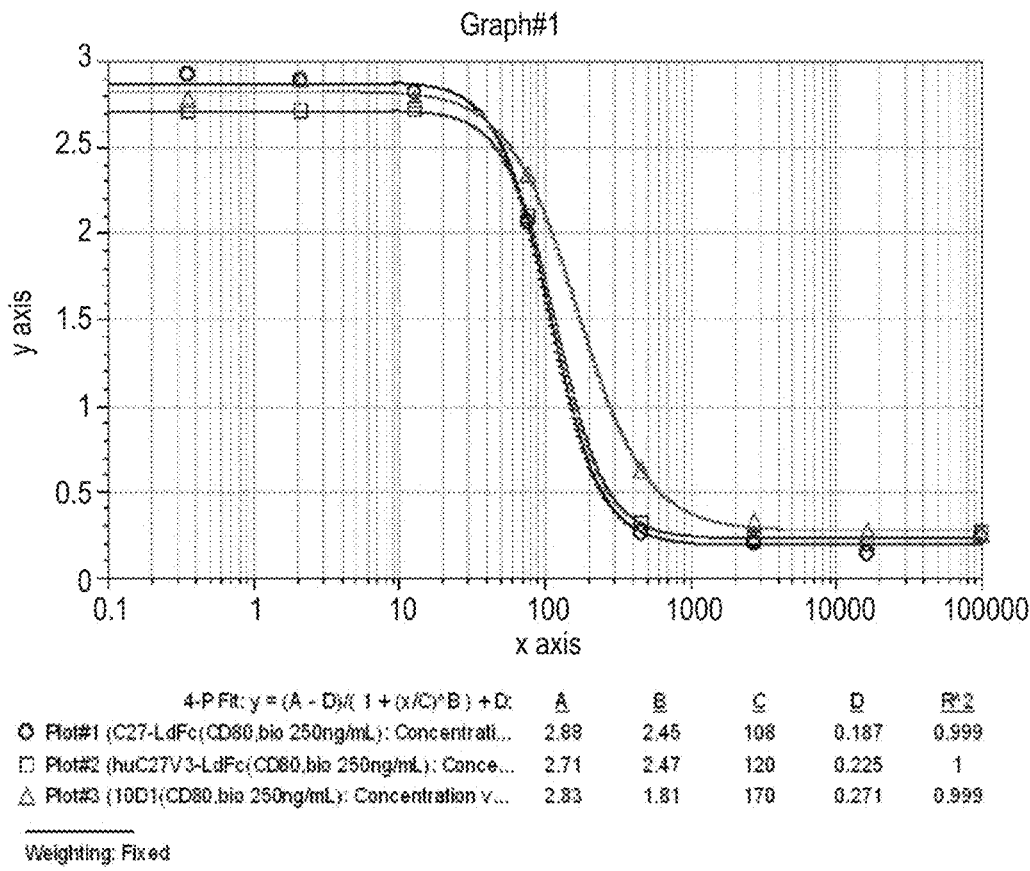
FIGS. 7A and 7B. shows the blocking curves of CTLA4 single domain antibody-Fc fusion proteins to CD80/CTLA4 interaction (by competitive ELISA).
Figure 7B:
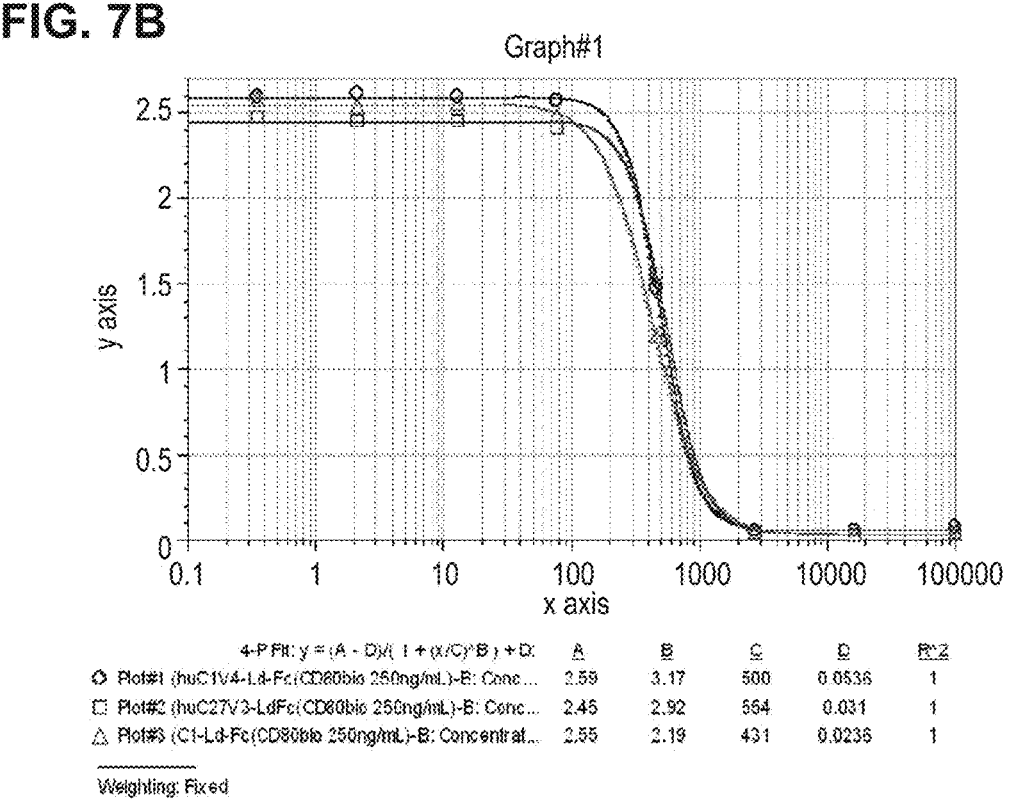

SotfMax Pro v5.4 was used for data processing and graphical analysis. Through four-parameter fitting, blocking curve and IC50 value of the antibody to CTLA4-CD80 were obtained. The results are shown in FIG. 7A and FIG. 7B. It can be seen that the two different single-domain antibodies No. C27 and C1, whether humanized or the original sequence, have comparable ability to block the CTLA4-CD80 interaction, and are superior to the already marketed antibody of BMS (labelled as 10D1).

5.3 Binding Ability of Tetravalent CTLA4 Single-Domain Antibody Fc Fusion Protein to CTLA4 (by ELISA)

Plates were coated with CTLA4 single-domain Fc fusion protein obtained by Example 4.1 and tetravalent CTLA4 single-domain antibody Fc fusion protein obtained by Example 4.4 0.5 µg/well overnight at 4° C. followed by the addition of a gradient dilution series of CTLA4-Fc-Biotin, allowed to react for 1 hour at room temperature. SA-HRP (purchased from Sigma) was added and allowed to react for 1.5 hour at room temperature. After adding chromogenic solution, absorbance was read at 405 nm wavelength.

SotfMax Pro v5.4 was used for data processing and graphical analysis. Through four-parameter fitting, binding curve and EC50 value of the antibody to CTLA4 (all test antibody EC50 value of about 25-35 ng/mL) were obtained to reflect the affinity to CTLA4.

Figure 8:
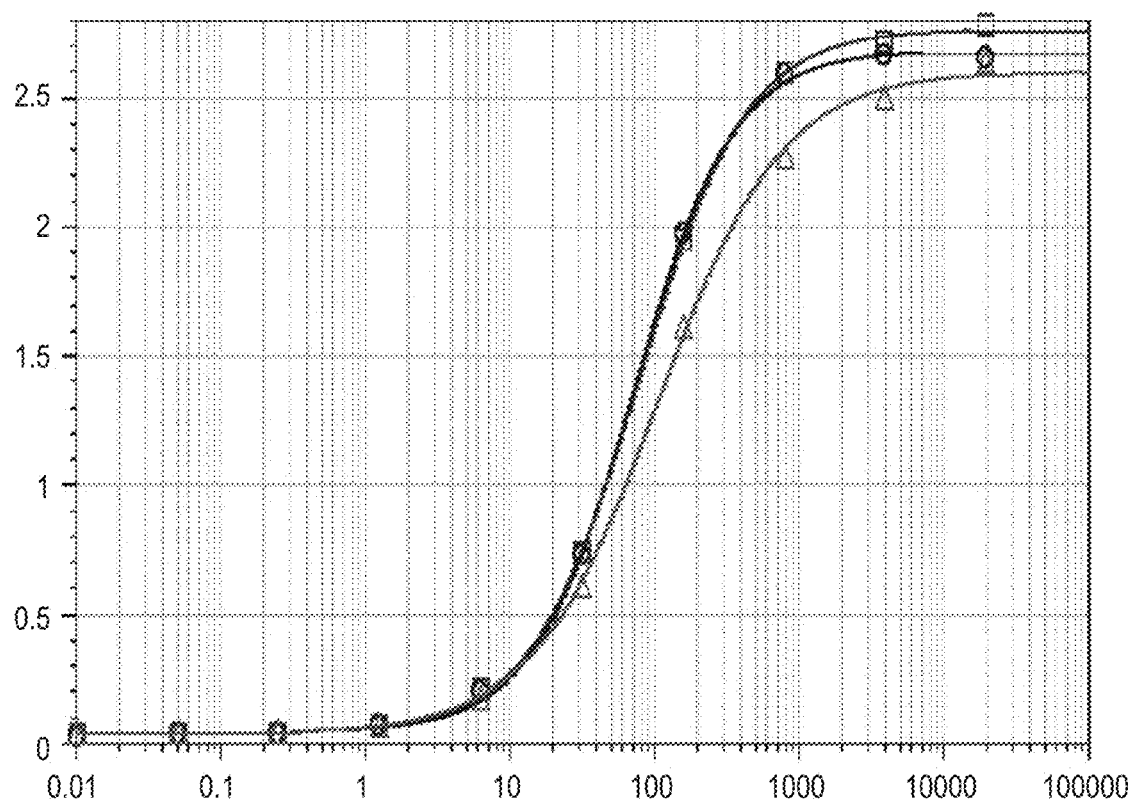
FIG. 8. shows the binding curves of tetravalent CTLA4 single domain antibody-Fc fusion proteins to CTLA4 (by competitive ELISA).

The results are shown in FIG. 8, where the longitudinal coordinate is OD405 and the horizontal ordinate is the concentration of CTLA4 single domain antibody Fc-fusion protein (in ng/mL); triangle represents tetravalent CTLA4 single-domain antibody Fc fusion protein, huC1v4-tet-Fc (SEQ ID NO: 128); square represents the humanized form Fc fusion protein of the antibody No. C1, huC1v4-Fc; circle represents Fc fusion protein of CTLA4 single-domain antibody No. C1, C1-1d-Fc. The EC50 of the three proteins is slightly different, but considering that the molecular weight of the tetravalent protein is about 5/4 of the divalent molecule, there is no difference in the affinity of the three proteins for CTLA4 when converted into a molar concentration.

5.4 Identification and Comparison of the Binding Ability of Bivalent and Tetravalent CTLA4 Single-Domain Antibody Fc Fusion Protein to CTLA4 (SPR Method)

The binding kinetics of the CTLA4 single domain antibody Fc fusion protein obtained in the above examples to recombinant human CTLA4 was measured by the surface plasmon resonance (SRP) method using a BIAcore X100 instrument. Recombinant camel anti human Fc antibody was coupled to a CM5 biosensor chip to obtain approximately 1000 response units (RU). For kinetic measurements, the antibodies were diluted (1.37 to 1000 nm) with HBS-EP+1× buffer (GE, cat #BR-1006-69) to fixed concentration and injected for 120 s at 25° C. to ensure obtaining response value higher than 100 RU, and followed by serial three-times dilution for the fusion protein of CTLA4 and mouse Fc and injected for 120 s at 25° C. with a dissociation time of 30 min, regenerated with 10 mM Glycine-HCl (pH 2.0) for 120 s. Binding rates (kon) and dissociation rates (koff) were calculated using a simple one-to-one Languir binding model (BIAcore Evaluation Software version 3.2). The equilibrium dissociation constant (kD) is calculated as the ratio koff/kon.

The measured binding affinities of anti-CTLA4 antibodies are shown in Table 5. The results show that the affinity of the tetravalent molecule is slightly lower than that of the divalent molecule, possibly due to a certain steric hindrance.

TABLE 5

| Antibody | Ka | Kd | KD |
| --- | --- | --- | --- |
| HuC1V4-tet-Fc | 1.318E+5 | 2.510E−5 | 1.905E−10 |
| HuC1V4-Ld-Fc | 2.335E+5 | 2.035E−4 | 8.715E−11 |

5.4 Blocking Ability of Bivalent and Tetravalent CTLA4 Single Domain Fc Fusion Protein on CTLA4/CD80 Interaction (by Cell Neutralization Experiment)

96-well plate was inoculated with $1.5\times10^5$ Jurkat T cells (from the Shanghai Cell Bank of Chinese Academy of Sciences), supplemented with Anti-human CD3 (50 ng/mL), and incubated at 37° C. for 15 min, then a gradient dilution of the bivalent or tetravalent CTLA4 single-domain antibody Fc fusion protein (30 ng/ml-0.94 ng/ml, 100 ng/mL CTLA4-Fc fusion protein was added to the dilution) and equal-density Raji cells (from the Shanghai Cell Bank of Chinese Academy of Sciences) were added. After 24 hours of culture, the supernatant was collected for detection of IL-2 expression. The data were processed with Soft Max to calculate the effect of inhibiting IL-2 by the bivalent or tetravalent CTLA4 single-domain antibody Fc fusion protein through neutralization of CTLA4-Fc fusion protein. The effects were compared using EC50.

Figure 9:
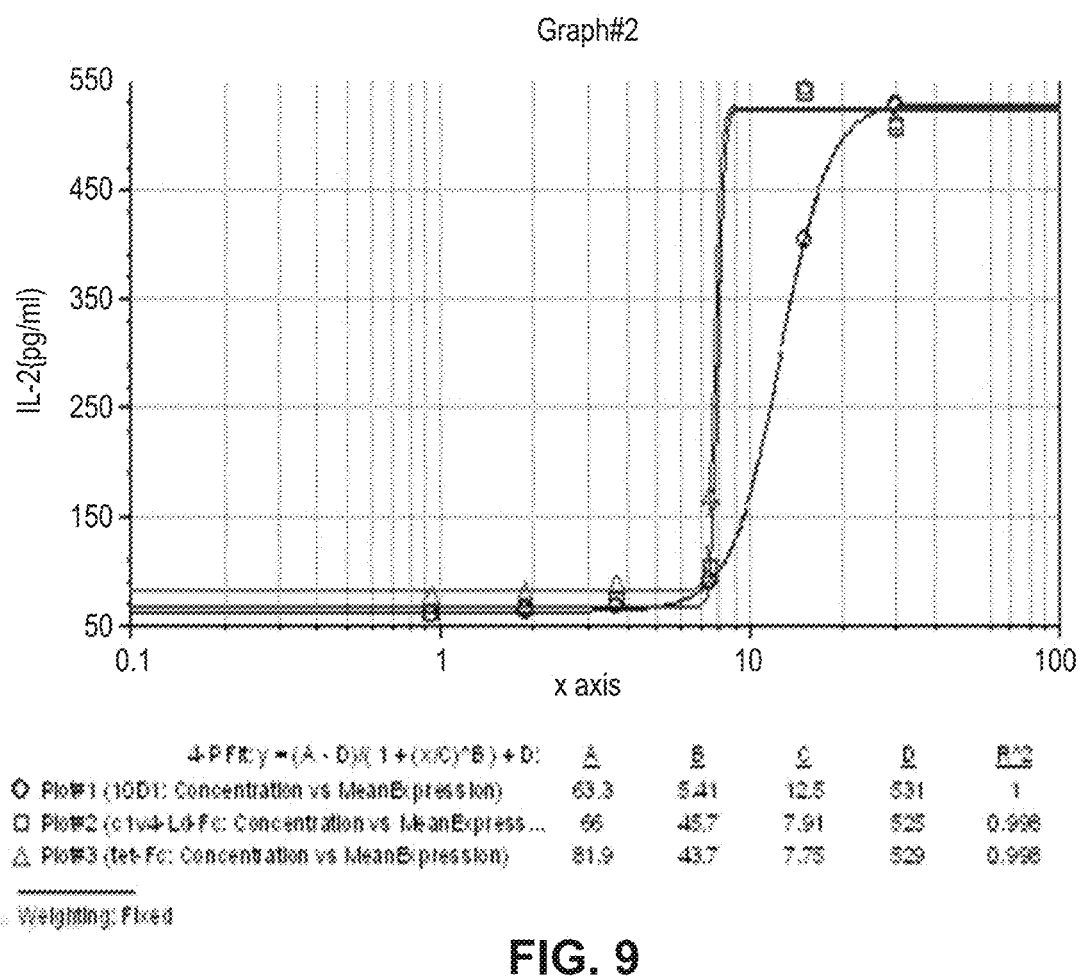
FIG. 9. shows the blocking capacity of bivalent or tetravalent CTLA4 single domain antibody-Fc fusion proteins to CD80/CTLA4 interaction (by cell neutralization experiment).

Results are shown in FIG. 9. The bivalent and tetravalent CTLA4 single-domain antibody Fc fusion proteins (represented by square and triangle, respectively) were equivalent in inhibiting CTLA4-CD80, and were superior to the already marketed CTLA4 antibody of BMS (Labeled as 10D1, indicated by a circle).

5.5 Binding Specificity of the CTLA4 Single Domain Antibody Fc Fusion Protein for CTLA4 Protein Human HEK293 cells transiently express human CTLA4, CD28, PD1 protein on membranes by transient transfection of a plasmid carrying the full-length human B7 family protein genes (pCDNA4, Invitrogen, Cat V86220). The plasmid also allows the C-terminus of the target protein to be fused to the EGFP protein so that the level of B7 family protein expressed on the membrane can be examined by green fluorescence intensity. The constructed transient transfected cell lines include 293-CTLA4-EGFP, 293-PD1-EGFP, 293-CD28-EGFP.

The constructed cells were resuspended in 0.5% PBS-BSA buffer and huC1v4-tet-Fc antibody was added. At the same time, a negative control of 2 µg of a single domain antibody against other unrelated target was set up and incubated on ice for 20 minutes. After washing, eBioscience secondary antibody anti-hIg-PE was added, on ice for 20 min. After washing, the cells were resuspended in 500 µl of 0.5% PBS-BSA buffer and detected by flow cytometry.

Figure 10:
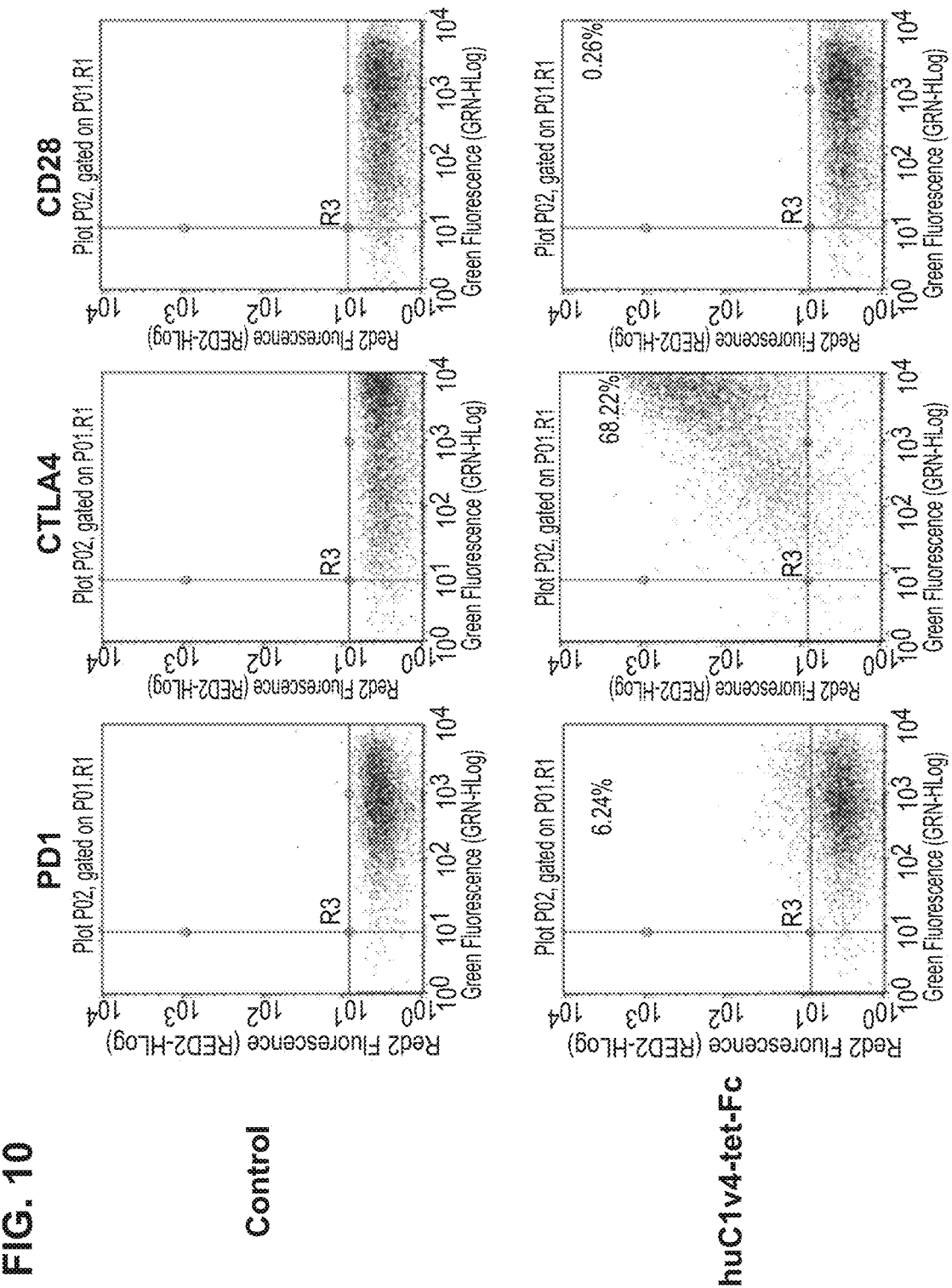
FIG. 10. the binding specificity of CTLA4 single domain antibody-Fc fusion proteins to CTLA4 protein detected by flow cytometry.

The results are shown in FIG. 10. The upper row shows the control group, the lower row shows the sample groups. It is clear that huC1v4-tet-Fc specifically binds to human CTLA4 protein only, not to other B7 family proteins.

5.6 Binding of Tetravalent CTLA4 Single Domain Fc Fusion Protein to Monkey CTLA4 Protein Monkey CTLA4-Fc protein was purchased from Yiqiao Shenzhou. The biotinylated protein huC1v4-tet-Fc-Biotin was obtained using the Thermo Biotinlytion kit with the tetravalent CTLA4 single domain antibody Fc fusion protein obtained in Example 4.4.

Plates were coated with monkey CTLA4-Fc protein or human CTLA4-Fc protein, 0.5 ag/well, overnight at 4° C., followed by addition of gradient dilution series of the huC1v4-tet-Fc-Biotin, allowed to react for 1 hour at room temperature. Then, SA-HRP (purchased from Sigma) was added and allowed to react at room temperature for 1.5 hour. Then, chromogenic agent was added and the absorbance was read at 405 nm.

SotfMax Pro v5.4 was used for data processing and graphical analysis. Through four-parameter fitting, blocking curve and EC50 value of the antibody to monkey CTLA4 or human CTLA4 were obtained.

Figure 11:
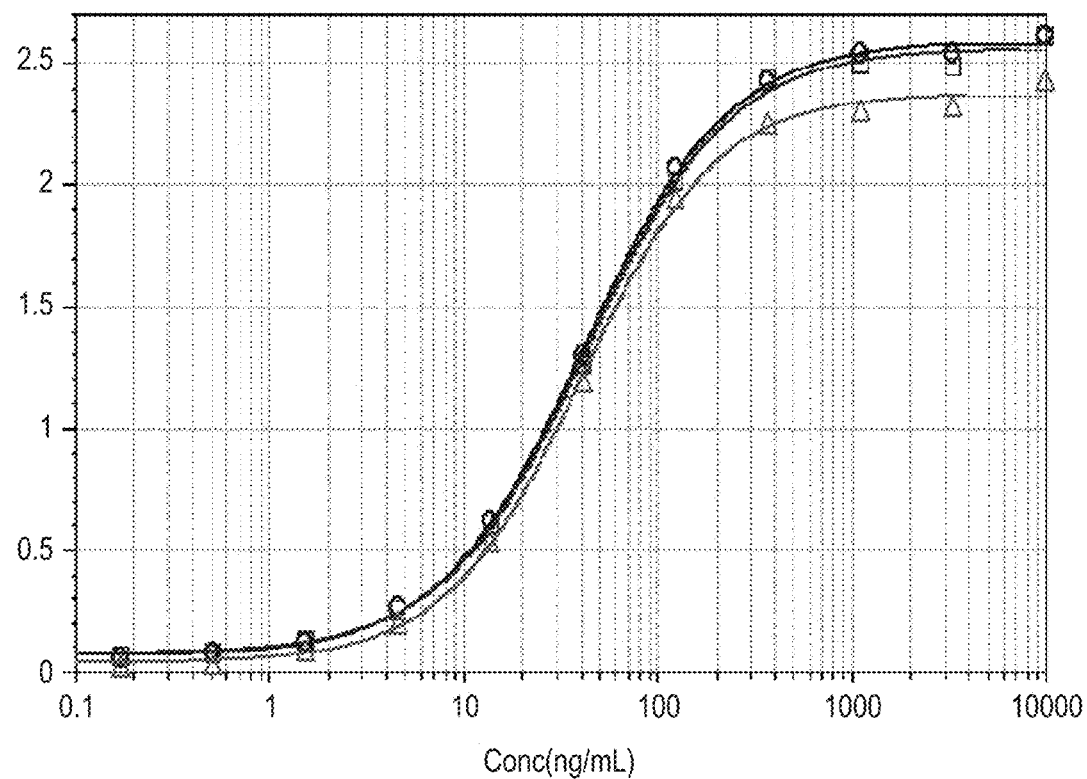
FIG. 11. shows the binding of tetravalent CTLA4 single domain antibody-Fc fusion proteins to monkey CTLA4 protein detected by flow cytometry.

The results are shown in FIG. 11, where longitudinal coordinate is OD405 and the abscissa is the concentration of the tetravalent CTLA4 single domain antibody Fc fusion protein (in ng/mL); the triangle represents the binding with monkey CTLA4, the square and circle represent the binding with human CTLA4. It can be seen that the tetravalent CTLA4 single domain antibody Fc fusion protein can efficiently bind to monkey CTLA4 protein.

5.7 Activation of PBMC by CTLA4 Single Domain Antibody Fc Fusion Protein

Peripheral blood mononuclear cells (PBMCs) were isolated from peripheral blood of healthy donors by density gradient centrifugation using isolation solution for human lymphocytes (Tianjin Hao Yang).

Plates were coated with 0.3 µg/well anti-CD3 antibody overnight at 4° C. The next day, $1\times10^5$ PBMCs were added to each well, at the same time, 10 µg/mL CTLA4 single domain antibody Fc fusion protein huC1v4-Fc, huC27-Fc or the BMS CTLA4 antibody (named 10D1) were added to each well respectively. After cultured for 5 days, the supernatant was taken and the level of IFN-γ in the supernatant was detected by IFN-γ ELISA kit (ebioscience).

Figure 12:
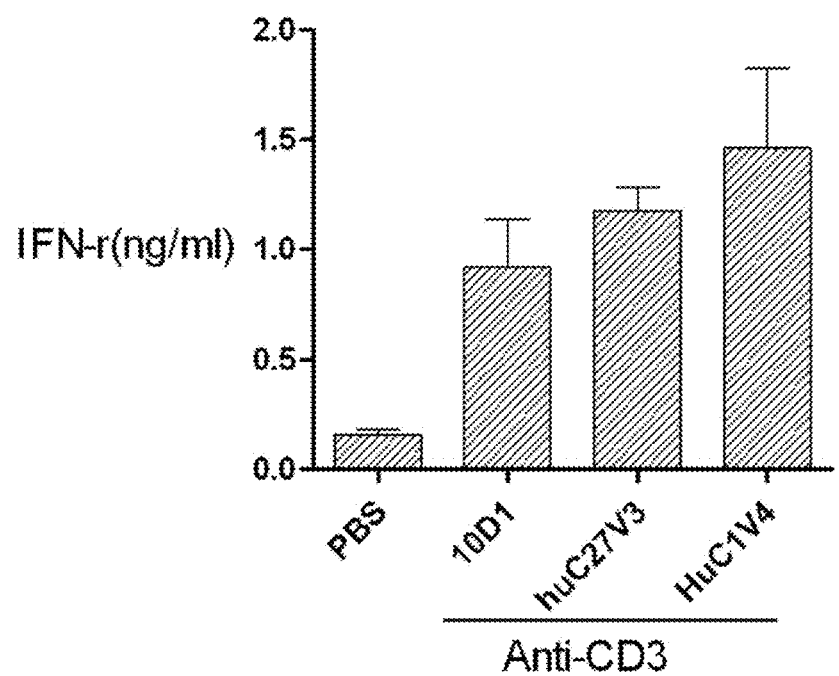
FIG. 12. shows the activation of PBMC by CTLA4 single domain antibody-Fc fusion proteins.

The results are shown in FIG. 12. It can be seen that at the concentration of 10 µg/mL, CTLA4 single domain antibody Fc fusion protein combined with anti-CD3 antibody can enhance the secretion of γ-interferon by PBMC cells, i.e. CTLA4 single domain antibody Fc fusion protein enhances the activation of PBMC cells. Moreover, both huC1v4-Ld-Fc and huC27v3-Ld-Fc exhibited better activity than the BMS anti-CTLA4 antibody.

5.8 Activation of PBMC by Bivalent and Tetravalent CTLA4 Single Domain Antibody Fc Fusion Protein Peripheral blood mononuclear cells (PBMCs) were isolated from peripheral blood of healthy donors by density gradient centrifugation using isolation solution for human lymphocytes (Tianjin Hao Yang).

Plates were coated with 0.3 µg/well anti-CD3 antibody overnight at 4° C. The next day, $1\times10^5$ PBMCs were added to each well, at the same time, 0.03 ug/mL bivalent or tetravalent CTLA4 single domain antibody Fc fusion protein huC1v4-LD-Fc (labeled as Ld in the figure), huC1v4-tet-Fc (labeled as tet in figure) or the BMS CTLA4 antibody (named 10D1) were added to each well respectively. After cultured for 5 days, the supernatant was taken and the level of IFN-γ in the supernatant was detected by IFN-γ ELISA kit (ebioscience).

Figure 13:
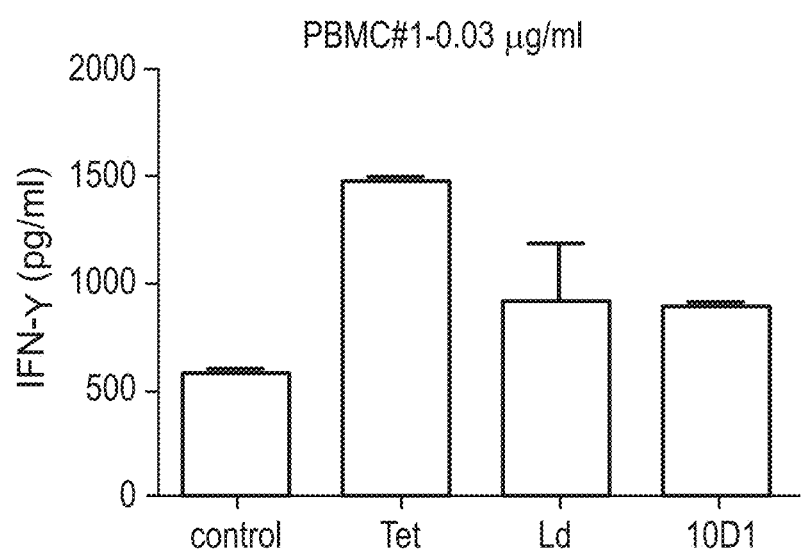
FIG. 13. shows the comparison of the activation of PBMC by bivalent and tetravalent CTLA4 single domain antibody-Fc fusion proteins.

The results are shown in FIG. 13. It can be seen that at the low dose concentration of 0.03 μg/mL, CTLA4 single domain antibody Fc fusion protein (both bivalent or tetravalent) combined with anti-CD3 antibody can enhance the secretion of γ-interferon by PBMC cells, i.e. bivalent or tetravalent CTLA4 single domain antibody Fc fusion protein significantly enhances the activation of PBMC cells at the low dose concentration of 0.03 μg/mL. Moreover, tetravalent CTLA4 single domain antibody Fc fusion protein huC1v4-tet-Fc exhibited activity better activity than the BMS anti-CTLA4 antibody.

5.9 Activation of CD4+ T Cells by CTLA4 Single-Domain Antibody Fc Fusion Protein in Dendritic Cell-T Cell Mixed Lymphoid Reaction Peripheral blood mononuclear cells (PBMCs) were isolated from white blood cells of peripheral blood from healthy donors by density gradient centrifugation using isolation solution for human lymphocytes (Tianjin Hao Yang). They were then incubated with serum-free RPMI 1640 medium for 1-2 hours to remove non-adherent cells and cells were cultured in RPMI containing 10% FBS, 10 ng/ml GM-CSF and 20 ng/mL IL-4. After culturing for 5-6 days, 10 ng/ml of TNF-α was added and incubated for 24 hours to obtain mature dendritic cells.

Dendritic cells obtained by this method were resuspended in RPMI complete medium, 2×10$^5$/ml. Then 50 μl per well was added to a 96-well U-bottom plate (Costar: 3799) and cultured in an incubator.

CD4+ T cells were isolated from PBMC of another donor using a magnetic bead isolation kit (Miltenyi Biotec: 130-096-533) following the instructions of the manufacturer.

1×10$^4$ dendritic cells and 1×10$^5$ CD4+ T cells obtained by the above methods were mixed, resuspended in RPMI complete medium and added to a 96-well culture plate, and 50 μl of the cell mixture was added to each well. 100 μl per well of huC1v4-Ld-Fc diluted in RPMI complete medium was added to a final antibody concentration of 0.1 μg/ml or 0.01 μg/ml. Supernatants were collected 5-7 days after culture, and IFN-γ level in the supernatant was detected by IFN-γ ELISA kit (ebioscience).

Figure 14:
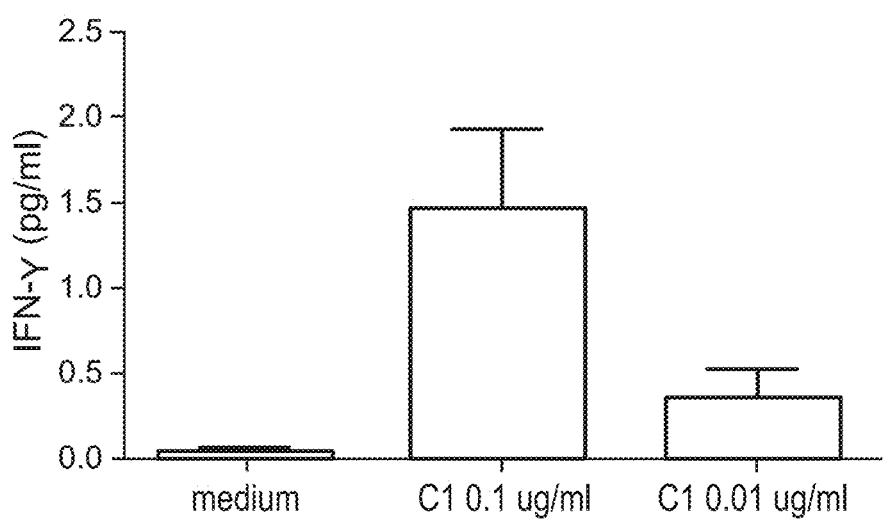
FIG. 14. shows the activation of CD4+T cells by CTLA4 single domain antibody-Fc fusion proteins.
Figure 15:
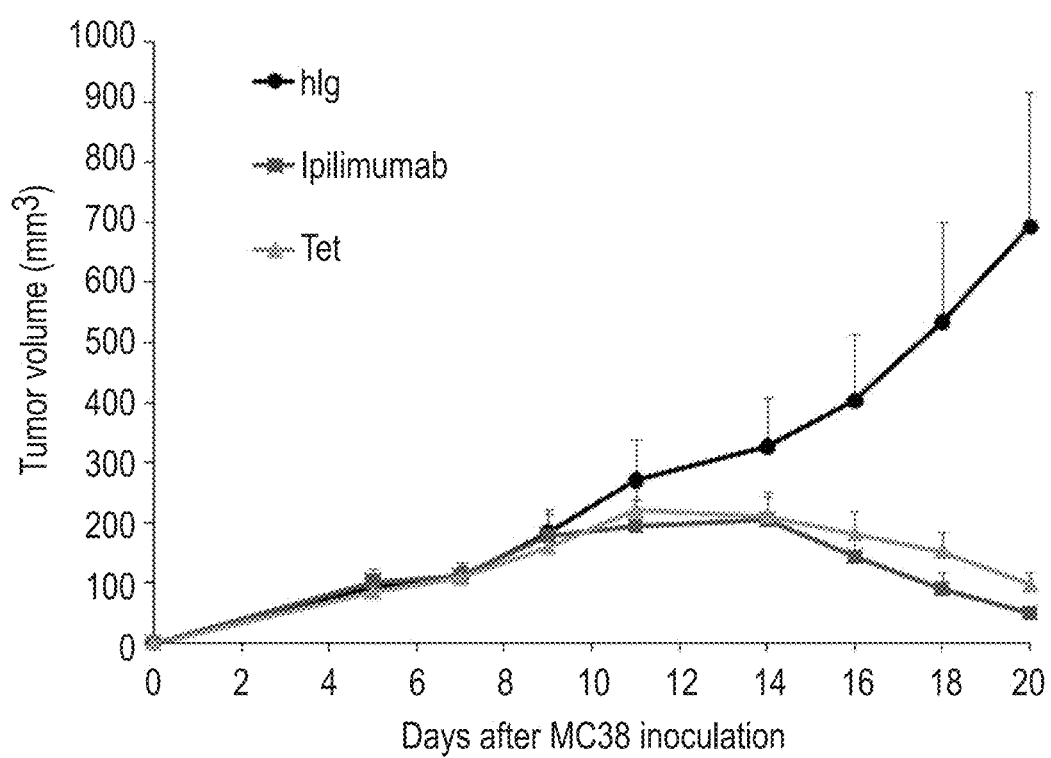
FIG. 15. shows that the in vivo inhibition effect of CTLA4 single domain antibody-Fc fusion proteins to MC38 tumor in CTLA4-humanized mice.

The results are shown in FIG. 14. It can be seen that CTLA4 single-domain antibody Fc fusion protein can enhance the IFN-γ secretion of CD4+ T cells in mixed lymphocyte reaction. That is, the CTLA4 blocking single-domain antibody Fc fusion protein enhances T cell activation. Moreover, this biological activity was concentration-dependent, and a significant activation of T cells was observed at a low dose concentration (0.01 μg/ml).

5.10 Anti-Tumor Effect of Tetravalent CTLA4 Single Domain Antibody Fc Fusion Protein in Humanized Mice CTLA4 humanized mice (i.e., mice expressing human CTLA4 protein) were inoculated with 5×10$^5$ MC38 tumor cells.

On day 7, 10, 13, and 16 post inoculation, 100 μg of the test sample or the same amount of human immunoglobulin (as a control group) was intraperitoneally administered. Tumor sizes were measured every two days from day 5 post inoculation until day 20. The samples examined included the tetravalent CTLA4 single domain antibody Fc fusion protein (Tet in the figure) and the CTLA4 monoclonal antibody, ipilimumab, which has been marketed by BMS.

From the results shown in the figure below, the anti-tumor effect of the tetravalent CTLA4 single domain antibody Fc fusion protein in CTLA4 humanized mice was comparable to that of BMS ipilimumab at a dose of about 5 mg/kg.

Example 6: Pharmacokinetics of CTLA4 Single Domain Antibody Fc Fusion Protein in Rats CTLA4 single domain antibody Fc fusion protein was single intravenously (IV) administrated to SD rats, the blood sample was collected at different time points, and Elisa assay was used to determine the concentration of the test substance in the plasma of the rats after administration of the test substance. The pharmacokinetic parameters were calculated.

Animal selection: SD rats aged 6-8 weeks and weighed 200-300 g were selected. They were randomly assigned to two groups, 8 rats each group, half male and half female.

Administration: Single intravenous (IV) administration at a dose of 10 mg/kg.

Blood collection: Before administration, immediately after administration, at various time points after administration, about 0.5 ml of blood was collected each time from the jugular vein of each rat. The collected blood was quickly centrifuged to separate the serum which was stored at −80° C. until analysis.

Blood drug concentration detection: The content of CTLA4 single domain antibody Fc fusion protein in serum was detected by sandwich ELISA. The plate was coated with recombinant human CTLA4 protein to capture CTLA4-specific antibodies, and the Fc region was detected with goat anti-human IgG (Fc specific)-HRP antibody (Sigma) to ensure the detection of intact CTLA4 single domain antibody Fc fusion protein.

Data processing: relevant pharmacokinetic parameters were calculated using blood drug concentration versus time curve, including AUC (0-t), AUC (0-∞), Cmax, Tmax, T½, Vss, MRT, and so on.

Figure 16A:
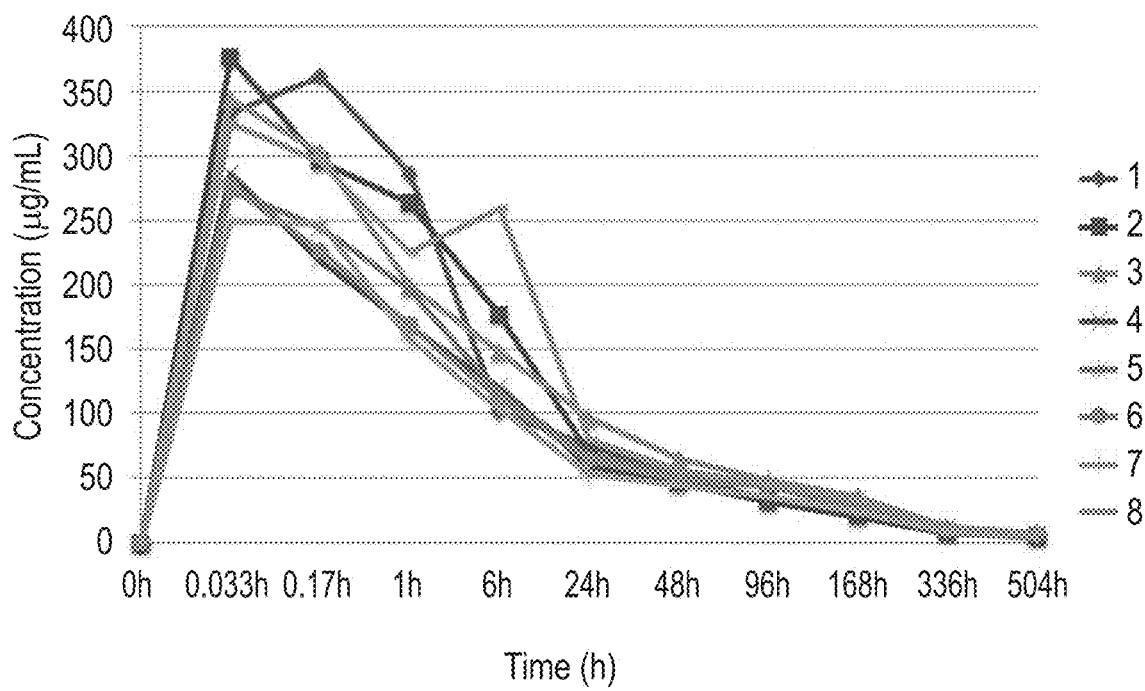
FIGS. 16A and 16B. shows change curves of the plasma concentration of bivalent and tetravalent CTLA4 single domain antibody-Fc fusion proteins in rats over time.
Figure 16B:
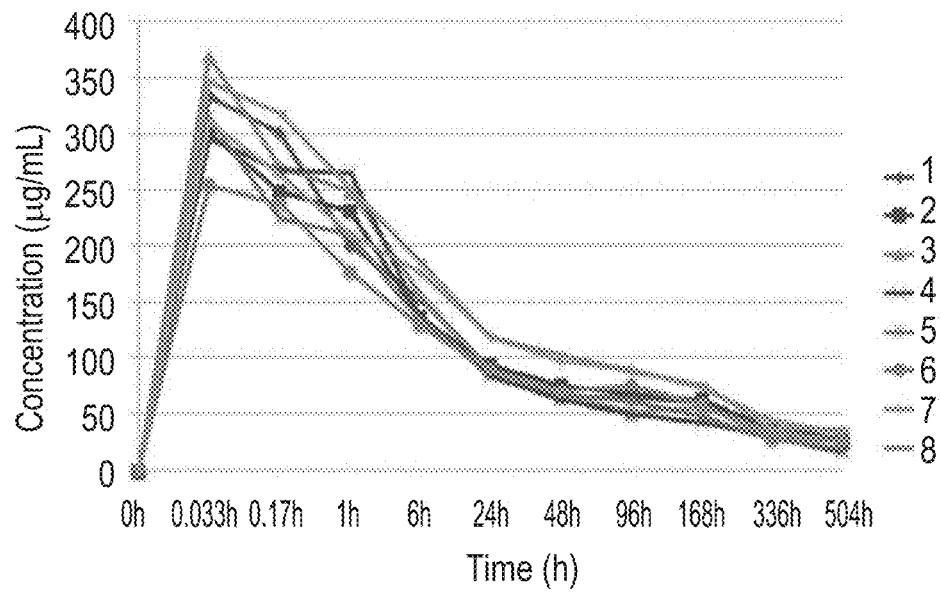
Figure 18:
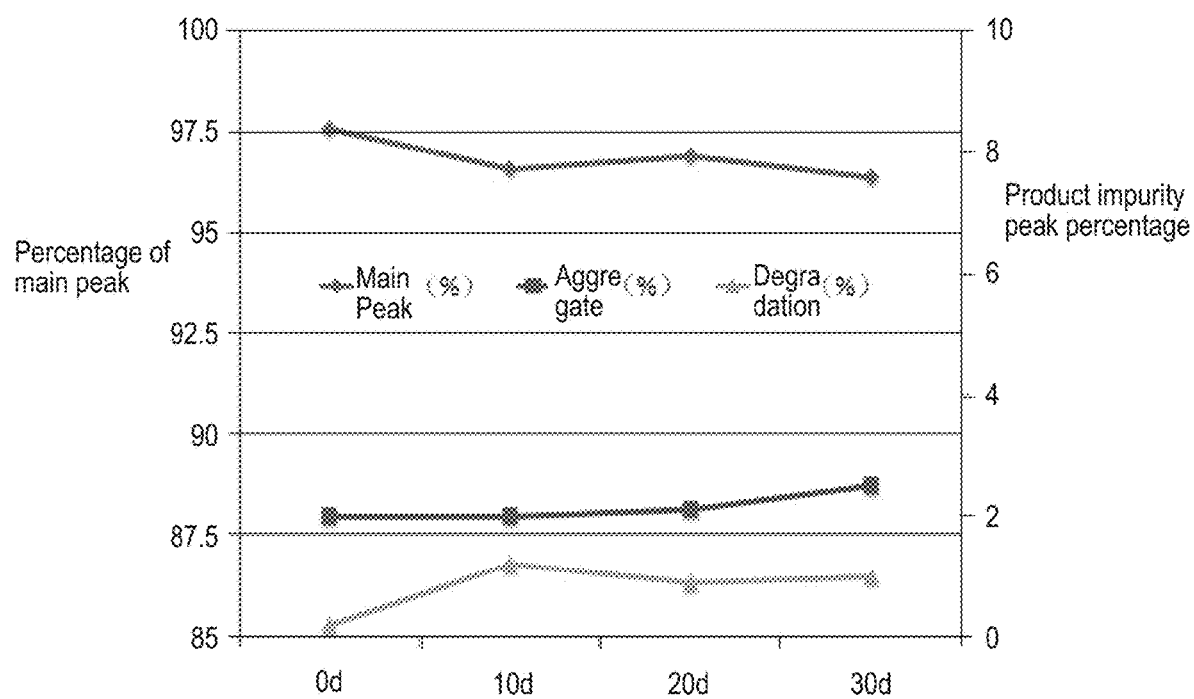
FIG. 18. shows the heat stability of CTLA4 single domain antibody-Fc fusion proteins.

The curves of blood drug concentration versus time of the bivalent and tetravalent CTLA4 single domain antibody Fc fusion protein in rats are shown in FIG. 16 (a is the bivalent antibody huC1v4-Ld-Fc, and b is the tetravalent antibody huC1v4-tet-Fc). The pharmacokinetic parameters are shown in FIG. 17. The results showed that both the bivalent or tetravalent CTLA4 single domain antibody Fc fusion protein had a longer in vivo half-life in rats (more than 5 days), indicating good in vivo stability. At the same time, in the case of maintaining the highest blood concentration, the tetravalent antibody had an in vivo half-life that is doubled (more than 11 days). It is thus concluded that the maintenance of the effective blood concentration of the tetravalent antibody in vivo is longer, and it is expected that the clinical administration can have a longer interval.

Example 7: Evaluation of the Druggability of CTLA4 Single Domain Antibody Fc Fusion Protein 7.1 Physicochemical Properties of CTLA4 Single Domain Antibody Fc Fusion Protein The affinity purified tetravalent CTLA4 single domain antibody Fc fusion protein expressed by human 293HEK cells was obtained by the method described in Example 4.4. Then its druggability was assessed by preliminary physical and chemical properties analysis through SE-HPLC, CE under reducing conditions, CE, WCX, DSC under non-reducing conditions. The specific values are set forth in the following table. From these data, it can be preliminarily determined that the tetravalent CTLA4 single domain antibody Fc fusion protein has good physical and chemical properties and is suitable for industrial scale production.

TABLE 6

| Protein Name | Expression Level | SE-HPLC purity(%) | SE-HPLC polymer content(%) | DSC(single-domain antibody, Tm, ° C.) | CE reduction % | CE non-reduction % | Deamination % |
|---|---|---|---|---|---|---|---|
| HuC1v4-tet-Fc | ~400 mg/L | 97.6 | 2.0 | 71.5 | 99.3 | 97.9 | 7 |

7.2 Thermal Destruction Test of CTLA4 Single Domain Antibody Fc Fusion Protein

The CTLA4 single domain antibody Fc fusion protein was concentrated by UF/DF and exchanged into PBS buffer to prepare a 20 mg/mL solution, and the thermal destruction test was performed with accelerating at 40° C. for 30 days. Samples of day 0, 10, 20, and 30 were tested for purity by SE-HPLC, and the change trend is shown in the following figure. It can be seen that at 40° C., without optimization of the preparation, although the purity of the main peak was slightly decreased, no obvious tendency of aggregation or degradation was observed. At the same time, considering its higher Tm value, it can be determined that the protein has good thermal stability.

Example 8: Evaluation of Preliminary Toxicity of CTLA4 Single Domain Antibody Fc Fusion Protein Four cynomolgus monkeys were randomly divided into two groups, two in each group, half male and half female, as the low and high dose groups respectively (7.5 and 30 mg/kg, respectively). Tetravalent CTLA4 single domain antibody Fc fusion protein was administered once via a posterior limb vein bolus. Before administration (D-1), D15 and D29 post administration, the indexes of body weight, blood cell count, blood coagulation function, blood biochemistry and immunogenicity were detected.

During the test, four animals showed no death or impending death. As for cynomolgus monkeys received single dose 7.5-30 mpk, significantly increases of hematological indexes lymph, Eos, Baso, Mono were observed. Clinical observation, weight, coagulation function, blood biochemical indicators of other groups of animals did not show changes with toxicological significance.

Thus, a single intravenous injection to cynomolgus monkeys at 7.5 and 30 mpk showed no significant toxicity, with NOAEL greater than or equal to 30 mg/kg. The non-clinical NOAEL reported for ipilimumab of BMS is approximately 10 mg/kg. It can be determined that the CTLA4 single domain antibody Fc fusion protein has lower toxic side effects than ipilimumab.

What is claimed is:

1. A CTLA4-binding protein, which can specifically bind to CTLA4 and comprises at least one immunoglobulin single variable domain, said immunoglobulin single variable domain is a humanized VHH comprising the amino acid sequence of SEQ ID NO: 106, SEQ ID NO: 107, SEQ ID NO: 108, or SEQ ID NO: 109.

2. The CTLA4-binding protein of claim 1, which comprises two said immunoglobulin single variable domain.

3. The CTLA4-binding protein of claim 1, which further comprises an immunoglobulin Fc region.

4. The CTLA4-binding protein of claim 3, wherein the immunoglobulin Fc region is an Fc region of human immunoglobulin, preferably an Fc region of human IgG1.

5. The CTLA4-binding protein of claim 4, wherein the amino acid sequence of the immunoglobulin Fc region is set forth in SEQ ID NO: 132.

6. The CTLA4-binding protein of claim 3, which comprises the amino acid sequence of SEQ ID NO: 123, SEQ ID NO: 124, SEQ ID NO: 125, or SEQ ID NO: 126 or 128.

7. The CTLA4-binding protein of claim 1, which has at least one of the following features:
 (a) binding to human CTLA4 with a KD of less than $1\times10^{-7}$ M; ;
 (b) blocking the interaction of CTLA4 with CD80 and/or CD86;
 (c) enhancing activation of PBMCs and/or T cells;
 (d) inhibiting tumor growth.

8. The CTLA4-binding protein of claim 1, which binds to CTLA4 with a KD of less than $1\times10^{-7}$ M, preferably less than $1\times10^{-9}$ M, more preferably less than $1\times10^{31\ 9}$ M, more preferably less than $1\times10^{-10}$ M.

9. A pharmaceutical composition comprising the CTLA4-binding protein of claim 1, and a pharmaceutically acceptable carrier.

* * * * *

SEQUENCE LISTING

```
<160> NUMBER OF SEQ ID NOS: 133

<210> SEQ ID NO 1
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 1

Ser Tyr Thr Met Thr
1               5

<210> SEQ ID NO 2
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 2

Ser Thr Ile Asn Ser Gly Gly Ser Thr Ser Tyr Ala Asp Ser Val Lys
1               5                   10                  15

Gly

<210> SEQ ID NO 3
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 3

Gly Leu Thr
1
```

```
<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Thr Asn Cys Met Gly
1               5

<210> SEQ ID NO 5
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 5

Val Met Asn Pro Ser Gly Gly Val Thr Tyr Phe Ala Asp Ser Val Lys
1               5                   10                  15

Gly

<210> SEQ ID NO 6
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 6

Gly Arg Gly Arg Cys Ser Gly Tyr Ser Gly Tyr Tyr Asn Glu
1               5                   10

<210> SEQ ID NO 7
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 7

Thr Ser Cys Met Gly
1               5

<210> SEQ ID NO 8
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 8

Thr Val Asn Lys Val Gly Ser Thr Ile Tyr Ala Asp Ser Val Lys Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: Synthetic Polypeptide
```

-continued

<400> SEQUENCE: 9

Arg Gly Ser Trp Ser Cys Ser Gln Phe Trp Gly Asp Phe Gly Tyr
1               5                   10                  15

<210> SEQ ID NO 10
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 10

Asn Thr Cys Met Gly
1               5

<210> SEQ ID NO 11
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 11

Ala Ile Ser Gly Val Gly Thr Gly Thr Tyr Tyr Ala Asp Ser Val Lys
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 12

Ala Pro Glu Gly Arg Ala Trp Cys Ser Arg Asp Pro Ser Gly Tyr Asn
1               5                   10                  15

Tyr

<210> SEQ ID NO 13
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 13

Ser Tyr Ser Met Gly
1               5

<210> SEQ ID NO 14
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 14

Ala Ile Asp Ser Asp Gly Ser Thr Ser Tyr Ala Asp Ser Val Lys Gly
1               5                   10                  15

<210> SEQ ID NO 15
<211> LENGTH: 18
<212> TYPE: PRT

```
<213> ORGANISM: Artificial Sequence
<220> FEATURE:
<223> OTHER INFORMATION: Synthetic Polypeptide

<400> SEQUENCE: 15

Thr Ala Gly Trp Tyr Ala Ala Arg His Ala Leu Ser Pro Leu Phe Phe
1               5                   10                  15

Gly Tyr

<210> SEQ ID NO 16
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 16

Gly Ser Cys Met Gly
1               5

<210> SEQ ID NO 17
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 17

Ala Met Phe Thr Gly Thr Gly Ser Thr Tyr Tyr Ala Asp Ser Val Lys
1               5                   10                  15

Gly

<210> SEQ ID NO 18
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 18

Asp Leu Leu Pro Arg Ser Thr Arg Cys Leu Asp Tyr Gly Leu Arg Thr
1               5                   10                  15

Tyr Asn Tyr

<210> SEQ ID NO 19
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 19

Arg Lys Cys Met Gly
1               5

<210> SEQ ID NO 20
<211> LENGTH: 17
<212> TYPE: PRT
<213> ORGANISM: Artificial Sequence
<220> FEATURE:
<223> OTHER INFORMATION: Synthetic Polypeptide
```

```
<400> SEQUENCE: 20

Thr Phe Tyr Thr Gly Asp Gly Arg Thr Tyr Tyr Ala Asp Ser Val Lys
1               5                   10                  15

Gly

<210> SEQ ID NO 21
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 21

Asp Arg Arg Val Asn Cys Asp Leu Leu Gln Ser Thr Phe Tyr Asn Tyr
1               5                   10                  15

<210> SEQ ID NO 22
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 22

Ser Val Cys Met Gly
1               5

<210> SEQ ID NO 23
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 23

Gly Ile Asp Gly Asp Gly Ile Thr Met Tyr Ala Asn Ser Val Lys Gly
1               5                   10                  15

<210> SEQ ID NO 24
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 24

Gly Gly Gln Gly Asp Gly Ser Cys Ala Leu Thr Tyr
1               5                   10

<210> SEQ ID NO 25
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 25

Ala Tyr Cys Met Gly
1               5

<210> SEQ ID NO 26
<211> LENGTH: 17
<212> TYPE: PRT
<213> ORGANISM: Artificial Sequence
<220> FEATURE:
```

<223> OTHER INFORMATION: Synthetic Polypeptide

<400> SEQUENCE: 26

Ala Ile Tyr Leu Gly Gly Gly Ser Thr Tyr Tyr Ala Asp Ser Val Lys
1               5                   10                  15
Gly

<210> SEQ ID NO 27
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 27

Asp Val Ile Pro Thr Glu Thr Cys Leu Gly Gly Ser Trp Ser Gly Pro
1               5                   10                  15
Phe Gly Tyr

<210> SEQ ID NO 28
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 28

Gly Tyr Cys Met Ala
1               5

<210> SEQ ID NO 29
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 29

Ser Ile His Arg Arg Asp Gly Ser Thr Asp Tyr Ala Asp Ser Val Lys
1               5                   10                  15
Gly

<210> SEQ ID NO 30
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 30

Asp Pro Ala Arg Leu Ser Cys Ser Gly Arg Val Asn Ser Glu Tyr Lys
1               5                   10                  15
Tyr

<210> SEQ ID NO 31
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 31

Gly Asp Leu Val Ala
1               5

<210> SEQ ID NO 32
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 32

Ala Ile Ser Arg Thr Gly Leu Thr Thr Tyr Tyr Ala Asp Ser Val Lys
1               5                   10                  15

Gly

<210> SEQ ID NO 33
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 33

Gly Trp His Val Gly Gly Thr Trp Tyr Lys Thr Ser Ser Tyr Asp Tyr
1               5                   10                  15

<210> SEQ ID NO 34
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 34

Tyr Tyr Tyr Met Ala
1               5

<210> SEQ ID NO 35
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 35

Ser Ile Trp Thr Gly Gly Thr Pro Gly Tyr Ala Asp Ser Ala Lys
1               5                   10                  15

Gly

<210> SEQ ID NO 36
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 36

Asp Asp Arg Gly Gly Arg Trp Ser Leu Gly Thr Met Ala Val Gly Gly
1               5                   10                  15

Tyr Lys Tyr

<210> SEQ ID NO 37
<211> LENGTH: 5
<212> TYPE: PRT
<213> ORGANISM: Artificial Sequence
<220> FEATURE:
<223> OTHER INFORMATION: Synthetic Polypeptide

```
<400> SEQUENCE: 37

Ala Tyr Cys Met Gly
1               5

<210> SEQ ID NO 38
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 38

Ala Ile Ser Ile Gly Gly Gly Ser Thr Tyr Tyr Ala Asp Ser Val Lys
1               5                   10                  15
Gly

<210> SEQ ID NO 39
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 39

Asp Val Ile Pro Thr Glu Thr Cys Leu Gly Gly Ser Trp Ser Gly Pro
1               5                   10                  15
Phe Gly Tyr

<210> SEQ ID NO 40
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 40

Gly Tyr Cys Met Gly
1               5

<210> SEQ ID NO 41
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 41

Ala Ile Ser Arg Gly Asp Gly Ser Pro Gly Tyr Ala Asp Ser Val Lys
1               5                   10                  15
Gly

<210> SEQ ID NO 42
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 42

Asp Val Ile Pro Thr Glu Thr Cys Ser Tyr Gly Ser Trp Ser Gly Pro
1               5                   10                  15
Asn Gly Tyr
```

<210> SEQ ID NO 43
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 43

Ser Asn Cys Met Ala
1               5

<210> SEQ ID NO 44
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 44

Thr Ile Tyr Asn Gly Gly Ser Thr Ala Tyr Ala Asp Ser Val Lys
1               5                   10                  15

Gly

<210> SEQ ID NO 45
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 45

Gly Ser Pro Arg Phe Cys Ala Ser Ala Thr Met Thr Gly Gly His His
1               5                   10                  15

Leu Phe Gly Tyr
            20

<210> SEQ ID NO 46
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 46

Thr Tyr Cys Met Ala
1               5

<210> SEQ ID NO 47
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 47

Ser Ile Tyr Thr Gly Gly Gly Thr Thr Tyr Tyr Ala Asp Ser Val Lys
1               5                   10                  15

Gly

<210> SEQ ID NO 48
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 48

Ser Ala Ala Arg Cys Asp Ser Ser Arg Asp Val Asn Arg Leu Gly Tyr
1               5                   10                  15

<210> SEQ ID NO 49
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 49

Ser Tyr Thr Met Thr
1               5

<210> SEQ ID NO 50
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 50

Thr Ile Asn Ser Gly Gly Ser Thr Ser Tyr Ala Asp Ser Val Lys Gly
1               5                   10                  15

<210> SEQ ID NO 51
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 51

Gly Leu Thr Gln
1

<210> SEQ ID NO 52
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 52

Ser Tyr Thr Met Thr
1               5

<210> SEQ ID NO 53
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 53

Thr Ile Asn Ser Gly Gly Ser Thr Ala Tyr Ala Asp Ser Val Lys Gly
1               5                   10                  15

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide

```
<400> SEQUENCE: 54

Gly Leu Thr Gln
1

<210> SEQ ID NO 55
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 55

Tyr Tyr Val Met Gly
1               5

<210> SEQ ID NO 56
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 56

Ser Ile Asp Ser Asn Gly Gly Thr Met Tyr Ala Asp Ser Val Lys Gly
1               5                   10                  15

<210> SEQ ID NO 57
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 57

Asp Ser Pro Gly Asn Phe Tyr
1               5

<210> SEQ ID NO 58
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 58

Pro His Cys Met Gly
1               5

<210> SEQ ID NO 59
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 59

Ala Ile Tyr Asn Gly Gly Gly Ser Thr Ala Tyr Ala Asp Ser Val Lys
1               5                   10                  15

Gly

<210> SEQ ID NO 60
<211> LENGTH: 20
<212> TYPE: PRT
<213> ORGANISM: Artificial Sequence
<220> FEATURE:
<223> OTHER INFORMATION: Synthetic Polypeptide
```

```
<400> SEQUENCE: 60

Gly Ser Pro Arg Phe Cys Ala Ser Ala Thr Met Thr Gly Gly His His
1               5                   10                  15

Leu Phe Gly Tyr
            20

<210> SEQ ID NO 61
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 61

Gly Ala Leu Met Gly
1               5

<210> SEQ ID NO 62
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 62

Val Ile Ser Arg Ser Gly Leu Thr Thr Tyr Tyr Ala Asp Ser Val Lys
1               5                   10                  15

Gly

<210> SEQ ID NO 63
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 63

Gly Trp His Val Gly Gly Thr Trp Ser Glu Thr Ser Ser Tyr Asp Tyr
1               5                   10                  15

<210> SEQ ID NO 64
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 64

Gly Ala Leu Met Gly
1               5

<210> SEQ ID NO 65
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 65

Val Ile Ser Arg Ser Gly Leu Thr Thr Tyr Tyr Ala Asp Ser Val Lys
1               5                   10                  15

Gly
```

```
<210> SEQ ID NO 66
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 66

Ala Pro Glu Ala Arg Ala Trp Ser Ser Arg Asp Pro Thr Gly Tyr Asn
1               5                   10                  15

Tyr

<210> SEQ ID NO 67
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 67

Ser Asn Cys Met Gly
1               5

<210> SEQ ID NO 68
<211> LENGTH: 16
<212> TYPE: PRT
<213> ORGANISM: Artificial Sequence
<220> FEATURE:
<223> OTHER INFORMATION: Synthetic Polypeptide

<400> SEQUENCE: 68

Ala Ile Asp Ser Asp Gly Ser Thr Ser Tyr Ala Asp Ser Val Lys Gly
1               5                   10                  15

<210> SEQ ID NO 69
<211> LENGTH: 19
<212> TYPE: PRT
<213> ORGANISM: Artificial Sequence
<220> FEATURE:
<223> OTHER INFORMATION: Synthetic Polypeptide

<400> SEQUENCE: 69

Ser Pro Arg Thr Cys Glu Val Phe Ser Leu Gly Gly Ser Trp His Leu
1               5                   10                  15

Phe Gly Tyr

<210> SEQ ID NO 70
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 70

Ser Tyr Ser Met Thr
1               5

<210> SEQ ID NO 71
<211> LENGTH: 16
<212> TYPE: PRT
<213> ORGANISM: Artificial Sequence
<220> FEATURE:
<223> OTHER INFORMATION: Synthetic Polypeptide
```

<400> SEQUENCE: 71

Thr Ile Asn Ser Gly Gly Ser Thr Ser Tyr Ala Asp Ser Val Lys Gly
1               5                   10                  15

<210> SEQ ID NO 72
<211> LENGTH: 3
<212> TYPE: PRT
<213> ORGANISM: Artificial Sequence
<220> FEATURE:
<223> OTHER INFORMATION: Synthetic Polypeptide

<400> SEQUENCE: 72

Gly Leu Thr
1

<210> SEQ ID NO 73
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 73

Tyr Tyr Tyr Met Ala
1               5

<210> SEQ ID NO 74
<211> LENGTH: 17
<212> TYPE: PRT
<213> ORGANISM: Artificial Sequence
<220> FEATURE:
<223> OTHER INFORMATION: Synthetic Polypeptide

<400> SEQUENCE: 74

Ser Ile Trp Thr Gly Gly Gly Thr Pro Gly Tyr Ala Asp Ser Ala Lys
1               5                   10                  15

Gly

<210> SEQ ID NO 75
<211> LENGTH: 18
<212> TYPE: PRT
<213> ORGANISM: Artificial Sequence
<220> FEATURE:
<223> OTHER INFORMATION: Synthetic Polypeptide

<400> SEQUENCE: 75

Asp Arg Gly Gly Arg Trp Ser Leu Gly Thr Met Ala Val Gly Gly Tyr
1               5                   10                  15

Lys Tyr

<210> SEQ ID NO 76
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 76

Gln Val Gln Leu Gln Glu Ser Gly Gly Gly Leu Val Gln Pro Gly Gly
1               5                   10                  15

Ser Leu Arg Leu Ser Cys Glu Ala Ser Gly Phe Thr Phe Ser Ser Tyr
            20                  25                  30

Thr Met Thr Trp Leu Arg Gln Ala Pro Gly Lys Gly Leu Glu Trp Val
            35                  40                  45

Ser Thr Ile Asn Ser Gly Gly Ser Thr Ser Tyr Ala Asp Ser Val Lys
 50                  55                  60

Gly Arg Phe Ala Ile Ser Arg Asp Asn Ala Lys Asn Thr Leu Tyr Leu
 65                  70                  75                  80

Gln Leu Asn Ser Leu Glu Ile Glu Asp Thr Gly Met Tyr Tyr Cys Gln
                 85                  90                  95

Gly Gly Leu Thr Arg Gly Gln Gly Thr Gln Val Thr Val Ser Ser
             100                 105                 110

<210> SEQ ID NO 77
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 77

Gln Val Gln Leu Gln Glu Ser Gly Gly Gly Ser Val Gln Ala Gly Gly
 1               5                  10                  15

Ser Leu Arg Leu Ser Cys Ala Ala Ser Glu Tyr Thr Tyr His Thr Asn
                 20                  25                  30

Cys Met Gly Trp Phe Arg Gln Ala Pro Gly Lys Glu Arg Glu Gly Leu
             35                  40                  45

Ala Val Met Asn Pro Ser Gly Gly Val Thr Tyr Phe Ala Asp Ser Val
 50                  55                  60

Lys Gly Arg Phe Thr Ile Ser Arg Asp Asn Ala Lys Asn Thr Val Tyr
 65                  70                  75                  80

Leu Gln Met Asn Ser Leu Lys Pro Glu Asp Thr Ala Met Tyr Tyr Cys
                 85                  90                  95

Ala Ala Gly Arg Gly Arg Cys Ser Gly Tyr Ser Gly Tyr Tyr Asn Glu
             100                 105                 110

Trp Gly Gln Gly Thr Gln Val Thr Val Ser Ser
         115                 120

<210> SEQ ID NO 78
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 78

Gln Val Gln Leu Gln Glu Ser Gly Gly Gly Ser Val Gln Ala Gly Gly
 1               5                  10                  15

Ser Leu Lys Leu Ser Cys Ala Ala Ser Gly Tyr Thr Asp Tyr Thr Tyr
                 20                  25                  30

Asn Thr Ser Cys Met Gly Trp Phe Arg Gln Thr Pro Gly Lys Glu Arg
             35                  40                  45

Glu Arg Val Ala Thr Val Asn Lys Val Gly Ser Thr Ile Tyr Ala Asp
 50                  55                  60

Ser Val Lys Gly Arg Phe Thr Ile Ser Lys Asp Asn Val Lys Asn Thr
 65                  70                  75                  80

Leu Tyr Leu Gln Met Asn Ser Leu Lys Pro Glu Asp Thr Ala Met Tyr
                 85                  90                  95

```
Tyr Cys Ala Ala Arg Gly Ser Trp Ser Cys Ser Gln Phe Trp Gly Asp
                100                 105                 110

Phe Gly Tyr Trp Gly Gln Gly Thr Gln Val Thr Val Ser Ser
        115                 120                 125
```

<210> SEQ ID NO 79
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 79

```
Gln Val Gln Leu Gln Glu Ser Gly Gly Gly Ser Val Gln Ala Gly Gly
1               5                   10                  15

Ser Leu Thr Leu Ser Cys Ala Ala Ser Gly Tyr Ala Asn Ser Asn Thr
            20                  25                  30

Cys Met Gly Trp Phe Arg Gln Ala Pro Gly Lys Glu Arg Glu Arg Val
        35                  40                  45

Ala Ala Ile Ser Gly Val Gly Thr Gly Thr Tyr Tyr Ala Asp Ser Val
    50                  55                  60

Lys Gly Arg Phe Thr Ile Ser Arg Asp Asn Gly Lys Asn Thr Leu Phe
65                  70                  75                  80

Leu Gln Met Asn Ser Leu Lys Pro Glu Asp Thr Ala Met Tyr Tyr Cys
                85                  90                  95

Ala Ala Ala Pro Glu Gly Arg Ala Trp Cys Ser Arg Asp Pro Ser Gly
                100                 105                 110

Tyr Asn Tyr Trp Gly Gln Gly Thr Gln Val Thr Val Ser Ser
        115                 120                 125
```

<210> SEQ ID NO 80
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 80

```
Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Tyr
            20                  25                  30

Ser Met Gly Trp Phe Arg Gln Ala Ala Gly Lys Glu Arg Glu Gly Val
        35                  40                  45

Ala Ala Ile Asp Ser Asp Gly Ser Thr Ser Tyr Ala Asp Ser Val Lys
    50                  55                  60

Gly Arg Phe Thr Ile Ser Gln Asp Asn Ala Lys Asn Thr Leu Tyr Leu
65                  70                  75                  80

Gln Met Asn Ser Leu Glu Pro Glu Asp Thr Ala Met Tyr Tyr Cys Ala
                85                  90                  95

Ala Thr Ala Gly Trp Tyr Ala Ala Arg His Ala Leu Ser Pro Leu Phe
                100                 105                 110

Phe Gly Tyr Trp Gly Gln Gly Thr Gln Val Thr Val Ser Ser
        115                 120                 125
```

<210> SEQ ID NO 81
<211> LENGTH: 128
<212> TYPE: PRT

```
<213> ORGANISM: Artificial Sequence
<220> FEATURE:
<223> OTHER INFORMATION: Synthetic Polypeptide

<400> SEQUENCE: 81

Gln Val Gln Leu Gln Glu Ser Gly Gly Gly Pro Val Gln Ala Gly Gly
1               5                   10                  15

Ser Leu Arg Leu Ser Cys Ala Val Ser Lys Tyr Pro Tyr Ser Gly Ser
            20                  25                  30

Cys Met Gly Trp Phe Arg Gln Ala Pro Gly Lys Glu Arg Glu Gly Val
        35                  40                  45

Ala Ala Met Phe Thr Gly Thr Gly Ser Thr Tyr Tyr Ala Asp Ser Val
    50                  55                  60

Lys Gly Arg Phe Thr Ile Ser Gln Asn Val Lys Asn Thr Leu Asp
65                  70                  75                  80

Leu Gln Met Asn Ser Leu Lys Pro Glu Asp Thr Ala Met Tyr Tyr Cys
                85                  90                  95

Ala Val Asp Leu Leu Pro Arg Ser Thr Arg Cys Leu Tyr Gly Leu
            100                 105                 110

Arg Thr Tyr Asn Tyr Trp Gly Gln Gly Thr Gln Val Thr Val Ser Ser
        115                 120                 125

<210> SEQ ID NO 82
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 82

Gln Val Gln Leu Gln Glu Ser Gly Gly Gly Ser Val Gln Thr Gly Gly
1               5                   10                  15

Ser Leu Arg Leu Ser Cys Val Val Ser Gly His Ser Tyr Ser Arg Lys
            20                  25                  30

Cys Met Gly Trp Phe Arg Gln Ala Pro Gly Lys Glu Arg Glu Glu Val
        35                  40                  45

Ala Thr Phe Tyr Thr Gly Asp Gly Arg Thr Tyr Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Gly Met Tyr Phe Cys
                85                  90                  95

Ala Ala Asp Arg Arg Val Asn Cys Asp Leu Leu Gln Ser Thr Phe Tyr
            100                 105                 110

Asn Tyr Arg Gly Gln Gly Thr Gln Val Thr Val Ser Ser
        115                 120                 125

<210> SEQ ID NO 83
<211> LENGTH: 121
<212> TYPE: PRT
<213> ORGANISM: Artificial Sequence
<220> FEATURE:
<223> OTHER INFORMATION: Synthetic Polypeptide

<400> SEQUENCE: 83

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Val
            20                  25                  30
```

```
Cys Met Gly Trp Phe Arg Gln Ala Leu Gly Lys Glu Arg Glu Ala Val
            35                  40                  45

Val Gly Ile Asp Gly Asp Gly Ile Thr Met Tyr Ala Asn Ser Val Lys
 50                  55                  60

Gly Arg Phe Thr Ile Ser Lys Asp Asn Ala Lys Asn Thr Leu Tyr Leu
 65                  70                  75                  80

Gln Met Asn Ser Leu Lys Pro Glu Asp Thr Ala Met Tyr Tyr Cys Ala
                85                  90                  95

Ser Gly Gly Gln Gly Asp Gly Ser Cys Ala Leu Thr Tyr Trp Gly
               100                 105                 110

Gln Gly Thr Gln Val Thr Val Ser Ser
           115                 120
```

<210> SEQ ID NO 84
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 84

```
Gln Val Gln Leu Gln Glu Ser Gly Gly Gly Ser Val Gln Ala Gly Gly
 1               5                  10                  15

Ser Leu Gly Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Glu Gly Val
            35                  40                  45

Ala Ala Ile Tyr Leu Gly Gly Ser Thr Tyr Tyr Ala Asp Ser Val
 50                  55                  60

Lys Gly Arg Phe Thr Ile Ser Gln Asp Ile Ala Lys Asn Thr Leu Tyr
 65                  70                  75                  80

Leu Gln Met Asn Ser Leu Lys Pro Glu Asp Thr Ala Met Tyr Ser Cys
                85                  90                  95

Ala Ala Asp Val Ile Pro Thr Glu Thr Cys Leu Gly Gly Ser Trp Ser
               100                 105                 110

Gly Pro Phe Gly Tyr Trp Gly Gln Gly Thr Gln Val Thr Val Ser Ser
           115                 120                 125
```

<210> SEQ ID NO 85
<211> LENGTH: 126
<212> TYPE: PRT
<213> ORGANISM: Artificial Sequence
<220> FEATURE:
<223> OTHER INFORMATION: Synthetic Polypeptide

<400> SEQUENCE: 85

```
Gln Val Gln Leu Gln Glu Ser Gly Gly Gly Ser Val Gln Pro Gly Gly
 1               5                  10                  15

Ser Leu Arg Leu Ser Cys Ala Val Ser Gly Phe Thr Phe Ser Gly Tyr
                20                  25                  30

Cys Met Ala Trp Val Arg Gln Ala Pro Gly Lys Gly Leu Glu Trp Val
            35                  40                  45

Ala Ser Ile His Arg Arg Asp Gly Ser Thr Asp Tyr Ala Asp Ser Val
 50                  55                  60

Lys Gly Arg Phe Thr Ile Ser Lys Asp Asn Ser Lys Asn Thr Leu Tyr
 65                  70                  75                  80
```

```
Leu Gln Met Ser Ser Leu Lys Pro Glu Asp Thr Ala Val Tyr Tyr Cys
                85                  90                  95

Ala Ala Asp Pro Ala Arg Leu Ser Cys Ser Gly Arg Val Asn Ser Glu
            100                 105                 110

Tyr Lys Tyr Arg Gly Gln Gly Thr Gln Val Thr Val Ser Ser
        115                 120                 125

<210> SEQ ID NO 86
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 86

Gln Val Gln Leu Gln Glu Ser Gly Gly Gly Ser Val Gln Ala Gly Gly
1               5                   10                  15

Ser Leu Thr Leu Ser Cys Ala Ala Ser Gly Tyr Thr Gly Asp Leu Val
            20                  25                  30

Ala Trp Phe Arg Gln Thr Pro Gly Lys Glu Arg Glu Gly Val Ala Ala
        35                  40                  45

Ile Ser Arg Thr Gly Leu Thr Thr Tyr Tyr Ala Asp Ser Val Lys Gly
    50                  55                  60

Arg Phe Thr Ile Ser Gln Asp Thr Ala Lys Asn Thr Gly Tyr Leu Gln
65                  70                  75                  80

Met Asn Ser Met Lys Pro Glu Asp Thr Ala Met Tyr Tyr Cys Val Ala
                85                  90                  95

Gly Trp His Val Gly Gly Thr Trp Tyr Lys Thr Ser Ser Tyr Asp Tyr
            100                 105                 110

Trp Gly Gln Gly Thr Gln Val Thr Val Ser Ser
        115                 120

<210> SEQ ID NO 87
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 87

Gln Val Gln Leu Gln Glu Ser Gly Gly Gly Ser Val Gln Ala Gly Gly
1               5                   10                  15

Ser Leu Arg Leu Ser Cys Thr Val Ser Gln His Thr Ser Arg Tyr Tyr
            20                  25                  30

Tyr Met Ala Trp Phe Arg Gln Ala Pro Gly Lys Glu Arg Glu Gly Val
        35                  40                  45

Ala Ser Ile Trp Thr Gly Gly Thr Pro Gly Tyr Ala Asp Ser Ala
    50                  55                  60

Lys Gly Arg Phe Thr Ile Ser Thr Asp Asn Ala Lys Asn Thr Ile Tyr
65                  70                  75                  80

Leu Gln Met Asn Ser Leu Lys Pro Glu Asp Thr Ala Met Tyr Tyr Cys
                85                  90                  95

Ala Ala Asp Asp Arg Gly Gly Arg Trp Ser Leu Gly Thr Met Ala Val
            100                 105                 110

Gly Gly Tyr Lys Tyr Trp Gly Gln Gly Thr Gln Val Thr Val Ser Ser
        115                 120                 125
```

```
<210> SEQ ID NO 88
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 88

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Val Gly Val
            35                  40                  45

Ala Ala Ile Ser Ile Gly Gly Ser Thr Tyr Tyr Ala Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

<210> SEQ ID NO 89
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 89

Gln Val Gln Leu Gln Glu Ser Gly Gly Gly Ser Val Gln Ala Gly Gly
1               5                   10                  15

Ser Leu Arg Leu Ser Cys Ala Val Ser Gly Tyr Thr Tyr Ser Gly Tyr
                20                  25                  30

Cys Met Gly Trp Phe Arg Gln Ala Pro Gly Lys Glu Arg Glu Gly Val
            35                  40                  45

Ala Ala Ile Ser Arg Gly Asp Gly Ser Pro Gly Tyr Ala Asp Ser Val
        50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Val Ile Pro Thr Glu Thr Cys Ser Tyr Gly Ser Trp Ser
            100                 105                 110

Gly Pro Asn Gly Tyr Trp Gly Gln Gly Thr Gln Val Thr Val Ser Ser
        115                 120                 125

<210> SEQ ID NO 90
<211> LENGTH: 129
<212> TYPE: PRT
<213> ORGANISM: Artificial Sequence
<220> FEATURE:
<223> OTHER INFORMATION: Synthetic Polypeptide

<400> SEQUENCE: 90

Gln Val Gln Leu Gln Glu Ser Gly Gly Gly Ser Val Gln Ala Gly Gly
1               5                   10                  15
```

```
Ser Leu Arg Leu Ser Cys Ala Ala Ser Arg Tyr Thr Ala Ser Ser Asn
            20                  25                  30

Cys Met Ala Trp Phe Arg Gln Ala Pro Gly Lys Glu Arg Glu Gly Val
        35                  40                  45

Ala Thr Ile Tyr Asn Gly Gly Ser Thr Ala Tyr Ala Asp Ser Val
    50                  55                  60

Lys Gly Arg Phe Thr Ile Ser Gln Asp Asn Ala Lys Asn Thr Val Tyr
 65                  70                  75                  80

Leu Gln Met Asn Ser Leu Lys Pro Glu Asp Thr Ala Met Tyr Tyr Cys
                85                  90                  95

Gly Ala Gly Ser Pro Arg Phe Cys Ala Ser Ala Thr Met Thr Gly Gly
                100                 105                 110

His His Leu Phe Gly Tyr Trp Gly Gln Gly Thr Gln Val Thr Val Ser
            115                 120                 125

Ser

<210> SEQ ID NO 91
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 91

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Tyr Thr Tyr Ser Thr Tyr
            20                  25                  30

Cys Met Ala Trp Phe Arg Gln Val Pro Glu Lys Glu Arg Glu Arg Val
        35                  40                  45

Ala Ser Ile Tyr Thr Gly Gly Thr Thr Tyr Tyr Ala Asp Ser Val
    50                  55                  60

Lys Gly Arg Phe Thr Ile Ser Leu Asp Asn Ala Lys Asn Thr Leu Tyr
 65                  70                  75                  80

Leu Gln Met Asn Ser Leu Lys Pro Glu Asp Thr Ala Met Tyr Tyr Cys
                85                  90                  95

Ala Lys Ser Ala Ala Arg Cys Asp Ser Ser Arg Asp Val Asn Arg Leu
                100                 105                 110

Gly Tyr Trp Gly Gln Gly Thr Gln Val Thr Val Ser Ser
            115                 120                 125

<210> SEQ ID NO 92
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 92

Gln Val Gln Leu Gln Glu Ser Gly Gly Gly Ser Val Gln Ala Gly Gly
 1               5                  10                  15

Ser Leu Arg Leu Ser Cys Ala Ala Ser Gly Phe Thr Leu Ser Ser Tyr
            20                  25                  30

Thr Met Thr Trp Leu Arg Gln Ala Pro Gly Lys Gly Leu Glu Trp Val
        35                  40                  45

Ser Thr Ile Asn Ser Gly Gly Ser Thr Ser Tyr Ala Asp Ser Val Lys
    50                  55                  60
```

Gly Arg Phe Ala Ile Ser Arg Asp Asn Ala Lys Asn Ile Leu Tyr Leu
65                  70                  75                  80

Gln Leu Asn Ser Leu Glu Ile Glu Asp Thr Gly Met Tyr Tyr Cys Gln
            85                  90                  95

Gly Gly Leu Thr Gln Arg Gly Gln Gly Thr Gln Val Thr Val Ser Ser
        100                 105                 110

<210> SEQ ID NO 93
<211> LENGTH: 112
<212> TYPE: PRT
<213> ORGANISM: Artificial Sequence
<220> FEATURE:
<223> OTHER INFORMATION: Synthetic Polypeptide

<400> SEQUENCE: 93

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Ile Ser Ser Tyr
            20                  25                  30

Thr Met Thr Trp Leu His Gln Ala Pro Gly Lys Gly Leu Glu Trp Val
        35                  40                  45

Ser Thr Ile Asn Ser Gly Gly Ser Thr Ala Tyr Ala Asp Ser Val Lys
    50                  55                  60

Gly Arg Phe Ala Ile Ser Arg Asp Asn Ala Lys Asn Thr Leu Tyr Leu
65                  70                  75                  80

Gln Leu Asn Ser Leu Lys Ile Glu Asp Thr Gly Met Tyr Tyr Cys Gln
            85                  90                  95

Gly Gly Leu Thr Gln Arg Gly Gln Gly Thr Gln Val Thr Val Ser Ser
        100                 105                 110

<210> SEQ ID NO 94
<211> LENGTH: 115
<212> TYPE: PRT
<213> ORGANISM: Artificial Sequence
<220> FEATURE:
<223> OTHER INFORMATION: Synthetic Polypeptide

<400> SEQUENCE: 94

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Ser Gly Tyr Tyr
            20                  25                  30

Val Met Gly Trp Tyr Arg Gln Ala Pro Gly Lys Leu Arg Glu Phe Val
        35                  40                  45

Ser Ser Ile Asp Ser Asn Gly Gly Thr Met Tyr Ala Asp Ser Val Lys
    50                  55                  60

Gly Arg Phe Thr Ile Ser Gln Asp Asn Ala Lys Asn Thr Ala His Leu
65                  70                  75                  80

Gln Met Asn Ser Leu Lys Pro Glu Asp Thr Ala Met Tyr Tyr Cys Lys
            85                  90                  95

Arg Asp Ser Pro Gly Asn Phe Tyr Trp Gly Gln Gly Thr Gln Val Thr
        100                 105                 110

Val Ser Ser
        115

<210> SEQ ID NO 95
<211> LENGTH: 129
<212> TYPE: PRT

```
<213> ORGANISM: Artificial Sequence
<220> FEATURE:
<223> OTHER INFORMATION: Synthetic Polypeptide

<400> SEQUENCE: 95

Gln Val Gln Leu Gln Glu Ser Gly Gly Gly Ser Val Gln Ala Gly Gly
1               5                   10                  15

Thr Leu Arg Leu Ser Cys Ala Val Ser Gly Val Thr Tyr Ser Pro His
            20                  25                  30

Cys Met Gly Trp Phe Arg Gln Ala Pro Gly Lys Glu Arg Glu Gly Val
        35                  40                  45

Ala Ala Ile Tyr Asn Gly Gly Ser Thr Ala Tyr Ala Asp Ser Val
    50                  55                  60

Lys Gly Arg Phe Thr Ile Ser Gln Asp Asn Ala Lys Asn Thr Val Tyr
65                  70                  75                  80

Leu Gln Met Asn Ser Leu Lys Pro Glu Asp Thr Ala Met Tyr Tyr Cys
                85                  90                  95

Gly Ala Gly Ser Pro Arg Phe Cys Ala Ser Ala Thr Met Thr Gly Gly
            100                 105                 110

His His Leu Phe Gly Tyr Trp Gly Gln Gly Thr Gln Val Thr Val Ser
        115                 120                 125

Ser

<210> SEQ ID NO 96
<211> LENGTH: 123
<212> TYPE: PRT
<213> ORGANISM: Artificial Sequence
<220> FEATURE:
<223> OTHER INFORMATION: Synthetic Polypeptide

<400> SEQUENCE: 96

Gln Val Gln Leu Gln Glu Ser Gly Gly Gly Ser Val Gln Ala Gly Gly
1               5                   10                  15

Ser Leu Arg Leu Ser Cys Ala Pro Ser Arg Tyr Ser Gly Ala Leu Met
            20                  25                  30

Gly Trp Phe Arg Gln Ala Pro Gly Lys Glu Arg Glu Gly Val Ala Val
        35                  40                  45

Ile Ser Arg Ser Gly Leu Thr Thr Tyr Tyr Ala Asp Ser Val Lys Gly
    50                  55                  60

Arg Phe Thr Ile Ser Gln Asp Thr Ala Lys Asn Thr Ile Tyr Leu Gln
65                  70                  75                  80

Met Asn Ser Met Lys Pro Glu Asp Thr Ala Met Tyr Tyr Cys Val Ala
                85                  90                  95

Gly Trp His Val Gly Gly Thr Trp Ser Glu Thr Ser Ser Tyr Asp Tyr
            100                 105                 110

Trp Gly Gln Gly Thr Gln Val Thr Val Ser Ser
        115                 120

<210> SEQ ID NO 97
<211> LENGTH: 124
<212> TYPE: PRT
<213> ORGANISM: Artificial Sequence
<220> FEATURE:
<223> OTHER INFORMATION: Synthetic Polypeptide

<400> SEQUENCE: 97

Gln Val Gln Leu Gln Glu Ser Gly Gly Gly Ser Val Gln Ala Gly Gly
1               5                   10                  15
```

Ser Leu Arg Leu Ser Cys Ala Pro Ser Arg Tyr Ser Gly Ala Leu Met
            20                  25                  30

Gly Trp Phe Arg Gln Ala Pro Gly Lys Glu Arg Glu Gly Val Ala Val
            35                  40                  45

Ile Ser Arg Ser Gly Leu Thr Thr Tyr Ala Asp Ser Val Lys Gly
            50                  55                  60

Arg Phe Thr Ile Ser Gln Asp Thr Ala Lys Asn Thr Ile Tyr Leu Gln
65                  70                  75                  80

Met Asn Ser Met Lys Pro Glu Asp Thr Ala Met Tyr Tyr Cys Val Ala
            85                  90                  95

Ala Pro Glu Ala Arg Ala Trp Ser Ser Arg Asp Pro Thr Gly Tyr Asn
            100                 105                 110

Tyr Trp Gly Gln Gly Thr Gln Val Thr Val Ser Ser
            115                 120

<210> SEQ ID NO 98
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 98

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Thr Tyr Ser Ser Tyr
            20                  25                  30

Asn Ser Asn Cys Met Gly Trp Phe Arg Gln Ala Pro Gly Lys Glu Arg
            35                  40                  45

Glu Gly Val Ala Ala Ile Asp Ser Asp Gly Ser Thr Ser Tyr Ala Asp
            50                  55                  60

Ser Val Lys Gly Arg Phe Thr Ile Ser Lys Asp Asn Ala Lys Asn Thr
65                  70                  75                  80

Leu Tyr Leu Gln Met Asn Ser Leu Lys Pro Glu Asp Thr Ala Met Tyr
            85                  90                  95

Tyr Cys Ala Ala Ser Pro Arg Thr Cys Glu Val Phe Ser Leu Gly Gly
            100                 105                 110

Ser Trp His Leu Phe Gly Tyr Trp Gly Gln Gly Thr Gln Val Thr Val
            115                 120                 125

Ser Ser
    130

<210> SEQ ID NO 99
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 99

Gln Val Gln Leu Gln Glu Ser Gly Gly Gly Leu Val Gln Pro Gly Gly
1               5                   10                  15

Ser Leu Arg Leu Ser Cys Ala Ala Ser Gly Phe Thr Leu Ser Ser Tyr
            20                  25                  30

Ser Met Thr Trp Leu Arg Gln Ala Pro Gly Lys Gly Leu Glu Trp Val
            35                  40                  45

Ser Thr Ile Asn Ser Gly Gly Ser Thr Ser Tyr Ala Asp Ser Val Lys
            50                  55                  60

Gly Arg Phe Ala Ile Ser Arg Asp Asn Ala Lys Asn Thr Leu Tyr Leu
65                  70                  75                  80

Gln Leu Asn Ser Leu Glu Ile Glu Asp Thr Gly Met Tyr Tyr Cys Gln
                85                  90                  95

Gly Gly Leu Thr Arg Gly Gln Gly Thr Gln Val Thr Val Ser Ser
            100                 105                 110

<210> SEQ ID NO 100
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 100

Gln Val Gln Leu Gln Glu Ser Gly Gly Ser Val Gln Ala Gly Gly
1               5                   10                  15

Ser Leu Arg Leu Ser Cys Thr Val Ser Gln His Thr Ser Arg Tyr Tyr
                20                  25                  30

Tyr Met Ala Trp Phe Arg Gln Ala Pro Gly Lys Glu Arg Glu Gly Val
            35                  40                  45

Ala Ser Ile Trp Thr Gly Gly Thr Pro Gly Tyr Ala Asp Ser Ala
        50                  55                  60

Lys Gly Arg Phe Thr Ile Ser Ala Asp Asn Ala Lys Asn Thr Ile Tyr
65                  70                  75                  80

Leu Gln Met Asn Ser Leu Lys Pro Glu Asp Thr Ala Met Tyr Tyr Cys
                85                  90                  95

Ala Ala Asp Asp Arg Gly Gly Arg Trp Ser Leu Gly Thr Met Ala Val
            100                 105                 110

Gly Gly Tyr Lys Tyr Trp Gly Gln Gly Thr Gln Val Thr Val Ser Ser
        115                 120                 125

<210> SEQ ID NO 101
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 101

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
                20                  25                  30

Cys Met Gly Trp Phe Arg Gln Ala Pro Gly Lys Glu Arg Val Gly Val
            35                  40                  45

Ala Ala Ile Ser Ile Gly Gly Ser Thr Tyr Tyr Ala Asp Ser Val
        50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 102
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 102

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 103
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 103

```
Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 104
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 104

```
Gln Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

<210> SEQ ID NO 105
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 105

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
            115                 120                 125

<210> SEQ ID NO 106
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 106

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Ser Thr Tyr Tyr Ala Asp Ser Val
    50                  55                  60

```
Lys Gly Arg Phe Thr Ile Ser Gln Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 107
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 107

Gln Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ile Tyr Ser Ala Tyr
                 20                  25                  30

Cys Met Gly Trp Phe Arg Gln Ala Pro Gly Lys Glu Arg Glu Gly Val
             35                  40                  45

Ala Ala Ile Tyr Ile Gly Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

<210> SEQ ID NO 108
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 108

Gln Val Gln Leu Val Glu Ser Gly Gly Gly Leu Val Gln Pro Gly Gly
  1               5                  10                  15

Ser Leu Arg Leu Ser Cys Ala Ala Ser Gly Tyr Ile Tyr Ser Ala Tyr
                 20                  25                  30

Cys Met Gly Trp Phe Arg Gln Ala Pro Gly Lys Gly Leu Val Gly Val
             35                  40                  45

Ala Ala Ile Tyr Ile Gly Gly Gly Ser Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Ala Asp Val Ile Pro Thr Glu Thr Cys Leu Gly Gly Ser Trp Ser
            100                 105                 110
```

```
Gly Pro Phe Gly Tyr Trp Gly Gln Gly Thr Leu Val Thr Val Ser Ser
        115                 120                 125
```

<210> SEQ ID NO 109
<211> LENGTH: 128
<212> TYPE: PRT
<213> ORGANISM: Artificial Sequence
<220> FEATURE:
<223> OTHER INFORMATION: Synthetic Polypeptide

<400> SEQUENCE: 109

```
Gln Val Gln Leu Val Glu Ser Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Ser Trp Ser
            100                 105                 110

Gly Pro Phe Gly Tyr Trp Gly Gln Gly Thr Leu Val Thr Val Ser Ser
        115                 120                 125
```

<210> SEQ ID NO 110
<211> LENGTH: 24
<212> TYPE: DNA
<213> ORGANISM: Artificial Sequence
<220> FEATURE:
<223> OTHER INFORMATION: Synthetic Polypeptide

<400> SEQUENCE: 110
gtcctggctg ctcttctaca aggc                                              24

<210> SEQ ID NO 111
<211> LENGTH: 23
<212> TYPE: DNA
<213> ORGANISM: Artificial Sequence
<220> FEATURE:
<223> OTHER INFORMATION: Synthetic Polypeptide

<400> SEQUENCE: 111
ggtacgtgct gttgaactgt tcc                                               23

<210> SEQ ID NO 112
<211> LENGTH: 29
<212> TYPE: DNA
<213> ORGANISM: Artificial Sequence
<220> FEATURE:
<223> OTHER INFORMATION: Synthetic Polypeptide

<400> SEQUENCE: 112
gatgtgcagc tgcaggagtc tggrggagg                                         29

<210> SEQ ID NO 113
<211> LENGTH: 35
<212> TYPE: DNA
<213> ORGANISM: Artificial Sequence
<220> FEATURE:
<223> OTHER INFORMATION: Synthetic Polypeptide

<400> SEQUENCE: 113
ggactagtgc ggccgctgga gacggtgacc tgggt          35

<210> SEQ ID NO 114
<211> LENGTH: 362
<212> TYPE: PRT
<213> ORGANISM: Artificial Sequence
<220> FEATURE:
<223> OTHER INFORMATION: Synthetic Polypeptide

<400> SEQUENCE: 114

Gln Val Gln Leu Gln Glu Ser Gly Gly Gly Ser Val Gln Ala Gly Gly
1               5                   10                  15

Ser Leu Gly Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Leu Gly Gly Ser Thr Tyr Tyr Ala Asp Ser Val
    50                  55                  60

Lys Gly Arg Phe Thr Ile Ser Gln Asp Ile Ala Lys Asn Thr Leu Tyr
65                  70                  75                  80

Leu Gln Met Asn Ser Leu Lys Pro Glu Asp Thr Ala Met Tyr Ser Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

Gly Ser Glu Pro Lys Ser Cys Asp Lys Thr His Thr Cys Pro Pro Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
                340                 345                 350

Gln Lys Ser Leu Ser Leu Ser Pro Gly Lys
        355                 360

<210> SEQ ID NO 115
<211> LENGTH: 362
<212> TYPE: PRT
<213> ORGANISM: Artificial Sequence
<220> FEATURE:
<223> OTHER INFORMATION: Synthetic Polypeptide

<400> SEQUENCE: 115

Gln Val Gln Leu Gln Glu Ser Gly Gly Gly Ser Val Gln Ala Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Gln Asp Asn Ala Lys Asn Thr Leu Tyr
65                  70                  75                  80

Leu Gln Met Asn Ser Leu Lys Pro Glu Asp Thr Ala Met Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Gln Val Thr Val Ser Ser
        115                 120                 125

Gly Ser Glu Pro Lys Ser Cys Asp Lys Thr His Thr Cys Pro Pro Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

```
Val Phe Ser Cys Ser Val Met His Glu Ala Leu His Asn His Tyr Thr
                340                 345                 350
Gln Lys Ser Leu Ser Leu Ser Pro Gly Lys
        355                 360

<210> SEQ ID NO 116
<211> LENGTH: 360
<212> TYPE: PRT
<213> ORGANISM: Artificial Sequence
<220> FEATURE:
<223> OTHER INFORMATION: Synthetic Polypeptide

<400> SEQUENCE: 116

Gln Val Gln Leu Gln Glu Ser Gly Gly Gly Val Gln Ala Gly Gly
1               5                   10                  15

Ser Leu Arg Leu Ser Cys Ala Ala Ser Gly Tyr Thr Tyr Ser Ser Tyr
                20                  25                  30

Ser Met Gly Trp Phe Arg Gln Ala Ala Gly Lys Glu Arg Glu Gly Val
                35                  40                  45

Ala Ala Ile Asp Ser Asp Gly Ser Thr Ser Tyr Ala Asp Ser Val Lys
        50                  55                  60

Gly Arg Phe Thr Ile Ser Gln Asp Asn Ala Lys Asn Thr Leu Tyr Leu
65                  70                  75                  80

Gln Met Asn Ser Leu Glu Pro Glu Asp Thr Ala Met Tyr Tyr Cys Ala
                85                  90                  95

Ala Thr Ala Gly Trp Tyr Ala Ala Arg His Ala Leu Ser Pro Leu Phe
                100                 105                 110

Phe Gly Tyr Trp Gly Gln Gly Thr Gln Val Thr Val Ser Ser Gly Ser
                115                 120                 125

Glu Pro Lys Ser Cys Asp Lys Thr His Thr Cys Pro Pro Cys Pro Ala
        130                 135                 140

Pro Glu Leu Leu Gly Gly Pro Ser Val Phe Leu Phe Pro Pro Lys Pro
145                 150                 155                 160

Lys Asp Thr Leu Met Ile Ser Arg Thr Pro Glu Val Thr Cys Val Val
                165                 170                 175

Val Asp Val Ser His Glu Asp Pro Glu Val Lys Phe Asn Trp Tyr Val
                180                 185                 190

Asp Gly Val Glu Val His Asn Ala Lys Thr Lys Pro Arg Glu Glu Gln
        195                 200                 205

Tyr Asn Ser Thr Tyr Arg Val Val Ser Val Leu Thr Val Leu His Gln
210                 215                 220

Asp Trp Leu Asn Gly Lys Glu Tyr Lys Cys Lys Val Ser Asn Lys Ala
225                 230                 235                 240

Leu Pro Ala Pro Ile Glu Lys Thr Ile Ser Lys Ala Lys Gly Gln Pro
                245                 250                 255

Arg Glu Pro Gln Val Tyr Thr Leu Pro Pro Ser Arg Asp Glu Leu Thr
                260                 265                 270

Lys Asn Gln Val Ser Leu Thr Cys Leu Val Lys Gly Phe Tyr Pro Ser
        275                 280                 285

Asp Ile Ala Val Glu Trp Glu Ser Asn Gly Gln Pro Glu Asn Asn Tyr
        290                 295                 300

Lys Thr Thr Pro Pro Val Leu Asp Ser Asp Gly Ser Phe Phe Leu Tyr
305                 310                 315                 320

Ser Lys Leu Thr Val Asp Lys Ser Arg Trp Gln Gln Gly Asn Val Phe
                325                 330                 335
```

```
Ser Cys Ser Val Met His Glu Ala Leu His Asn His Tyr Thr Gln Lys
            340                 345                 350
Ser Leu Ser Leu Ser Pro Gly Lys
        355                 360

<210> SEQ ID NO 117
<211> LENGTH: 362
<212> TYPE: PRT
<213> ORGANISM: Artificial Sequence
<220> FEATURE:
<223> OTHER INFORMATION: Synthetic Polypeptide

<400> SEQUENCE: 117

Gln Val Gln Leu Gln Glu Ser Gly Gly Gly Pro Val Gln Ala Gly Gly
1               5                   10                  15
Ser Leu Arg Leu Ser Cys Ala Val Ser Lys Tyr Pro Tyr Ser Gly Ser
            20                  25                  30
Cys Met Gly Trp Phe Arg Gln Ala Pro Gly Lys Glu Arg Glu Gly Val
        35                  40                  45
Ala Ala Met Phe Thr Gly Thr Gly Ser Thr Tyr Tyr Ala Asp Ser Val
    50                  55                  60
Lys Gly Arg Phe Thr Ile Ser Gln Asn Val Ala Lys Asn Thr Leu Asp
65                  70                  75                  80
Leu Gln Met Asn Ser Leu Lys Pro Glu Asp Thr Ala Met Tyr Tyr Cys
                85                  90                  95
Ala Val Asp Leu Leu Pro Arg Ser Thr Arg Cys Leu Asp Tyr Gly Leu
            100                 105                 110
Arg Thr Tyr Asn Tyr Trp Gly Gln Gly Thr Gln Val Thr Val Ser Ser
        115                 120                 125
Gly Ser Glu Pro Lys Ser Cys Asp Lys Thr His Thr Cys Pro Pro Cys
    130                 135                 140
Pro Ala Pro Glu Leu Leu Gly Gly Pro Ser Val Phe Leu Phe Pro Pro
145                 150                 155                 160
Lys Pro Lys Asp Thr Leu Met Ile Ser Arg Thr Pro Glu Val Thr Cys
                165                 170                 175
Val Val Val Asp Val Ser His Glu Asp Pro Glu Val Lys Phe Asn Trp
            180                 185                 190
Tyr Val Asp Gly Val Glu Val His Asn Ala Lys Thr Lys Pro Arg Glu
        195                 200                 205
Glu Gln Tyr Asn Ser Thr Tyr Arg Val Val Ser Val Leu Thr Val Leu
    210                 215                 220
His Gln Asp Trp Leu Asn Gly Lys Glu Tyr Lys Cys Lys Val Ser Asn
225                 230                 235                 240
Lys Ala Leu Pro Ala Pro Ile Glu Lys Thr Ile Ser Lys Ala Lys Gly
                245                 250                 255
Gln Pro Arg Glu Pro Gln Val Tyr Thr Leu Pro Pro Ser Arg Asp Glu
            260                 265                 270
Leu Thr Lys Asn Gln Val Ser Leu Thr Cys Leu Val Lys Gly Phe Tyr
        275                 280                 285
Pro Ser Asp Ile Ala Val Glu Trp Glu Ser Asn Gly Gln Pro Glu Asn
    290                 295                 300
Asn Tyr Lys Thr Thr Pro Pro Val Leu Asp Ser Asp Gly Ser Phe Phe
305                 310                 315                 320
Leu Tyr Ser Lys Leu Thr Val Asp Lys Ser Arg Trp Gln Gln Gly Asn
                325                 330                 335
```

```
Val Phe Ser Cys Ser Val Met His Glu Ala Leu His Asn His Tyr Thr
                340                 345                 350

Gln Lys Ser Leu Ser Leu Ser Pro Gly Lys
        355                 360

<210> SEQ ID NO 118
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 118

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335
```

His Glu Ala Leu His Asn His Tyr Thr Gln Lys Ser Leu Ser Leu Ser
                340                 345                 350

Pro Gly Lys
        355

<210> SEQ ID NO 119
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 119

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

```
His Glu Ala Leu His Asn His Tyr Thr Gln Lys Ser Leu Ser Leu Ser
                340                 345                 350

Pro Gly Lys
        355

<210> SEQ ID NO 120
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 120

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335
```

```
His Glu Ala Leu His Asn His Tyr Thr Gln Lys Ser Leu Ser Leu Ser
                340                 345                 350

Pro Gly Lys
        355

<210> SEQ ID NO 121
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 121

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335
```

His Glu Ala Leu His Asn His Tyr Thr Gln Lys Ser Leu Ser Leu Ser
                340                 345                 350

Pro Gly Lys
        355

<210> SEQ ID NO 122
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 122

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
            340                 345                 350

Pro Gly Lys
        355

<210> SEQ ID NO 123
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 123

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Gln Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
                340                 345                 350

Pro Gly Lys
        355

<210> SEQ ID NO 124
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 124

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Glu Arg Glu Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
                340                 345                 350

Pro Gly Lys
        355

<210> SEQ ID NO 125
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 125

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

-continued

His Glu Ala Leu His Asn His Tyr Thr Gln Lys Ser Leu Ser Leu Ser
                340                 345                 350

Pro Gly Lys
        355

<210> SEQ ID NO 126
<211> LENGTH: 355
<212> TYPE: PRT
<213> ORGANISM: Artificial Sequence
<220> FEATURE:
<223> OTHER INFORMATION: Synthetic Polypeptide

<400> SEQUENCE: 126

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Asp Lys Thr His Thr Cys Pro Pro Cys Pro Ala Pro Glu Leu Leu Gly
    130                 135                 140

Gly Pro Ser Val Phe Leu Phe Pro Pro Lys Pro Lys Asp Thr Leu Met
145                 150                 155                 160

Ile Ser Arg Thr Pro Glu Val Thr Cys Val Val Val Asp Val Ser His
                165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
        195                 200                 205

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
            260                 265                 270

Leu Thr Cys Leu Val Lys Gly Phe Tyr Pro Ser Asp Ile Ala Val Glu
        275                 280                 285

Trp Glu Ser Asn Gly Gln Pro Glu Asn Asn Tyr Lys Thr Thr Pro Pro
    290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

```
His Glu Ala Leu His Asn His Tyr Thr Gln Lys Ser Leu Ser Leu Ser
                340                 345                 350

Pro Gly Lys
        355

<210> SEQ ID NO 127
<211> LENGTH: 490
<212> TYPE: PRT
<213> ORGANISM: Artificial Sequence
<220> FEATURE:
<223> OTHER INFORMATION: Synthetic Polypeptide

<400> SEQUENCE: 127

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Val Gly Val
        35                  40                  45

Ala Ala Ile Ser Ile Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Gly Ser Gln Val Gln Leu Val Glu Ser Gly Gly Gly Leu Val Gln Pro
    130                 135                 140

Gly Gly Ser Leu Arg Leu Ser Cys Ala Ala Ser Gly Tyr Ile Tyr Ser
145                 150                 155                 160

Ala Tyr Cys Met Gly Trp Phe Arg Gln Ala Pro Gly Lys Gly Leu Val
                165                 170                 175

Gly Val Ala Ala Ile Ser Ile Gly Gly Ser Thr Tyr Tyr Ala Asp
            180                 185                 190

Ser Val Lys Gly Arg Phe Thr Ile Ser Arg Asp Asn Ser Lys Asn Thr
        195                 200                 205

Leu Tyr Leu Gln Met Asn Ser Leu Arg Ala Glu Asp Thr Ala Val Tyr
    210                 215                 220

Tyr Cys Ala Ala Asp Val Ile Pro Thr Glu Thr Cys Leu Gly Gly Ser
225                 230                 235                 240

Trp Ser Gly Pro Phe Gly Tyr Trp Gly Gln Gly Thr Leu Val Thr Val
                245                 250                 255

Ser Ser Glu Pro Lys Ser Ser Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335
```

```
Glu Gln Tyr Asn Ser Thr Tyr Arg Val Val Ser Val Leu Thr Val Leu
                340                 345                 350

His Gln Asp Trp Leu Asn Gly Lys Glu Tyr Lys Cys Lys Val Ser Asn
            355                 360                 365

Lys Ala Leu Pro Ala Pro Ile Glu Lys Thr Ile Ser Lys Ala Lys Gly
        370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 128
<211> LENGTH: 490
<212> TYPE: PRT
<213> ORGANISM: Artificial Sequence
<220> FEATURE:
<223> OTHER INFORMATION: Synthetic Polypeptide

<400> SEQUENCE: 128

Gln Val Gln Leu Val Glu Ser Gly Gly Gly Leu Val Gln Pro Gly Gly
1               5                   10                  15

Ser Leu Arg Leu Ser Cys Ala Ala Ser Gly Tyr Ile Tyr Ser Ala Tyr
            20                  25                  30

Cys Met Gly Trp Phe Arg Gln Ala Pro Gly Lys Gly Leu Glu Gly Val
        35                  40                  45

Ala Ala Ile Tyr Ile Gly Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ala Asp Val Ile Pro Thr Glu Thr Cys Leu Gly Gly Ser Trp Ser
            100                 105                 110

Gly Pro Phe Gly Tyr Trp Gly Gln Gly Thr Leu Val Thr Val Ser Ser
        115                 120                 125

Gly Ser Gln Val Gln Leu Val Glu Ser Gly Gly Gly Leu Val Gln Pro
    130                 135                 140

Gly Gly Ser Leu Arg Leu Ser Cys Ala Ala Ser Gly Tyr Ile Tyr Ser
145                 150                 155                 160

Ala Tyr Cys Met Gly Trp Phe Arg Gln Ala Pro Gly Lys Gly Leu Glu
                165                 170                 175

Gly Val Ala Ala Ile Tyr Ile Gly Gly Gly Ser Thr Tyr Tyr Ala Asp
            180                 185                 190

Ser Val Lys Gly Arg Phe Thr Ile Ser Arg Asp Asn Ser Lys Asn Thr
        195                 200                 205
```

```
Leu Tyr Leu Gln Met Asn Ser Leu Arg Ala Glu Asp Thr Ala Val Tyr
    210                 215                 220

Tyr Cys Ala Ala Asp Val Ile Pro Thr Glu Thr Cys Leu Gly Gly Ser
225                 230                 235                 240

Trp Ser Gly Pro Phe Gly Tyr Trp Gly Gln Gly Thr Leu Val Thr Val
                245                 250                 255

Ser Ser Glu Pro Lys Ser Ser Asp Lys Thr His Thr Cys Pro Pro Cys
            260                 265                 270

Pro Ala Pro Glu Leu Leu Gly Gly Pro Ser Val Phe Leu Phe Pro Pro
        275                 280                 285

Lys Pro Lys Asp Thr Leu Met Ile Ser Arg Thr Pro Glu Val Thr Cys
    290                 295                 300

Val Val Val Asp Val Ser His Glu Asp Pro Glu Val Lys Phe Asn Trp
305                 310                 315                 320

Tyr Val Asp Gly Val Glu Val His Asn Ala Lys Thr Lys Pro Arg Glu
                325                 330                 335

Glu Gln Tyr Asn Ser Thr Tyr Arg Val Val Ser Val Leu Thr Val Leu
            340                 345                 350

His Gln Asp Trp Leu Asn Gly Lys Glu Tyr Lys Cys Lys Val Ser Asn
        355                 360                 365

Lys Ala Leu Pro Ala Pro Ile Glu Lys Thr Ile Ser Lys Ala Lys Gly
    370                 375                 380

Gln Pro Arg Glu Pro Gln Val Tyr Thr Leu Pro Pro Ser Arg Asp Glu
385                 390                 395                 400

Leu Thr Lys Asn Gln Val Ser Leu Thr Cys Leu Val Lys Gly Phe Tyr
                405                 410                 415

Pro Ser Asp Ile Ala Val Glu Trp Glu Ser Asn Gly Gln Pro Glu Asn
            420                 425                 430

Asn Tyr Lys Thr Thr Pro Pro Val Leu Asp Ser Asp Gly Ser Phe Phe
        435                 440                 445

Leu Tyr Ser Lys Leu Thr Val Asp Lys Ser Arg Trp Gln Gln Gly Asn
    450                 455                 460

Val Phe Ser Cys Ser Val Met His Glu Ala Leu His Asn His Tyr Thr
465                 470                 475                 480

Gln Lys Ser Leu Ser Leu Ser Pro Gly Lys
                485                 490

<210> SEQ ID NO 129
<211> LENGTH: 357
<212> TYPE: PRT
<213> ORGANISM: Artificial Sequence
<220> FEATURE:
<223> OTHER INFORMATION: Synthetic Polypeptide

<400> SEQUENCE: 129

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80
```

Gly Leu Arg Ala Met Asp Thr Gly Leu Tyr Ile Cys Lys Val Glu Leu
                85                  90                  95

Met Tyr Pro Pro Pro Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Cys Pro Cys Pro Ala Pro Glu Leu
130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
        275                 280                 285

Val Glu Trp Glu Ser Asn Gly Gln Pro Glu Asn Asn Tyr Lys Thr Thr
    290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
        355

<210> SEQ ID NO 130
<211> LENGTH: 440
<212> TYPE: PRT
<213> ORGANISM: Artificial Sequence
<220> FEATURE:
<223> OTHER INFORMATION: Synthetic Polypeptide

<400> SEQUENCE: 130

Val Ile His Val Thr Lys Glu Val Lys Glu Val Ala Thr Leu Ser Cys
1               5                   10                  15

Gly His Asn Val Ser Val Glu Glu Leu Ala Gln Thr Arg Ile Tyr Trp
            20                  25                  30

Gln Lys Glu Lys Lys Met Val Leu Thr Met Met Ser Gly Asp Met Asn
        35                  40                  45

Ile Trp Pro Glu Tyr Lys Asn Arg Thr Ile Phe Asp Ile Thr Asn Asn
    50                  55                  60

Leu Ser Ile Val Ile Leu Ala Leu Arg Pro Ser Asp Glu Gly Thr Tyr
65                  70                  75                  80

Glu Cys Val Val Leu Lys Tyr Glu Lys Asp Ala Phe Lys Arg Glu His
            85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
            115                 120                 125

Ser Thr Ser Gly Gly Phe Pro Glu Pro His Leu Ser Trp Leu Glu Asn
130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
            165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
            195                 200                 205

Ile Glu Gly Arg Met Asp Lys Thr His Thr Cys Pro Pro Cys Pro Ala
210                 215                 220

Pro Glu Leu Leu Gly Gly Pro Ser Val Phe Leu Phe Pro Pro Lys Pro
225                 230                 235                 240

Lys Asp Thr Leu Met Ile Ser Arg Thr Pro Glu Val Thr Cys Val Val
            245                 250                 255

Val Asp Val Ser His Glu Asp Pro Glu Val Lys Phe Asn Trp Tyr Val
            260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
            290                 295                 300

Asp Trp Leu Asn Gly Lys Glu Tyr Lys Cys Lys Val Ser Asn Lys Ala
305                 310                 315                 320

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Asp Glu Leu Thr
            340                 345                 350

Lys Asn Gln Val Ser Leu Thr Cys Leu Val Lys Gly Phe Tyr Pro Ser
            355                 360                 365

Asp Ile Ala Val Glu Trp Glu Ser Asn Gly Gln Pro Glu Asn Asn Tyr
            370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
            435                 440

<210> SEQ ID NO 131
<211> LENGTH: 361
<212> TYPE: PRT
<213> ORGANISM: Artificial Sequence
<220> FEATURE:
<223> OTHER INFORMATION: Synthetic Polypeptide

<400> SEQUENCE: 131

```
Glu Ala Ile Gln Val Thr Gln Pro Ser Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
            100                 105                 110

Gln Ile Tyr Val Ile Asp Pro Glu Pro Cys Pro Asp Ser Asp Gly Ser
        115                 120                 125

Met Asp Pro Lys Ser Ser Asp Lys Thr His Thr Cys Pro Pro Cys Pro
130                 135                 140

Ala Pro Glu Leu Leu Gly Gly Pro Ser Val Phe Leu Phe Pro Pro Lys
145                 150                 155                 160

Pro Lys Asp Thr Leu Met Ile Ser Arg Thr Pro Glu Val Thr Cys Val
                165                 170                 175

Val Val Asp Val Ser His Glu Asp Pro Glu Val Lys Phe Asn Trp Tyr
            180                 185                 190

Val Asp Gly Val Glu Val His Asn Ala Lys Thr Lys Pro Arg Glu Glu
        195                 200                 205

Gln Tyr Asn Ser Thr Tyr Arg Val Val Ser Val Leu Thr Val Leu His
    210                 215                 220

Gln Asp Trp Leu Asn Gly Lys Glu Tyr Lys Cys Lys Val Ser Asn Lys
225                 230                 235                 240

Ala Leu Pro Ala Pro Ile Glu Lys Thr Ile Ser Lys Ala Lys Gly Gln
                245                 250                 255

Pro Arg Glu Pro Gln Val Tyr Thr Leu Pro Pro Ser Arg Asp Glu Leu
            260                 265                 270

Thr Lys Asn Gln Val Ser Leu Thr Cys Leu Val Lys Gly Phe Tyr Pro
        275                 280                 285

Ser Asp Ile Ala Val Glu Trp Glu Ser Asn Gly Gln Pro Glu Asn Asn
    290                 295                 300

Tyr Lys Thr Thr Pro Pro Val Leu Asp Ser Asp Gly Ser Phe Phe Leu
305                 310                 315                 320

Tyr Ser Lys Leu Thr Val Asp Lys Ser Arg Trp Gln Gln Gly Asn Val
                325                 330                 335

Phe Ser Cys Ser Val Met His Glu Ala Leu His Asn His Tyr Thr Gln
            340                 345                 350

Lys Ser Leu Ser Leu Ser Pro Gly Lys
        355                 360
```

<210> SEQ ID NO 132
<211> LENGTH: 232
<212> TYPE: PRT
<213> ORGANISM: Artificial Sequence
<220> FEATURE:
<223> OTHER INFORMATION: Synthetic Polypeptide

<400> SEQUENCE: 132

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
210                 215                 220

Ser Leu Ser Leu Ser Pro Gly Lys
225                 230
```

<210> SEQ ID NO 133
<211> LENGTH: 357
<212> TYPE: PRT
<213> ORGANISM: Artificial Sequence
<220> FEATURE:
<223> OTHER INFORMATION: Synthetic Polypeptide

<400> SEQUENCE: 133

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110
```

-continued

```
Tyr Val Ile Asp Pro Glu Pro Cys Pro Asp Ser Asp Gln Gly Ser Met
        115                 120                 125
Asp Pro Lys Ser Ser Asp Lys Thr His Thr Cys Pro Pro Cys Pro Ala
        130                 135                 140
Pro Glu Val Ser Ser Val Phe Ile Phe Pro Pro Lys Pro Lys Asp Val
145                 150                 155                 160
Leu Thr Ile Thr Leu Thr Pro Lys Val Thr Cys Val Val Val Asp Ile
                165                 170                 175
Ser Lys Asp Asp Pro Glu Val Gln Phe Ser Trp Phe Val Asp Asp Val
                180                 185                 190
Glu Val His Thr Ala Gln Thr Gln Pro Arg Glu Glu Gln Phe Asn Ser
        195                 200                 205
Thr Phe Arg Ser Val Ser Glu Leu Pro Ile Met His Gln Asp Trp Leu
        210                 215                 220
Asn Gly Lys Glu Phe Lys Cys Arg Val Asn Ser Ala Ala Phe Pro Ala
225                 230                 235                 240
Pro Ile Glu Lys Thr Ile Ser Lys Thr Lys Gly Arg Pro Lys Ala Pro
                245                 250                 255
Gln Val Tyr Thr Ile Pro Pro Lys Glu Gln Met Ala Lys Asp Lys
                260                 265                 270
Val Ser Leu Thr Cys Met Ile Thr Asp Phe Phe Pro Glu Asp Ile Thr
        275                 280                 285
Val Glu Trp Gln Trp Asn Gly Gln Pro Ala Glu Asn Tyr Lys Asn Thr
        290                 295                 300
Gln Pro Ile Met Asn Thr Asn Gly Ser Tyr Phe Val Tyr Ser Lys Leu
305                 310                 315                 320
Asn Val Gln Lys Ser Asn Trp Glu Ala Gly Asn Thr Phe Thr Cys Ser
                325                 330                 335
Val Leu His Glu Gly Leu His Asn His His Thr Glu Lys Ser Leu Ser
        340                 345                 350
His Ser Pro Gly Lys
        355
```